US012797347B2

(12) United States Patent
Lu et al.

(10) Patent No.: US 12,797,347 B2
(45) Date of Patent: *Nov. 17, 2026

(54) ENGAGING THE CERVICAL SPINAL CORD CIRCUITRY TO RE- ENABLE VOLITIONAL CONTROL OF HAND FUNCTION IN TETRAPLEGIC SUBJECTS

(71) Applicant: The Regents of the University of California, Oakland, CA (US)

(72) Inventors: Daniel C. Lu, Los Angeles, CA (US); V. Reggie Edgerton, Los Angeles, CA (US); Roland R. Roy, Playa Vista, CA (US); Yury P. Gerasimenko, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/335,824

(22) Filed: Sep. 22, 2025

(65) Prior Publication Data

US 2026/0060941 A1 Mar. 5, 2026

Related U.S. Application Data

(63) Continuation of application No. 18/782,349, filed on Jul. 24, 2024, which is a continuation of application (Continued)

(51) Int. Cl.

*A61N 1/362* (2006.01)
*A61K 31/137* (2006.01)

(Continued)

(52) U.S. Cl.

CPC ........ *A61K 31/137* (2013.01); *A61K 31/4168* (2013.01); *A61K 31/4178* (2013.01);

(Continued)

(58) Field of Classification Search

CPC .............. A61K 31/137; A61K 31/4168; A61K 31/4178; A61K 31/496; A61K 31/4985;

(Continued)

(56) References Cited

U.S. PATENT DOCUMENTS 2,868,343 A 1/1959 Sproul
3,543,761 A 12/1970 Bradley (Continued)

FOREIGN PATENT DOCUMENTS

AU 2012204526 A1 7/2013
AU 2012204526 5/2016

(Continued)

OTHER PUBLICATIONS

US Office Action dated Apr. 8, 2015 issued in U.S. Appl. No. 14/355,812 [UCLAP080US].

(Continued)

*Primary Examiner* — Jon Eric C Morales

(74) *Attorney, Agent, or Firm* — Mark S. Cohen; PEARL COHEN LLP

(57) ABSTRACT

In various embodiments, methods are provided for applying transcutaneous and/or epidural spinal cord stimulation with and without selective pharmaceuticals to restore voluntary control of hand function in tetraplegic subjects.

23 Claims, 12 Drawing Sheets

Related U.S. Application Data

No. 17/407,043, filed on Aug. 19, 2021, now Pat. No. 12,076,301, which is a continuation of application No. 16/200,467, filed on Nov. 26, 2018, now Pat. No. 11,123,312, which is a continuation of application No. 15/025,201, filed as application No. PCT/US2014/057886 on Sep. 26, 2014, now Pat. No. 10,137,299.

(60) Provisional application No. 61/883,694, filed on Sep. 27, 2013.

(51) Int. Cl.

| | |
|---|---|
| ***A61K 31/4168*** | (2006.01) |
| ***A61K 31/4178*** | (2006.01) |
| ***A61K 31/496*** | (2006.01) |
| ***A61K 31/4985*** | (2006.01) |
| ***A61K 31/506*** | (2006.01) |
| ***A61K 31/517*** | (2006.01) |
| ***A61K 31/527*** | (2006.01) |
| ***A61M 5/172*** | (2006.01) |
| ***A61N 1/05*** | (2006.01) |
| ***A61N 1/36*** | (2006.01) |

(52) U.S. Cl.
CPC ........ *A61K 31/496* (2013.01); *A61K 31/4985* (2013.01); *A61K 31/506* (2013.01); *A61K 31/517* (2013.01); *A61K 31/527* (2013.01); *A61N 1/0551* (2013.01); *A61N 1/36003* (2013.01); *A61N 1/36034* (2017.08); *A61N 1/36067* (2013.01); *A61N 1/36171* (2013.01)

(58) Field of Classification Search
CPC ................ A61K 31/506; A61K 31/517; A61K 31/527; A61N 1/0456; A61N 1/0551; A61N 1/36003; A61N 1/36034; A61N 1/36067; A61N 1/36171; A61P 25/02
See application file for complete search history.

(56) References Cited

U.S. PATENT DOCUMENTS

| | | | |
|---|---|---|---|
| 3,650,277 | A | 3/1972 | Sjostrand et al. |
| 3,653,518 | A | 4/1972 | Polen |
| 3,662,758 | A | 5/1972 | Glover |
| 3,724,467 | A | 4/1973 | Avery et al. |
| 4,044,774 | A | 8/1977 | Corbin et al. |
| 4,102,344 | A | 7/1978 | Conway et al. |
| 4,141,365 | A | 2/1979 | Fischell et al. |
| 4,285,347 | A | 8/1981 | Hess |
| 4,303,904 | A | 12/1981 | Chasek |
| 4,340,063 | A | 7/1982 | Maurer |
| 4,340,216 | A | 7/1982 | Murphy |
| 4,356,902 | A | 11/1982 | Murphy |
| 4,379,462 | A | 4/1983 | Borkan et al. |
| 4,398,537 | A | 8/1983 | Holmbo |
| 4,402,501 | A | 9/1983 | Lohman |
| 4,410,175 | A | 10/1983 | Shamp |
| 4,414,986 | A | 11/1983 | Dickhudt et al. |
| 4,538,624 | A | 9/1985 | Tarjan |
| 4,549,556 | A | 10/1985 | Tajan et al. |
| 4,559,948 | A | 12/1985 | Liss et al. |
| 4,569,352 | A | 2/1986 | Petrofsky et al. |
| 4,573,481 | A | 3/1986 | Bullara et al. |
| 4,574,789 | A | 3/1986 | Forster |
| 4,724,842 | A | 2/1988 | Charters |
| 4,742,054 | A | 5/1988 | Naftchi |
| 4,784,420 | A | 11/1988 | Makino et al. |
| 4,798,982 | A | 1/1989 | Voorman |
| 4,800,898 | A | 1/1989 | Hess et al. |
| 4,934,368 | A | 6/1990 | Lynch |
| 4,969,452 | A | 11/1990 | Petrofsky et al. |
| 5,002,053 | A | 3/1991 | Garcia-Rill et al. |
| 5,018,631 | A | 5/1991 | Reimer |
| 5,031,618 | A | 7/1991 | Mullett |
| 5,066,272 | A | 11/1991 | Eaton et al. |
| 5,081,989 | A | 1/1992 | Graupe et al. |
| 5,121,754 | A | 6/1992 | Mullett |
| 5,284,151 | A | 2/1994 | Onoda |
| 5,337,908 | A | 8/1994 | Beck, Jr. |
| 5,344,439 | A | 9/1994 | Otten |
| 5,348,544 | A | 9/1994 | Sweeney et al. |
| 5,354,320 | A | 10/1994 | Schaldach et al. |
| 5,366,813 | A | 11/1994 | Berlin |
| 5,374,285 | A | 12/1994 | Vaiani et al. |
| 5,417,719 | A | 5/1995 | Hull et al. |
| 5,421,783 | A | 6/1995 | Kockelman et al. |
| 5,441,465 | A | 8/1995 | Hefner et al. |
| 5,443,486 | A | 8/1995 | Hrdlicka et al. |
| 5,476,441 | A | 12/1995 | Durfee et al. |
| 5,553,270 | A | 9/1996 | Rosenbluth |
| 5,562,718 | A | 10/1996 | Palermo |
| 5,571,141 | A | 11/1996 | McNeil et al. |
| 5,584,818 | A | 12/1996 | Morrison |
| 5,601,527 | A | 2/1997 | Selkowitz |
| 5,626,540 | A | 5/1997 | Hall |
| 5,630,836 | A | 5/1997 | Prem et al. |
| 5,643,330 | A | 7/1997 | Holsheimer et al. |
| 5,643,332 | A | 7/1997 | Stein |
| 5,667,461 | A | 9/1997 | Hall |
| 5,733,322 | A | 3/1998 | Starkebaum |
| 5,788,606 | A | 8/1998 | Rich |
| 5,814,018 | A | 9/1998 | Elson et al. |
| 5,819,962 | A | 10/1998 | Okubo et al. |
| 5,876,425 | A | 3/1999 | Gord et al. |
| 5,877,183 | A | 3/1999 | Cincotta |
| 5,948,004 | A | 9/1999 | Weijand et al. |
| 5,958,933 | A | 9/1999 | Naftchi |
| 5,983,141 | A | 11/1999 | Sluijter et al. |
| 5,984,368 | A | 11/1999 | Cain |
| 6,052,624 | A | 4/2000 | Mann |
| 6,058,331 | A | 5/2000 | King |
| 6,066,163 | A | 5/2000 | John |
| 6,080,087 | A | 6/2000 | Bingham |
| 6,104,957 | A | 8/2000 | Alo et al. |
| 6,115,634 | A | 9/2000 | Donders et al. |
| 6,122,548 | A | 9/2000 | Starkebaum et al. |
| 6,139,475 | A | 10/2000 | Bessler et al. |
| 6,168,948 | B1 | 1/2001 | Anderson et al. |
| 6,182,843 | B1 | 2/2001 | Tax et al. |
| 6,188,927 | B1 | 2/2001 | Lu et al. |
| 6,236,892 | B1 | 5/2001 | Feler |
| 6,280,640 | B1 | 8/2001 | Hurwitz et al. |
| 6,281,207 | B1 | 8/2001 | Richter et al. |
| 6,308,103 | B1 | 10/2001 | Gielen |
| 6,309,401 | B1 | 10/2001 | Redko et al. |
| 6,319,241 | B1 | 11/2001 | King et al. |
| D454,139 | S | 3/2002 | Feldcamp |
| 6,463,327 | B1 | 10/2002 | Lurie et al. |
| 6,464,208 | B1 | 10/2002 | Smith |
| 6,470,213 | B1 | 10/2002 | Alley |
| 6,490,486 | B1 | 12/2002 | Bradley |
| 6,500,110 | B1 | 12/2002 | Davey et al. |
| 6,503,231 | B1 | 1/2003 | Prausnitz et al. |
| 6,505,074 | B2 | 1/2003 | Boveja et al. |
| 6,516,227 | B1 | 2/2003 | Meadows et al. |
| 6,551,849 | B1 | 4/2003 | Kenney |
| 6,587,724 | B2 | 7/2003 | Mann |
| 6,662,053 | B2 | 12/2003 | Borkan |
| 6,666,831 | B1 | 12/2003 | Edgerton et al. |
| 6,685,729 | B2 | 2/2004 | Gonzalez |
| 6,748,276 | B1 | 6/2004 | Daignault, Jr. et al. |
| 6,819,956 | B2 | 11/2004 | DiLorenzo |
| 6,839,594 | B2 | 1/2005 | Cohen et al. |
| 6,862,479 | B1 | 3/2005 | Whitehurst et al. |
| 6,871,099 | B1 | 3/2005 | Whitehurst et al. |
| 6,878,112 | B2 | 4/2005 | Linberg et al. |
| 6,892,098 | B2 | 5/2005 | Ayal et al. |
| 6,895,280 | B2 | 5/2005 | Meadows et al. |
| 6,895,283 | B2 | 5/2005 | Erickson et al. |
| 6,901,292 | B2 | 5/2005 | Hrdlicka et al. |

(56) References Cited

U.S. PATENT DOCUMENTS 6,937,891 B2 8/2005 Leinders et al.
6,950,706 B2 9/2005 Rodriguez et al.
6,975,907 B2 12/2005 Zanakis et al.
6,978,181 B1 12/2005 Snell
6,988,006 B2 1/2006 King et al.
6,999,820 B2 2/2006 Jordan
7,010,749 B2 3/2006 Hasha et al.
7,020,521 B1 3/2006 Brewer et al.
7,024,247 B2 4/2006 Gliner et al.
7,035,690 B2 4/2006 Goetz
7,047,084 B2 5/2006 Erickson et al.
7,065,408 B2 6/2006 Herman et al.
7,096,070 B1 8/2006 Jenkins et al.
7,099,718 B1 8/2006 Thacker et al.
7,110,820 B2 9/2006 Tcheng et al.
7,125,388 B1 10/2006 Reinkensmeyer et al.
7,127,287 B2 10/2006 Duncan et al.
7,127,296 B2 10/2006 Bradley
7,127,297 B2 10/2006 Law et al.
7,135,497 B1 11/2006 Zeman et al.
7,146,221 B2 12/2006 Krulevitch et al.
7,149,773 B2 12/2006 Haller et al.
7,153,242 B2 12/2006 Goffer
7,184,837 B2 2/2007 Goetz
7,200,443 B2 4/2007 Faul
7,209,787 B2 4/2007 DiLorenzo
7,228,179 B2 6/2007 Campen et al.
7,239,920 B1 7/2007 Thacker et al.
7,251,529 B2 7/2007 Greenwood-Van Meerveld
7,252,090 B2 8/2007 Goetz
7,313,440 B2 12/2007 Miesel et al.
7,324,853 B2 1/2008 Ayal et al.
7,330,760 B2 2/2008 Heruth et al.
7,330,762 B2 2/2008 Boveja et al.
7,337,005 B2 2/2008 Kim et al.
7,337,006 B2 2/2008 Kim et al.
7,340,298 B1 3/2008 Barbut
7,377,006 B2 5/2008 Genoa et al.
7,381,192 B2 6/2008 Brodard et al.
7,415,309 B2 8/2008 Mcintyre
7,450,992 B1 11/2008 Cameron
7,463,927 B1 12/2008 Chaouat
7,463,928 B2 12/2008 Lee et al.
7,467,016 B2 12/2008 Colborn
7,493,170 B1 2/2009 Segel et al.
7,496,404 B2 2/2009 Meadows et al.
7,502,652 B2 3/2009 Gaunt et al.
7,536,226 B2 5/2009 Williams et al.
D594,024 S 6/2009 King
D595,308 S 6/2009 King
7,544,185 B2 6/2009 Bengtsson
7,565,195 B1 7/2009 Kroll et al.
7,584,000 B2 9/2009 Erickson
7,590,454 B2 9/2009 Garabedian et al.
7,603,178 B2 10/2009 North et al.
7,620,502 B2 11/2009 Selifonov et al.
7,628,750 B2 12/2009 Cohen et al.
7,647,115 B2 1/2010 Levin et al.
7,660,636 B2 2/2010 Castel et al.
7,697,995 B2 4/2010 Cross et al.
7,725,193 B1 5/2010 Chu
7,729,781 B2 6/2010 Swoyer et al.
7,734,340 B2 6/2010 De Ridder
7,734,351 B2 6/2010 Testerman et al.
7,742,037 B2 6/2010 Sako et al.
7,769,463 B2 8/2010 Katsnelson
7,769,464 B2 8/2010 Gerber et al.
7,780,617 B2 8/2010 Tornatore et al.
7,797,057 B2 9/2010 Harris
7,801,600 B1 9/2010 Carbunaru et al.
7,801,601 B2 9/2010 Maschino et al.
7,813,803 B2 10/2010 Heruth et al.
7,813,809 B2 10/2010 Strother et al.
7,840,270 B2 11/2010 Ignagni et al.
7,856,264 B2 12/2010 Firlik et al.
7,861,872 B2 1/2011 Ng et al.
7,877,146 B2 1/2011 Rezai et al.
7,890,182 B2 2/2011 Parramon et al.
D638,439 S 5/2011 Cavanaugh et al.
7,949,395 B2 5/2011 Kuzma
7,949,403 B2 5/2011 Palermo et al.
7,987,000 B2 7/2011 Moffitt et al.
7,991,465 B2 8/2011 Bartic et al.
8,019,427 B2 9/2011 Moffitt
8,050,773 B2 11/2011 Zhu
8,063,087 B2 11/2011 Chow et al.
8,100,815 B2 1/2012 Balaker et al.
8,108,051 B2 1/2012 Cross, Jr. et al.
8,108,052 B2 1/2012 Boling
D656,153 S 3/2012 Imamura et al.
8,131,358 B2 3/2012 Moffitt et al.
8,135,473 B2 3/2012 Miesel et al.
8,155,750 B2 4/2012 Jaax et al.
8,168,481 B2 5/2012 Hanaoka et al.
8,170,660 B2 5/2012 Dacey, Jr. et al.
8,190,262 B2 5/2012 Gerber et al.
8,195,304 B2 6/2012 Strother et al.
8,214,048 B1 7/2012 Whitehurst et al.
8,224,453 B2 7/2012 De Ridder
8,229,565 B2 7/2012 Kim et al.
8,238,666 B2 8/2012 Besley et al.
8,239,038 B2 8/2012 Wolf, II
8,260,436 B2 9/2012 Gerber et al.
8,265,770 B2 9/2012 Toy et al.
8,271,099 B1 9/2012 Swanson
8,295,936 B2 10/2012 Wahlstrand et al.
8,311,644 B2 11/2012 Moffitt et al.
8,326,569 B2 12/2012 Lee et al.
8,332,029 B2 12/2012 Glukhovsky et al.
8,332,047 B2 12/2012 Libbus et al.
8,332,053 B1 12/2012 Patterson et al.
8,346,366 B2 1/2013 Arle et al.
8,352,036 B2 1/2013 DiMarco et al.
8,355,791 B2 1/2013 Moffitt
8,355,797 B2 1/2013 Caparso et al.
8,364,273 B2 1/2013 De Ridder
8,369,961 B2 2/2013 Christman et al.
8,374,696 B2 2/2013 Sanchez et al.
D677,674 S 3/2013 Rampson et al.
8,407,576 B1 3/2013 Yin et al.
8,412,345 B2 4/2013 Moffitt
8,428,728 B2 4/2013 Sachs
8,442,655 B2 5/2013 Moffitt et al.
8,452,406 B2 5/2013 Arcot-Krishmamurthy et al.
D684,991 S 6/2013 Wenz et al.
D684,996 S 6/2013 Wenz et al.
8,463,400 B2 6/2013 Hegi et al.
D688,259 S 8/2013 Pearcy et al.
D689,086 S 9/2013 Philopoulos
8,543,200 B2 9/2013 Lane et al.
D691,154 S 10/2013 Talbot et al.
D691,172 S 10/2013 Wujcik et al.
8,588,884 B2 11/2013 Hegde et al.
D694,763 S 12/2013 Edwards et al.
8,626,300 B2 1/2014 Demarais et al.
8,630,717 B2 1/2014 Olson et al.
8,700,145 B2 4/2014 Kilgard et al.
8,712,546 B2 4/2014 Kim et al.
D705,241 S 5/2014 Chen et al.
D707,235 S 6/2014 Arnold et al.
8,740,825 B2 6/2014 Ehrenreich et al.
8,750,957 B2 6/2014 Tang et al.
RE45,030 E 7/2014 Stevenson et al.
8,766,928 B2 7/2014 Weeldreyer et al.
8,768,472 B2 7/2014 Fang et al.
8,768,481 B2 7/2014 Lane
8,788,046 B2 7/2014 Bennett et al.
8,805,542 B2 8/2014 Tai et al.
8,836,368 B2 9/2014 Afshar et al.
8,847,548 B2 9/2014 Kesler et al.
8,849,410 B2 9/2014 Walker et al.
8,849,418 B2 9/2014 Daglow
8,897,870 B2 11/2014 De Ridder
8,903,502 B2 12/2014 Perryman et al.

(56) References Cited

U.S. PATENT DOCUMENTS

D721,722 S 1/2015 Lee
8,957,549 B2 2/2015 Kesler et al.
D735,231 S 7/2015 Omiya
9,072,891 B1 7/2015 Rao
9,079,039 B2 7/2015 Carlson et al.
9,101,769 B2 8/2015 Edgerton et al.
D737,840 S 9/2015 Omiya
9,192,768 B2 11/2015 Yokoi et al.
9,205,259 B2 12/2015 Kim et al.
9,205,260 B2 12/2015 Kim et al.
9,205,261 B2 12/2015 Kim et al.
9,248,291 B2 2/2016 Mashiach
D750,664 S 3/2016 Chen et al.
9,272,139 B2 3/2016 Hamilton et al.
9,272,143 B2 3/2016 Libbus et al.
9,283,391 B2 3/2016 Ahmed
9,314,630 B2 4/2016 Levin et al.
D758,398 S 6/2016 Yu et al.
9,358,384 B2 6/2016 Dubuclet
D760,753 S 7/2016 Cheng et al.
D762,234 S 7/2016 Li et al.
9,393,409 B2 7/2016 Edgerton et al.
D763,273 S 8/2016 Hwang et al.
9,409,023 B2 8/2016 Burdick et al.
9,409,030 B2 8/2016 Perryman et al.
9,415,218 B2 8/2016 Edgerton et al.
9,421,365 B2 8/2016 Sumners et al.
D769,302 S 10/2016 Rodriguez
D770,468 S 11/2016 Carlson et al.
D770,470 S 11/2016 Jin
9,520,887 B1 12/2016 Zhuang et al.
D780,768 S 3/2017 Carlson et al.
9,592,358 B2 3/2017 Miller et al.
9,592,385 B2 3/2017 Kaula et al.
9,597,517 B2 3/2017 Moffitt
D783,032 S 4/2017 Cashner et al.
9,610,442 B2 4/2017 Yoo et al.
D788,134 S 5/2017 Wong et al.
9,639,982 B2 5/2017 Craik et al.
9,656,076 B2 5/2017 Trier et al.
D789,963 S 6/2017 Agashiwala et al.
D794,667 S 8/2017 Havaldar et al.
9,717,908 B2 8/2017 Karunasiri
9,724,513 B2 8/2017 Lane et al.
9,802,052 B2 10/2017 Marnfeldt
9,812,875 B2 11/2017 Nejatali et al.
D806,717 S 1/2018 Bae et al.
9,895,545 B2 2/2018 Rao et al.
D816,708 S 5/2018 Riedel et al.
D819,681 S 6/2018 Fung et al.
9,993,642 B2 6/2018 Gerasimenko et al.
10,092,750 B2 10/2018 Edgerton et al.
D834,601 S 11/2018 Felt
10,124,166 B2 11/2018 Edgerton et al.
10,137,299 B2 * 11/2018 Lu .......................... A61P 25/02
D839,278 S 1/2019 Carlson et al.
D839,914 S 2/2019 Lee et al.
D841,017 S 2/2019 Bathla
D843,388 S 3/2019 Protzman et al.
10,406,366 B2 9/2019 Westlund et al.
10,449,371 B2 10/2019 Serrano Carmona
D874,491 S 2/2020 Kuo et al.
D874,507 S 2/2020 Martell et al.
D875,108 S 2/2020 Chitalia et al.
D875,752 S 2/2020 Nelson et al.
D877,753 S 3/2020 Chitalia et al.
10,751,533 B2 8/2020 Edgerton et al.
10,758,732 B1 9/2020 Heldman
10,773,074 B2 9/2020 Liu et al.
10,799,701 B2 10/2020 Lee
10,806,927 B2 10/2020 Edgerton et al.
10,806,935 B2 10/2020 Rao et al.
D904,437 S 12/2020 Chitalia et al.
D905,701 S 12/2020 Feng et al.
10,881,853 B2 1/2021 Edgerton et al.
10,898,719 B2 1/2021 Pivonka et al.
D912,074 S 3/2021 Giannino et al.
D926,784 S 8/2021 Carlson et al.
D928,188 S 8/2021 Giannino et al.
11,097,122 B2 8/2021 Lu
11,123,312 B2 9/2021 Lu et al.
11,129,983 B2 9/2021 Lo et al.
D939,549 S 12/2021 Miyai et al.
D947,216 S 3/2022 Leininger
11,266,850 B2 3/2022 Prouza et al.
11,298,533 B2 4/2022 Edgerton et al.
D962,245 S 8/2022 Thompson et al.
11,400,284 B2 8/2022 Gerasimenko et al.
11,491,336 B2 11/2022 Scheltienne et al.
11,511,116 B2 11/2022 Wagner et al.
11,515,733 B2 11/2022 Babakhani et al.
11,638,820 B2 5/2023 Edgerton et al.
11,684,774 B2 6/2023 Crosby et al.
11,691,015 B2 7/2023 Minassian et al.
D1,008,290 S 12/2023 Stapfer
D1,008,291 S 12/2023 Stapfer
D1,010,666 S 1/2024 Cai et al.
11,911,621 B2 2/2024 Ganty et al.
11,944,814 B2 4/2024 Lo et al.
11,957,910 B2 4/2024 Edgerton et al.
11,986,653 B2 5/2024 Lo et al.
11,992,684 B2 5/2024 Minassian et al.
12,018,135 B2 6/2024 Scher et al.
12,023,492 B2 7/2024 Edgerton et al.
12,076,301 B2 * 9/2024 Lu ...................... A61K 31/4178
D1,044,827 S 10/2024 Tabrizi et al.
12,201,833 B2 1/2025 Edgerton et al.
12,214,198 B2 2/2025 Bennett et al.
12,268,878 B2 4/2025 Phillips et al.
12,415,079 B2 9/2025 Scheltienne et al.
2001/0016266 A1 8/2001 Okazaki et al.
2001/0032992 A1 10/2001 Wendt
2002/0042814 A1 4/2002 Fukasawa et al.
2002/0050456 A1 5/2002 Sheppard, Jr. et al.
2002/0052539 A1 5/2002 Haller et al.
2002/0055779 A1 5/2002 Andrews
2002/0083240 A1 6/2002 Hoese et al.
2002/0111661 A1 8/2002 Cross et al.
2002/0115945 A1 8/2002 Herman et al.
2002/0123672 A1 9/2002 Christophersom et al.
2002/0138512 A1 9/2002 Buresh et al.
2002/0173505 A1 11/2002 Skogvall
2002/0175931 A1 11/2002 Holtz et al.
2002/0187260 A1 12/2002 Sheppard, Jr. et al.
2002/0188332 A1 12/2002 Lurie et al.
2002/0193843 A1 12/2002 Hill et al.
2003/0032992 A1 2/2003 Thacker et al.
2003/0078633 A1 4/2003 Firlik et al.
2003/0093021 A1 5/2003 Goffer
2003/0093131 A1 5/2003 Loeb et al.
2003/0097166 A1 5/2003 Krulevitch et al.
2003/0100933 A1 5/2003 Ayal et al.
2003/0113725 A1 6/2003 Small et al.
2003/0114894 A1 6/2003 Dar et al.
2003/0114899 A1 6/2003 Woods et al.
2003/0135253 A1 7/2003 Kokones et al.
2003/0139422 A1 7/2003 Teng
2003/0145759 A1 8/2003 Rodnunsky
2003/0158583 A1 8/2003 Burnett et al.
2003/0199116 A1 10/2003 Tai et al.
2003/0200323 A1 10/2003 Dold et al.
2003/0208248 A1 11/2003 Carter et al.
2003/0220679 A1 11/2003 Han
2003/0233137 A1 12/2003 Paul, Jr.
2004/0039425 A1 2/2004 Greenwood-Van Meerveld
2004/0044380 A1 3/2004 Bruninga et al.
2004/0082979 A1 4/2004 Tong et al.
2004/0087286 A1 5/2004 Inoue et al.
2004/0088015 A1 5/2004 Casavant et al.
2004/0111118 A1 6/2004 Hill et al.
2004/0111126 A1 6/2004 Tanagho et al.
2004/0121528 A1 6/2004 Krulevitch et al.
2004/0122483 A1 6/2004 Nathan et al.
2004/0127954 A1 7/2004 McDonald, III

(56) References Cited

U.S. PATENT DOCUMENTS

| | | | |
|---|---|---|---|
| 2004/0133248 | A1 | 7/2004 | Frei et al. |
| 2004/0138518 | A1 | 7/2004 | Rise et al. |
| 2004/0147975 | A1 | 7/2004 | Popovic et al. |
| 2004/0172027 | A1 | 9/2004 | Speitling et al. |
| 2004/0172097 | A1 | 9/2004 | Brodard et al. |
| 2004/0181263 | A1 | 9/2004 | Balzer et al. |
| 2004/0192082 | A1 | 9/2004 | Wagner et al. |
| 2004/0192834 | A1 | 9/2004 | Nakayoshi et al. |
| 2004/0243204 | A1 | 12/2004 | Maghribi et al. |
| 2004/0267320 | A1 | 12/2004 | Taylor et al. |
| 2005/0004622 | A1 | 1/2005 | Cullen et al. |
| 2005/0043775 | A1 | 2/2005 | John et al. |
| 2005/0061315 | A1 | 3/2005 | Lee et al. |
| 2005/0070982 | A1 | 3/2005 | Heruth et al. |
| 2005/0075662 | A1 | 4/2005 | Pedersen et al. |
| 2005/0075669 | A1 | 4/2005 | King |
| 2005/0075678 | A1 | 4/2005 | Faul |
| 2005/0075693 | A1 | 4/2005 | Toy et al. |
| 2005/0080460 | A1 | 4/2005 | Wang et al. |
| 2005/0090756 | A1 | 4/2005 | Wolf et al. |
| 2005/0101827 | A1 | 5/2005 | Delisle |
| 2005/0102007 | A1 | 5/2005 | Ayal et al. |
| 2005/0113878 | A1 | 5/2005 | Gerber |
| 2005/0113882 | A1 | 5/2005 | Cameron et al. |
| 2005/0119713 | A1 | 6/2005 | Whitehurst et al. |
| 2005/0125045 | A1 | 6/2005 | Brighton et al. |
| 2005/0203588 | A1 | 9/2005 | King |
| 2005/0205961 | A1 | 9/2005 | Doong |
| 2005/0209655 | A1 | 9/2005 | Bradley et al. |
| 2005/0231186 | A1 | 10/2005 | Saavedra Barrera et al. |
| 2005/0239612 | A1 | 10/2005 | Keiser |
| 2005/0246004 | A1 | 11/2005 | Cameron et al. |
| 2005/0253273 | A1 | 11/2005 | Tai et al. |
| 2005/0277999 | A1 | 12/2005 | Strother et al. |
| 2005/0278000 | A1 | 12/2005 | Strother et al. |
| 2006/0003090 | A1 | 1/2006 | Rodger et al. |
| 2006/0007983 | A1 | 1/2006 | Tai et al. |
| 2006/0015153 | A1 | 1/2006 | Gliner et al. |
| 2006/0015470 | A1 | 1/2006 | Lauer et al. |
| 2006/0016266 | A1 | 1/2006 | Weise et al. |
| 2006/0018360 | A1 | 1/2006 | Tai et al. |
| 2006/0041225 | A1 | 2/2006 | Wallace et al. |
| 2006/0041295 | A1 | 2/2006 | Osypka |
| 2006/0047325 | A1 | 3/2006 | Thimineur et al. |
| 2006/0075339 | A1 | 4/2006 | Tomita et al. |
| 2006/0082626 | A1 | 4/2006 | Oikawa et al. |
| 2006/0089696 | A1 | 4/2006 | Olsen et al. |
| 2006/0095088 | A1 | 5/2006 | De Ridder |
| 2006/0100671 | A1 | 5/2006 | Ridder |
| 2006/0111754 | A1 | 5/2006 | Rezai et al. |
| 2006/0122678 | A1 | 6/2006 | Olsen et al. |
| 2006/0142337 | A1 | 6/2006 | Ikeura et al. |
| 2006/0142816 | A1 | 6/2006 | Fruitman et al. |
| 2006/0142822 | A1 | 6/2006 | Tulgar |
| 2006/0149333 | A1 | 7/2006 | Tanagho et al. |
| 2006/0149337 | A1 | 7/2006 | John |
| 2006/0189453 | A1 | 8/2006 | Leblond |
| 2006/0189839 | A1 | 8/2006 | Laniado et al. |
| 2006/0195153 | A1 | 8/2006 | DiUbaldi et al. |
| 2006/0239482 | A1 | 10/2006 | Hatoum |
| 2006/0241356 | A1 | 10/2006 | Flaherty |
| 2006/0282127 | A1 | 12/2006 | Zealear |
| 2007/0004567 | A1 | 1/2007 | Shetty et al. |
| 2007/0009968 | A1 | 1/2007 | Cunningham et al. |
| 2007/0016097 | A1 | 1/2007 | Farquhar et al. |
| 2007/0016266 | A1 | 1/2007 | Paul, Jr. |
| 2007/0016268 | A1 | 1/2007 | Carter et al. |
| 2007/0016329 | A1 | 1/2007 | Herr et al. |
| 2007/0021513 | A1 | 1/2007 | Agee et al. |
| 2007/0027495 | A1 | 2/2007 | Gerber |
| 2007/0047852 | A1 | 3/2007 | Sharp et al. |
| 2007/0049814 | A1 | 3/2007 | Muccio |
| 2007/0055318 | A1 | 3/2007 | Forsberg et al. |
| 2007/0055337 | A1 | 3/2007 | Tanrisever |
| 2007/0060954 | A1 | 3/2007 | Cameron et al. |
| 2007/0060980 | A1 | 3/2007 | Strother et al. |
| 2007/0067003 | A1 | 3/2007 | Sanchez et al. |
| 2007/0073357 | A1 | 3/2007 | Rooney et al. |
| 2007/0083240 | A1 | 4/2007 | Peterson et al. |
| 2007/0100389 | A1 | 5/2007 | Jaax et al. |
| 2007/0121702 | A1 | 5/2007 | LaGuardia et al. |
| 2007/0121709 | A1 | 5/2007 | Ittogi |
| 2007/0129769 | A1 | 6/2007 | Bourget et al. |
| 2007/0142874 | A1 | 6/2007 | John |
| 2007/0142878 | A1 | 6/2007 | Krulevitch et al. |
| 2007/0150023 | A1 | 6/2007 | Ignagni et al. |
| 2007/0150034 | A1 | 6/2007 | Rooney et al. |
| 2007/0156172 | A1 | 7/2007 | Alvarado |
| 2007/0156179 | A1 | 7/2007 | Karashurov |
| 2007/0156200 | A1 | 7/2007 | Kornet et al. |
| 2007/0168008 | A1 | 7/2007 | Olsen |
| 2007/0179534 | A1 | 8/2007 | Firlik et al. |
| 2007/0179579 | A1 | 8/2007 | Feler et al. |
| 2007/0191709 | A1 | 8/2007 | Swanson |
| 2007/0208381 | A1 | 9/2007 | Hill et al. |
| 2007/0233204 | A1 | 10/2007 | Lima et al. |
| 2007/0250119 | A1 | 10/2007 | Tyler et al. |
| 2007/0255372 | A1 | 11/2007 | Metzler et al. |
| 2007/0265621 | A1 | 11/2007 | Matthis et al. |
| 2007/0265679 | A1 | 11/2007 | Bradley et al. |
| 2007/0265691 | A1 | 11/2007 | Swanson |
| 2007/0276449 | A1 | 11/2007 | Gunter et al. |
| 2007/0276450 | A1 | 11/2007 | Meadows et al. |
| 2007/0282378 | A1 | 12/2007 | Huang et al. |
| 2007/0293910 | A1 | 12/2007 | Strother et al. |
| 2008/0002227 | A1 | 1/2008 | Tsujimoto |
| 2008/0004674 | A1 | 1/2008 | King et al. |
| 2008/0009927 | A1 | 1/2008 | Vilims |
| 2008/0021513 | A1 | 1/2008 | Thacker et al. |
| 2008/0027346 | A1 | 1/2008 | Litt et al. |
| 2008/0046049 | A1 | 2/2008 | Skubitz et al. |
| 2008/0051851 | A1 | 2/2008 | Lin |
| 2008/0071325 | A1 | 3/2008 | Bradley |
| 2008/0077192 | A1 | 3/2008 | Harry et al. |
| 2008/0092911 | A1 | 4/2008 | Schulman et al. |
| 2008/0103579 | A1 | 5/2008 | Gerber |
| 2008/0105185 | A1 | 5/2008 | Kuhlman |
| 2008/0127031 | A1 | 5/2008 | Olsson et al. |
| 2008/0140152 | A1 | 6/2008 | Imran et al. |
| 2008/0140162 | A1 | 6/2008 | Goetz et al. |
| 2008/0140169 | A1 | 6/2008 | Imran |
| 2008/0147143 | A1 | 6/2008 | Popovic et al. |
| 2008/0154329 | A1 | 6/2008 | Pyles et al. |
| 2008/0183097 | A1 | 7/2008 | Leyde et al. |
| 2008/0183224 | A1 | 7/2008 | Barolat |
| 2008/0200749 | A1 | 8/2008 | Zheng et al. |
| 2008/0202940 | A1 | 8/2008 | Jiang et al. |
| 2008/0207985 | A1 | 8/2008 | Farone |
| 2008/0208287 | A1 * | 8/2008 | Palermo ................. A61N 1/323 607/3 |
| 2008/0215113 | A1 | 9/2008 | Pawlowicz |
| 2008/0221653 | A1 | 9/2008 | Agrawal et al. |
| 2008/0224226 | A1 | 9/2008 | Suzuki et al. |
| 2008/0228241 | A1 | 9/2008 | Sachs |
| 2008/0228250 | A1 | 9/2008 | Mironer |
| 2008/0234121 | A1 | 9/2008 | Kim et al. |
| 2008/0234791 | A1 | 9/2008 | Arle et al. |
| 2008/0255582 | A1 | 10/2008 | Harris |
| 2008/0269854 | A1 | 10/2008 | Hegland et al. |
| 2008/0275129 | A1 | 11/2008 | Lundstedt et al. |
| 2008/0279896 | A1 | 11/2008 | Heinen et al. |
| 2008/0287268 | A1 | 11/2008 | Hidler |
| 2008/0294211 | A1 | 11/2008 | Moffitt |
| 2008/0294226 | A1 | 11/2008 | Moffitt et al. |
| 2008/0318733 | A1 | 12/2008 | Osler-Weppenaar |
| 2009/0005844 | A1 | 1/2009 | Swoyer et al. |
| 2009/0012436 | A1 | 1/2009 | Lanfermann et al. |
| 2009/0024186 | A1 | 1/2009 | Brockway |
| 2009/0024997 | A1 | 1/2009 | Kobayashi |
| 2009/0093854 | A1 | 4/2009 | Leung et al. |
| 2009/0112281 | A1 | 4/2009 | Miyazawa et al. |
| 2009/0118365 | A1 | 5/2009 | Benson, III et al. |
| 2009/0131995 | A1 | 5/2009 | Sloan et al. |
| 2009/0157141 | A1 | 6/2009 | Chiao et al. |

(56) References Cited

U.S. PATENT DOCUMENTS

2009/0198305 A1 8/2009 Naroditsky et al.
2009/0204173 A1 8/2009 Fang et al.
2009/0227925 A1 9/2009 Mcbean et al.
2009/0229166 A1 9/2009 Sawrie
2009/0254151 A1 10/2009 Anderson et al.
2009/0270960 A1 10/2009 Zhao et al.
2009/0281529 A1 11/2009 Carriazo
2009/0281599 A1 11/2009 Thacker et al.
2009/0293270 A1 12/2009 Brindley et al.
2009/0299166 A1 12/2009 Nishida et al.
2009/0299167 A1 12/2009 Seymour
2009/0306491 A1 12/2009 Haggers
2009/0312165 A1 12/2009 Rempe
2010/0004715 A1 1/2010 Fahey
2010/0006737 A1 1/2010 Colombo et al.
2010/0008782 A1 1/2010 Danescu et al.
2010/0010646 A1 1/2010 Drew et al.
2010/0016732 A1 1/2010 Wells et al.
2010/0023069 A1 1/2010 Moffitt et al.
2010/0023070 A1 1/2010 Moffitt et al.
2010/0023103 A1 1/2010 Elborno
2010/0029040 A1 2/2010 Nomoto
2010/0042193 A1 2/2010 Slavin
2010/0048358 A1 2/2010 Tchao et al.
2010/0057177 A1 3/2010 Moffitt et al.
2010/0063568 A1 3/2010 Staunton et al.
2010/0070007 A1 3/2010 Parker et al.
2010/0070010 A1 3/2010 Simpson
2010/0087782 A1 4/2010 Ghaffari et al.
2010/0094800 A1 4/2010 Sharp
2010/0114205 A1 5/2010 Donofrio et al.
2010/0114239 A1 5/2010 McDonald et al.
2010/0116526 A1 5/2010 Arora et al.
2010/0125313 A1 5/2010 Lee et al.
2010/0137238 A1 6/2010 Gan et al.
2010/0137938 A1 6/2010 Kishawi et al.
2010/0137943 A1 6/2010 Zhu
2010/0145428 A1 6/2010 Cameron et al.
2010/0152811 A1 6/2010 Flaherty
2010/0166546 A1 7/2010 Mahan et al.
2010/0168820 A1 7/2010 Maniak et al.
2010/0179562 A1 7/2010 Linker et al.
2010/0185253 A1 7/2010 Dimarco et al.
2010/0191307 A1 7/2010 Fang et al.
2010/0198298 A1 8/2010 Glukhovsky et al.
2010/0217355 A1 8/2010 Tass et al.
2010/0217418 A1 8/2010 Fontanot
2010/0228310 A1 9/2010 Shuros et al.
2010/0241121 A1 9/2010 Logan et al.
2010/0241191 A1 9/2010 Testerman et al.
2010/0268299 A1 10/2010 Farone
2010/0274312 A1 10/2010 Alataris et al.
2010/0279606 A1 11/2010 Hillan et al.
2010/0280570 A1 11/2010 Sturm et al.
2010/0298905 A1 11/2010 Simon
2010/0298910 A1 11/2010 Carbunaru et al.
2010/0305660 A1 12/2010 Hegi et al.
2010/0312304 A1 12/2010 York et al.
2010/0318168 A1 12/2010 Bighetti
2010/0324699 A1 12/2010 Herr et al.
2010/0331925 A1 12/2010 Peterson
2011/0006793 A1 1/2011 Peschke et al.
2011/0009919 A1 1/2011 Carbunaru et al.
2011/0016081 A1 1/2011 Basak et al.
2011/0029040 A1 2/2011 Walker et al.
2011/0029044 A1 2/2011 Hyde et al.
2011/0034277 A1 2/2011 Brandes
2011/0034912 A1 2/2011 De Graff et al.
2011/0034977 A1 2/2011 Janik et al.
2011/0040349 A1 2/2011 Graupe
2011/0054567 A1 3/2011 Lane et al.
2011/0054568 A1 3/2011 Lane et al.
2011/0054570 A1 3/2011 Lane
2011/0054579 A1 3/2011 Kumar et al.
2011/0060461 A1 3/2011 Velliste et al.
2011/0077660 A1 3/2011 Janik et al.
2011/0082515 A1 4/2011 Libbus et al.
2011/0084489 A1 4/2011 Kaplan
2011/0093043 A1 4/2011 Torgerson et al.
2011/0112601 A1 5/2011 Meadows et al.
2011/0112611 A1 5/2011 Aghassian
2011/0118815 A1 5/2011 Kuzma et al.
2011/0125203 A1 5/2011 Simon et al.
2011/0130804 A1 6/2011 Lin et al.
2011/0152967 A1 6/2011 Simon et al.
2011/0160810 A1 6/2011 Griffith
2011/0166546 A1 7/2011 Jaax et al.
2011/0184482 A1 7/2011 Eberman et al.
2011/0184488 A1 7/2011 De Ridder
2011/0184489 A1 7/2011 Nicolelis et al.
2011/0201944 A1 8/2011 Higgins et al.
2011/0202107 A1 8/2011 Sunagawa et al.
2011/0208265 A1 8/2011 Erickson et al.
2011/0213266 A1 9/2011 Williams et al.
2011/0218590 A1 9/2011 DeGiorgio et al.
2011/0218594 A1 9/2011 Doran et al.
2011/0224153 A1 9/2011 Levitt et al.
2011/0224665 A1 9/2011 Crosby et al.
2011/0224752 A1 9/2011 Rolston et al.
2011/0224753 A1 9/2011 Palermo et al.
2011/0224755 A1 9/2011 Arie et al.
2011/0224757 A1 9/2011 Zdeblick et al.
2011/0230101 A1 9/2011 Tang et al.
2011/0230701 A1 9/2011 Simon et al.
2011/0230702 A1 9/2011 Honour
2011/0230747 A1 9/2011 Rogers et al.
2011/0230808 A1 9/2011 Lisowski
2011/0231326 A1 9/2011 Marino
2011/0237221 A1 9/2011 Prakash et al.
2011/0237921 A1 9/2011 Askin, III et al.
2011/0245734 A1 10/2011 Wagner et al.
2011/0260126 A1 10/2011 Willis
2011/0270360 A1 11/2011 Harris et al.
2011/0276107 A1 11/2011 Simon et al.
2011/0288609 A1 11/2011 Tehrani et al.
2011/0295100 A1 12/2011 Rolston et al.
2012/0006793 A1 1/2012 Swanson
2012/0011222 A1 1/2012 Yasukawa et al.
2012/0011950 A1 1/2012 Kracke
2012/0013041 A1 1/2012 Cao et al.
2012/0013126 A1 1/2012 Molloy
2012/0016448 A1 1/2012 Lee
2012/0016453 A1 1/2012 Feler et al.
2012/0018249 A1 1/2012 Mehr
2012/0022371 A1 1/2012 Summerton
2012/0022551 A1 1/2012 Staunton et al.
2012/0029528 A1 2/2012 Macdonald et al.
2012/0035684 A1 2/2012 Thompson et al.
2012/0036552 A1 2/2012 Dare et al.
2012/0041518 A1 2/2012 Kim et al.
2012/0052432 A1 3/2012 Matsuura
2012/0053645 A1 3/2012 Ayanoor-Vitikkate et al.
2012/0059432 A1 3/2012 Emborg et al.
2012/0071250 A1 3/2012 O'Neil et al.
2012/0071950 A1 3/2012 Archer
2012/0083709 A1 4/2012 Parker et al.
2012/0101326 A1 4/2012 Simon et al.
2012/0109251 A1 5/2012 Lebedev et al.
2012/0109295 A1 5/2012 Fan
2012/0116476 A1 5/2012 Kothandaraman
2012/0116478 A1 5/2012 Buhlmann et al.
2012/0123223 A1 5/2012 Freeman et al.
2012/0123293 A1 5/2012 Shah et al.
2012/0126392 A1 5/2012 Kalvesten et al.
2012/0136408 A1 5/2012 Grill et al.
2012/0143281 A1 6/2012 Birkill et al.
2012/0161531 A1 6/2012 Kim
2012/0161721 A1 6/2012 Neethimanickam
2012/0165899 A1 6/2012 Gliner
2012/0168397 A1 7/2012 Lim et al.
2012/0172222 A1 7/2012 Artigas Puerto
2012/0172246 A1 7/2012 Nguyen et al.
2012/0172510 A1 7/2012 Esseghir et al.
2012/0172946 A1 7/2012 Altaris et al.

(56) References Cited

U.S. PATENT DOCUMENTS

2012/0179222 A1 7/2012 Jaax et al.
2012/0185020 A1 7/2012 Simon et al.
2012/0197338 A1 8/2012 Su et al.
2012/0203055 A1 8/2012 Pletnev
2012/0203131 A1 8/2012 DiLorenzo
2012/0203246 A1 8/2012 Staunton et al.
2012/0221073 A1 8/2012 Southwell et al.
2012/0232615 A1 9/2012 Barolat et al.
2012/0252380 A1 10/2012 Kawakita
2012/0252874 A1 10/2012 Feinstein et al.
2012/0259380 A1 10/2012 Pyles
2012/0265269 A1 10/2012 Lui
2012/0271315 A1 10/2012 Pianca et al.
2012/0271372 A1 10/2012 Osorio
2012/0277824 A1 11/2012 Li
2012/0277834 A1 11/2012 Mercanzini et al.
2012/0283697 A1 11/2012 Kim et al.
2012/0283797 A1 11/2012 De Ridder
2012/0302821 A1 11/2012 Burnett
2012/0310302 A1 12/2012 Bennett et al.
2012/0310305 A1 12/2012 Kaula et al.
2012/0310315 A1 12/2012 Savage et al.
2012/0330321 A1 12/2012 Johnson et al.
2012/0330391 A1 12/2012 Bradley et al.
2013/0006322 A1 1/2013 Tai
2013/0006793 A1 1/2013 O'Sullivan et al.
2013/0012853 A1 1/2013 Brown
2013/0013041 A1 1/2013 Glukhovsky et al.
2013/0023972 A1 1/2013 Kuzma et al.
2013/0026640 A1 1/2013 Ito et al.
2013/0030312 A1 1/2013 Keel et al.
2013/0030319 A1 1/2013 Hettrick et al.
2013/0030501 A1 1/2013 Feler et al.
2013/0032508 A1 2/2013 Azuma
2013/0035745 A1 2/2013 Ahmed et al.
2013/0041235 A1 2/2013 Rogers et al.
2013/0053734 A1 2/2013 Barriskill et al.
2013/0053922 A1 2/2013 Ahmed et al.
2013/0066392 A1 3/2013 Simon et al.
2013/0066411 A1 3/2013 Thacker et al.
2013/0085317 A1 4/2013 Feinstein
2013/0085361 A1 4/2013 Mercanzini et al.
2013/0096640 A1 4/2013 Possover
2013/0096661 A1 4/2013 Greenberg et al.
2013/0096662 A1 4/2013 Swanson
2013/0110196 A1 5/2013 Alataris et al.
2013/0116604 A1 5/2013 Marilla et al.
2013/0116751 A1 5/2013 Moffitt et al.
2013/0123568 A1 5/2013 Hamilton et al.
2013/0123659 A1 5/2013 Bartol et al.
2013/0138167 A1 5/2013 Bradley et al.
2013/0150915 A1 6/2013 Kane et al.
2013/0154373 A1 6/2013 Lisuwandi et al.
2013/0158444 A1 6/2013 Herr et al.
2013/0165991 A1 6/2013 Kim et al.
2013/0190143 A1 7/2013 Greenhill et al.
2013/0197408 A1 8/2013 Goldfarb et al.
2013/0204324 A1 8/2013 Thacker et al.
2013/0211477 A1 8/2013 Cullen et al.
2013/0226263 A1 8/2013 Kelly et al.
2013/0237948 A1 9/2013 Donders et al.
2013/0245712 A1 9/2013 Simon et al.
2013/0253222 A1 9/2013 Nakao
2013/0253229 A1 9/2013 Sawant et al.
2013/0253299 A1 9/2013 Weber et al.
2013/0253611 A1 9/2013 Lee et al.
2013/0268016 A1 10/2013 Xi et al.
2013/0268020 A1 10/2013 Rosenberg et al.
2013/0268021 A1 10/2013 Moffitt
2013/0268041 A1 10/2013 Schulte et al.
2013/0281890 A1 10/2013 Mishelevich
2013/0289446 A1 10/2013 Stone et al.
2013/0289650 A1 10/2013 Karlsson et al.
2013/0289664 A1 10/2013 Johanek
2013/0289667 A1 10/2013 Wacnik et al.
2013/0296965 A1 11/2013 Mokelke et al.
2013/0303873 A1 11/2013 Voros et al.
2013/0304159 A1 11/2013 Simon et al.
2013/0310211 A1 11/2013 Wilton et al.
2013/0310911 A1 11/2013 Tai et al.
2013/0325081 A1 12/2013 Karst et al.
2013/0325083 A1 12/2013 Bharmi et al.
2013/0345780 A1 12/2013 Tabada et al.
2014/0005753 A1 1/2014 Carbunaru
2014/0031893 A1 1/2014 Walker et al.
2014/0031895 A1 1/2014 Rahimi et al.
2014/0046407 A1 2/2014 Ben-Ezra et al.
2014/0053401 A1 2/2014 Kuzma et al.
2014/0058292 A1 2/2014 Alford et al.
2014/0058490 A1 2/2014 DiMarco
2014/0059499 A1 2/2014 Kim et al.
2014/0066950 A1 3/2014 Macdonald et al.
2014/0067007 A1 3/2014 Drees et al.
2014/0067013 A1 3/2014 Kaula et al.
2014/0067354 A1 3/2014 Kaula et al.
2014/0074190 A1 3/2014 Griffith
2014/0081011 A1 3/2014 Vaught et al.
2014/0081071 A1 3/2014 Simon et al.
2014/0081345 A1 3/2014 Hershey
2014/0087922 A1 3/2014 Bayerlein et al.
2014/0088674 A1 3/2014 Bradley
2014/0100491 A1 4/2014 Hu et al.
2014/0100633 A1 4/2014 Mann et al.
2014/0107397 A1 4/2014 Simon et al.
2014/0107398 A1 4/2014 Simon et al.
2014/0114374 A1 4/2014 Rooney et al.
2014/0114385 A1 4/2014 Nijhuis et al.
2014/0124713 A1 5/2014 Majumdar et al.
2014/0142652 A1 5/2014 Francois et al.
2014/0163640 A1 6/2014 Edgerton et al.
2014/0171961 A1 6/2014 Lacey et al.
2014/0172045 A1 6/2014 Yip et al.
2014/0172055 A1 6/2014 Venancio
2014/0180361 A1 6/2014 Burdick et al.
2014/0200387 A1 7/2014 Ahmed
2014/0201905 A1 7/2014 Glukhovsky
2014/0213842 A1 7/2014 Simon et al.
2014/0213844 A1 7/2014 Pilla et al.
2014/0228905 A1 8/2014 Bolea
2014/0236257 A1 8/2014 Parker et al.
2014/0243923 A1 8/2014 Doan et al.
2014/0257016 A1 9/2014 Ahmed
2014/0277271 A1 9/2014 Chan et al.
2014/0296752 A1 10/2014 Edgerton et al.
2014/0303685 A1 10/2014 Rosenberg et al.
2014/0303901 A1 10/2014 Sadeh
2014/0316484 A1 10/2014 Edgerton et al.
2014/0316503 A1 10/2014 Tai et al.
2014/0324118 A1 10/2014 Simon et al.
2014/0330067 A1 11/2014 Jordan
2014/0330335 A1 11/2014 Errico et al.
2014/0336722 A1 11/2014 Rocon De Lima et al.
2014/0339909 A1 11/2014 Sugawara
2014/0343623 A1 11/2014 Alves et al.
2014/0344740 A1 11/2014 Kaula et al.
2014/0357936 A1 12/2014 Simon et al.
2014/0359521 A1 12/2014 Lin et al.
2014/0371830 A1 12/2014 Howard et al.
2015/0005167 A1 1/2015 Jung et al.
2015/0005840 A1 1/2015 Pal et al.
2015/0012061 A1 1/2015 Chen
2015/0022143 A1 1/2015 Kim
2015/0032187 A1 1/2015 Ranu et al.
2015/0051674 A1 2/2015 Barner et al.
2015/0057717 A1 2/2015 Wu et al.
2015/0065559 A1 3/2015 Feinstein et al.
2015/0066111 A1 3/2015 Blum et al.
2015/0074997 A1 3/2015 Kuzma et al.
2015/0088212 A1 3/2015 De Ridder
2015/0094734 A1 4/2015 Staunton et al.
2015/0094791 A1 4/2015 Edgell et al.
2015/0120634 A1 4/2015 Tateno
2015/0126120 A1 5/2015 Chen
2015/0148878 A1 5/2015 Yoo et al.

(56) References Cited

U.S. PATENT DOCUMENTS

| | | | |
|---|---|---|---|
| 2015/0151114 | A1 | 6/2015 | Black et al. |
| 2015/0151126 | A1 | 6/2015 | Kishawi et al. |
| 2015/0165226 | A1 | 6/2015 | Simon et al. |
| 2015/0174411 | A1 | 6/2015 | Ranu |
| 2015/0182784 | A1 | 7/2015 | Barriskill et al. |
| 2015/0188592 | A1 | 7/2015 | Solondz |
| 2015/0190200 | A1 | 7/2015 | Courtine et al. |
| 2015/0190634 | A1 | 7/2015 | Rezai et al. |
| 2015/0196231 | A1 | 7/2015 | Ziaie et al. |
| 2015/0196241 | A1 | 7/2015 | Yekutieli |
| 2015/0200561 | A1 | 7/2015 | Lee et al. |
| 2015/0217120 | A1 | 8/2015 | Nandra et al. |
| 2015/0224326 | A1 | 8/2015 | Toth et al. |
| 2015/0231326 | A1 | 8/2015 | Milner et al. |
| 2015/0231396 | A1 | 8/2015 | Burdick et al. |
| 2015/0246216 | A1 | 9/2015 | Barker |
| 2015/0265830 | A1 | 9/2015 | Simon et al. |
| 2015/0268845 | A1 | 9/2015 | Endo |
| 2015/0320632 | A1 | 11/2015 | Vallery et al. |
| 2015/0328462 | A1 | 11/2015 | Griffith |
| 2015/0343199 | A1 | 12/2015 | Wechter et al. |
| 2015/0343205 | A1 | 12/2015 | Howard et al. |
| 2016/0001096 | A1 | 1/2016 | Mishelevich |
| 2016/0005538 | A1 | 1/2016 | Koyanagi et al. |
| 2016/0030737 | A1 | 2/2016 | Gerasimenko et al. |
| 2016/0030748 | A1 | 2/2016 | Edgerton et al. |
| 2016/0030750 | A1 | 2/2016 | Bokil et al. |
| 2016/0045727 | A1 | 2/2016 | Rezai et al. |
| 2016/0045731 | A1 | 2/2016 | Simon et al. |
| 2016/0067477 | A1 | 3/2016 | Dubuclet |
| 2016/0074663 | A1 | 3/2016 | De Ridder |
| 2016/0082261 | A1 | 3/2016 | Moffitt et al. |
| 2016/0121109 | A1 | 5/2016 | Edgerton et al. |
| 2016/0121114 | A1 | 5/2016 | Simon et al. |
| 2016/0121116 | A1 | 5/2016 | Simon et al. |
| 2016/0121121 | A1 | 5/2016 | Mashiach |
| 2016/0136477 | A1 | 5/2016 | Bucher et al. |
| 2016/0143588 | A1 | 5/2016 | Hoitink et al. |
| 2016/0144167 | A1 | 5/2016 | Bakker et al. |
| 2016/0144184 | A1 | 5/2016 | Marnfeldt |
| 2016/0157389 | A1 | 6/2016 | Hwang |
| 2016/0166828 | A1 | 6/2016 | Yu |
| 2016/0175586 | A1 | 6/2016 | Edgerton et al. |
| 2016/0197488 | A1 | 7/2016 | Hada et al. |
| 2016/0213918 | A1 | 7/2016 | Howard et al. |
| 2016/0220813 | A1 | 8/2016 | Edgerton et al. |
| 2016/0228706 | A1 | 8/2016 | Hershey et al. |
| 2016/0235977 | A1 | 8/2016 | Lu et al. |
| 2016/0250461 | A1 | 9/2016 | Dubuclet |
| 2016/0263376 | A1 | 9/2016 | Yoo et al. |
| 2016/0271413 | A1 | 9/2016 | Vallejo et al. |
| 2016/0279418 | A1 | 9/2016 | Courtine et al. |
| 2016/0279429 | A1 | 9/2016 | Hershey et al. |
| 2016/0291848 | A1 | 10/2016 | Hall et al. |
| 2016/0310739 | A1 | 10/2016 | Burdick et al. |
| 2016/0339239 | A1 | 11/2016 | Yoo et al. |
| 2016/0367827 | A1 | 12/2016 | Tahmasian |
| 2017/0007320 | A1 | 1/2017 | Levin et al. |
| 2017/0007831 | A1 | 1/2017 | Edgerton et al. |
| 2017/0014620 | A9 | 1/2017 | Staunton et al. |
| 2017/0014622 | A1 | 1/2017 | Bozung et al. |
| 2017/0065814 | A1 | 3/2017 | Howard et al. |
| 2017/0079598 | A1 | 3/2017 | Stolen et al. |
| 2017/0098951 | A1 | 4/2017 | Olgun et al. |
| 2017/0098962 | A1 | 4/2017 | Desrosiers |
| 2017/0118722 | A1 | 4/2017 | Hong et al. |
| 2017/0128729 | A1 | 5/2017 | Netoff et al. |
| 2017/0156662 | A1 | 6/2017 | Goodall et al. |
| 2017/0157389 | A1 | 6/2017 | Tai et al. |
| 2017/0157396 | A1 | 6/2017 | Dixon et al. |
| 2017/0161454 | A1 | 6/2017 | Grill et al. |
| 2017/0165497 | A1 | 6/2017 | Lu |
| 2017/0173326 | A1 | 6/2017 | Bloch et al. |
| 2017/0189686 | A1 | 7/2017 | Steinke et al. |
| 2017/0239486 | A1 | 8/2017 | Suryavanshi |
| 2017/0246450 | A1 | 8/2017 | Liu et al. |
| 2017/0246452 | A1 | 8/2017 | Liu et al. |
| 2017/0266455 | A1 | 9/2017 | Steinke |
| 2017/0274209 | A1 | 9/2017 | Edgerton et al. |
| 2017/0291023 | A1 | 10/2017 | Kuzma et al. |
| 2017/0296837 | A1 | 10/2017 | Jin |
| 2017/0338570 | A1 | 11/2017 | Myers |
| 2017/0348523 | A1 | 12/2017 | Rubehn et al. |
| 2017/0348532 | A1 | 12/2017 | Moffitt et al. |
| 2017/0354819 | A1 | 12/2017 | Bloch et al. |
| 2017/0361093 | A1 | 12/2017 | Yoo et al. |
| 2017/0361115 | A1 | 12/2017 | Aghassian et al. |
| 2018/0008826 | A1 | 1/2018 | Dimarco |
| 2018/0028812 | A1 | 2/2018 | Vallejo et al. |
| 2018/0056078 | A1 | 3/2018 | Kashyap et al. |
| 2018/0083473 | A1 | 3/2018 | Menegoli et al. |
| 2018/0085582 | A1 | 3/2018 | Calle et al. |
| 2018/0085583 | A1 | 3/2018 | Zhang et al. |
| 2018/0093093 | A1 | 4/2018 | Courtine et al. |
| 2018/0104479 | A1 | 4/2018 | Grill et al. |
| 2018/0110992 | A1 | 4/2018 | Parramon et al. |
| 2018/0117334 | A1 | 5/2018 | Jung |
| 2018/0125416 | A1 | 5/2018 | Schwarz et al. |
| 2018/0125419 | A1 | 5/2018 | Yun et al. |
| 2018/0126154 | A1 | 5/2018 | Dubuclet |
| 2018/0126155 | A1 | 5/2018 | Mclaughlin et al. |
| 2018/0133480 | A1 | 5/2018 | Annoni et al. |
| 2018/0133481 | A1 | 5/2018 | Von Zitzewitz et al. |
| 2018/0153474 | A1 | 6/2018 | Aeschlimann et al. |
| 2018/0178008 | A1 | 6/2018 | Bouton et al. |
| 2018/0185632 | A1 | 7/2018 | Staunton et al. |
| 2018/0185642 | A1 | 7/2018 | Lu |
| 2018/0185648 | A1 | 7/2018 | Nandra et al. |
| 2018/0193655 | A1 | 7/2018 | Zhang et al. |
| 2018/0214694 | A1 | 8/2018 | Parramon |
| 2018/0221620 | A1 | 8/2018 | Metzger |
| 2018/0221651 | A1 | 8/2018 | Chang et al. |
| 2018/0228421 | A1 | 8/2018 | Saab |
| 2018/0229037 | A1 | 8/2018 | Edgerton et al. |
| 2018/0229038 | A1 | 8/2018 | Burdick et al. |
| 2018/0236240 | A1 | 8/2018 | Harkema et al. |
| 2018/0256906 | A1 | 9/2018 | Pivonka et al. |
| 2018/0272125 | A1 | 9/2018 | Sandhu |
| 2018/0272132 | A1 | 9/2018 | Subbaroyan et al. |
| 2018/0280693 | A1 | 10/2018 | Edgerton et al. |
| 2018/0280706 | A1 | 10/2018 | Maile et al. |
| 2018/0289971 | A1 | 10/2018 | Yeh et al. |
| 2018/0294547 | A1 | 10/2018 | Park et al. |
| 2018/0318576 | A1 | 11/2018 | Bozung et al. |
| 2018/0326220 | A1 | 11/2018 | Kaula et al. |
| 2018/0337547 | A1 | 11/2018 | Menegoli et al. |
| 2018/0353755 | A1 | 12/2018 | Edgerton et al. |
| 2018/0361146 | A1 | 12/2018 | Gerasimenko et al. |
| 2018/0367187 | A1 | 12/2018 | Mcfarthing |
| 2018/0369574 | A1 | 12/2018 | Dubuclet et al. |
| 2018/0369575 | A1 | 12/2018 | Dubuclet et al. |
| 2018/0369576 | A1 | 12/2018 | Dubuclet et al. |
| 2019/0001122 | A1 | 1/2019 | Ganty et al. |
| 2019/0001139 | A1 | 1/2019 | Mishra et al. |
| 2019/0009094 | A1 | 1/2019 | Zhang et al. |
| 2019/0017983 | A1 | 1/2019 | Smith |
| 2019/0022371 | A1 | 1/2019 | Chang et al. |
| 2019/0027257 | A1 | 1/2019 | Ghogawala |
| 2019/0033622 | A1 | 1/2019 | Olgun et al. |
| 2019/0160294 | A1 | 5/2019 | Peterson et al. |
| 2019/0167980 | A1 | 6/2019 | Peterson |
| 2019/0167987 | A1 | 6/2019 | Lu et al. |
| 2019/0192852 | A1 | 6/2019 | De Ridder |
| 2019/0192864 | A1 | 6/2019 | Koop et al. |
| 2019/0240468 | A1 | 8/2019 | Yun et al. |
| 2019/0247650 | A1 | 8/2019 | Tran |
| 2019/0262609 | A1 | 8/2019 | Brill et al. |
| 2019/0269917 | A1 | 9/2019 | Courtine et al. |
| 2019/0299006 | A1 | 10/2019 | Marnfeldt |
| 2019/0321639 | A1 | 10/2019 | Rao et al. |
| 2019/0336760 | A1 | 11/2019 | Shah |
| 2019/0344070 | A1 | 11/2019 | Molnar et al. |
| 2019/0344075 | A1 | 11/2019 | Bloch et al. |
| 2019/0358454 | A1 | 11/2019 | Lin et al. |

(56) References Cited

U.S. PATENT DOCUMENTS

| | | | |
|---|---|---|---|
| 2019/0374776 | A1 | 12/2019 | Mishra et al. |
| 2019/0374777 | A1 | 12/2019 | Burdick et al. |
| 2019/0381313 | A1 | 12/2019 | Lu |
| 2019/0381328 | A1 | 12/2019 | Wechter et al. |
| 2019/0381382 | A1 | 12/2019 | Wu |
| 2020/0009385 | A1 | 1/2020 | Shah |
| 2020/0060602 | A1 | 2/2020 | Wagner et al. |
| 2020/0061378 | A1 | 2/2020 | Ganguly et al. |
| 2020/0086116 | A1 | 3/2020 | Formento et al. |
| 2020/0121544 | A1 | 4/2020 | George et al. |
| 2020/0139126 | A1 | 5/2020 | Napadow et al. |
| 2020/0144846 | A1 | 5/2020 | Shin |
| 2020/0147382 | A1 | 5/2020 | Caban et al. |
| 2020/0155019 | A1 | 5/2020 | Esteller et al. |
| 2020/0155865 | A1 | 5/2020 | Lu |
| 2020/0228901 | A1 | 7/2020 | Baek |
| 2020/0360697 | A1 | 11/2020 | Paoles et al. |
| 2020/0398068 | A1 | 12/2020 | Agnihotri et al. |
| 2021/0069052 | A1 | 3/2021 | Burke |
| 2021/0093865 | A1 | 4/2021 | Vallejo et al. |
| 2021/0121692 | A1 | 4/2021 | Edgerton et al. |
| 2021/0153942 | A1 | 5/2021 | Scheltienne et al. |
| 2021/0154481 | A1 | 5/2021 | Scheltienne et al. |
| 2021/0170177 | A1 | 6/2021 | Minassian et al. |
| 2021/0170178 | A1 | 6/2021 | Wagner et al. |
| 2021/0187278 | A1 | 6/2021 | Lu |
| 2021/0213292 | A1 | 7/2021 | Minassian et al. |
| 2021/0236837 | A1 | 8/2021 | Lu |
| 2021/0275810 | A1 | 9/2021 | Caban |
| 2021/0290955 | A1 | 9/2021 | Brouns et al. |
| 2021/0299441 | A1 | 9/2021 | Edgerton et al. |
| 2021/0378991 | A1 | 12/2021 | Lu |
| 2021/0402186 | A1 | 12/2021 | Edgerton et al. |
| 2022/0016420 | A1 | 1/2022 | Lo et al. |
| 2022/0111208 | A1 | 4/2022 | Phillips et al. |
| 2022/0125374 | A1 | 4/2022 | Courtine et al. |
| 2022/0134108 | A1 | 5/2022 | Dinsmoor et al. |
| 2022/0143407 | A1 | 5/2022 | Zhuang et al. |
| 2022/0161042 | A1 | 5/2022 | Lu |
| 2022/0176130 | A1 | 6/2022 | Wu et al. |
| 2022/0184386 | A1 | 6/2022 | Courtine et al. |
| 2022/0233848 | A1 | 7/2022 | Gad et al. |
| 2022/0313993 | A1 | 10/2022 | Gerasimenko et al. |
| 2022/0409899 | A1 | 12/2022 | Ganty et al. |
| 2023/0045403 | A1 | 2/2023 | Robison et al. |
| 2023/0053053 | A1 | 2/2023 | Delattre et al. |
| 2023/0186201 | A1 | 6/2023 | Cella et al. |
| 2023/0281527 | A1 | 9/2023 | Cella et al. |
| 2024/0001116 | A1 | 1/2024 | Edgerton et al. |
| 2024/0050746 | A1 | 2/2024 | Angeli et al. |
| 2024/0335666 | A1 | 10/2024 | Murphy |
| 2024/0374541 | A1 | 11/2024 | Lu et al. |
| 2024/0424291 | A1 | 12/2024 | Ganty et al. |
| 2024/0424302 | A1 | 12/2024 | Dumeny |
| 2025/0025689 | A1 | 1/2025 | Lo et al. |
| 2025/0032799 | A1 | 1/2025 | Weijand et al. |

FOREIGN PATENT DOCUMENTS

| | | | |
|---|---|---|---|
| CA | 2649663 | A1 | 11/2007 |
| CA | 2 823 592 | A1 | 7/2012 |
| CA | 2 856 202 | A1 | 5/2013 |
| CA | 2 864 473 | A1 | 5/2013 |
| CA | 3034123 | | 2/2018 |
| CN | 101227940 | A | 7/2008 |
| CN | 101822223 | | 9/2010 |
| CN | 103263727 | A | 8/2013 |
| CN | 104307098 | A | 1/2015 |
| DE | 3830429 | | 3/1990 |
| DE | 202007015508 | | 3/2008 |
| EP | 0034145 | | 8/1981 |
| EP | 0236976 | | 9/1987 |
| EP | 0630987 | A1 | 12/1994 |
| EP | 1127907 | | 8/2001 |
| EP | 1303332 | | 4/2003 |
| EP | 1575665 | | 9/2005 |
| EP | 1675648 | | 7/2006 |
| EP | 1680182 | | 7/2006 |
| EP | 2130326 | A1 | 12/2009 |
| EP | 2141851 | A2 | 1/2010 |
| EP | 2160127 | A1 | 3/2010 |
| EP | 2178319 | A1 | 4/2010 |
| EP | 2192897 | A1 | 6/2010 |
| EP | 2226114 | A1 | 9/2010 |
| EP | 2243510 | | 10/2010 |
| EP | 2258496 | A1 | 12/2010 |
| EP | 2361631 | A1 | 8/2011 |
| EP | 2368401 | A1 | 9/2011 |
| EP | 2387467 | A1 | 11/2011 |
| EP | 2396995 | A1 | 12/2011 |
| EP | 2397788 | A1 | 12/2011 |
| EP | 2445990 | A2 | 5/2012 |
| EP | 2471518 | A2 | 7/2012 |
| EP | 2475283 | A1 | 7/2012 |
| EP | 2486897 | A2 | 8/2012 |
| EP | 2626051 | A1 | 8/2013 |
| EP | 2628502 | A1 | 8/2013 |
| EP | 2661307 | A2 | 11/2013 |
| EP | 2665514 | | 11/2013 |
| EP | 2688642 | A2 | 1/2014 |
| EP | 2810689 | A1 | 12/2014 |
| EP | 2810690 | A1 | 12/2014 |
| EP | 2868323 | | 5/2015 |
| EP | 2868343 | A1 | 5/2015 |
| EP | 2966422 | A1 | 1/2016 |
| EP | 2968940 | A1 | 1/2016 |
| EP | 3184145 | A1 | 6/2017 |
| EP | 3269424 | | 1/2018 |
| EP | 3323468 | A1 | 5/2018 |
| EP | 3328481 | A1 | 6/2018 |
| EP | 3381506 | | 10/2018 |
| EP | 3421081 | | 1/2019 |
| EP | 3285855 | | 6/2019 |
| EP | 3495019 | | 6/2019 |
| EP | 3527258 | A1 | 8/2019 |
| EP | 3969100 | | 7/2023 |
| JP | H03-26620 | A | 2/1991 |
| JP | 3184145 | B2 | 7/2001 |
| JP | 2002517283 | A | 6/2002 |
| JP | 2002200178 | A | 7/2002 |
| JP | 2004065529 | A | 3/2004 |
| JP | 2007-526798 | A | 9/2007 |
| JP | 2008067917 | A | 3/2008 |
| JP | 2008-543429 | A | 12/2008 |
| JP | 2009512516 | | 3/2009 |
| JP | 2011502586 | | 1/2011 |
| JP | 2011504112 | | 2/2011 |
| JP | 2012515060 | | 7/2012 |
| JP | 2013508119 | | 3/2013 |
| JP | 2014513562 | | 6/2014 |
| JP | 2014514043 | A | 6/2014 |
| JP | 2016506255 | A | 3/2016 |
| JP | 6132856 | B2 | 5/2017 |
| JP | 2017104685 | A | 6/2017 |
| JP | 2017523868 | | 8/2017 |
| JP | 2017525509 | A | 9/2017 |
| JP | 2018524113 | A | 8/2018 |
| KR | 101573840 | | 12/2015 |
| RU | 2130326 | C1 | 5/1999 |
| RU | 2141851 | C1 | 11/1999 |
| RU | 2160127 | C1 | 12/2000 |
| RU | 2178319 | C2 | 1/2002 |
| RU | 2192897 | C2 | 11/2002 |
| RU | 2193441 | | 11/2002 |
| RU | 2001102533 | | 11/2002 |
| RU | 2226114 | C1 | 3/2004 |
| RU | 2258496 | C2 | 8/2005 |
| RU | 2361631 | C2 | 7/2009 |
| RU | 2368401 | C1 | 9/2009 |
| RU | 2387467 | C1 | 4/2010 |
| RU | 2396995 | C2 | 8/2010 |
| RU | 2397788 | C2 | 8/2010 |
| RU | 2445990 | C1 | 3/2012 |
| RU | 2471518 | C2 | 1/2013 |

(56) References Cited

FOREIGN PATENT DOCUMENTS

| | | | |
|---|---|---|---|
| RU | 2475283 | C2 | 2/2013 |
| RU | 2661307 | C1 | 7/2018 |
| WO | WO-8100458 | | 2/1981 |
| WO | WO-9409808 | | 5/1994 |
| WO | WO 97/047357 | A1 | 12/1997 |
| WO | WO-9908749 | | 2/1999 |
| WO | WO-0019912 | | 4/2000 |
| WO | WO-0209808 | | 2/2002 |
| WO | WO-0234331 | A2 | 5/2002 |
| WO | WO-02092165 | A1 | 11/2002 |
| WO | WO-03005887 | A2 | 1/2003 |
| WO | WO 03/026735 | A2 | 4/2003 |
| WO | WO 03/092795 | A1 | 11/2003 |
| WO | WO-2003094749 | | 11/2003 |
| WO | WO 2004/087116 | A2 | 10/2004 |
| WO | WO-2005002663 | A2 | 1/2005 |
| WO | WO 2005/051306 | A2 | 6/2005 |
| WO | WO 2005/065768 | A1 | 7/2005 |
| WO | WO 2005/087307 | A2 | 9/2005 |
| WO | WO-2006026850 | | 3/2006 |
| WO | WO 2006/138069 | A1 | 12/2006 |
| WO | WO-2006135751 | A2 | 12/2006 |
| WO | WO 2007/007058 | A1 | 1/2007 |
| WO | WO-2007007057 | | 1/2007 |
| WO | WO 2007/012114 | A1 | 2/2007 |
| WO | WO-2007047852 | A2 | 4/2007 |
| WO | WO-2007057508 | | 5/2007 |
| WO | WO-2007081764 | A2 | 7/2007 |
| WO | WO 2007/107831 | A2 | 9/2007 |
| WO | WO-2008075294 | A1 | 6/2008 |
| WO | WO-2008092785 | | 8/2008 |
| WO | WO 2008/109862 | A1 | 9/2008 |
| WO | WO-2008070807 | A3 | 9/2008 |
| WO | WO 2008/121891 | A1 | 10/2008 |
| WO | WO 2009/042217 | A1 | 4/2009 |
| WO | WO 2009/111142 | A2 | 9/2009 |
| WO | WO-2010021977 | A1 | 2/2010 |
| WO | WO 2010/055421 | A1 | 5/2010 |
| WO | WO-2010083308 | | 7/2010 |
| WO | WO 2010/114998 | A1 | 10/2010 |
| WO | WO 2010/124128 | A1 | 10/2010 |
| WO | WO-2011005607 | A1 | 1/2011 |
| WO | WO-2011008459 | | 1/2011 |
| WO | WO-2011136875 | A1 | 11/2011 |
| WO | WO-2012050200 | A1 | 4/2012 |
| WO | WO-2012075195 | A1 | 6/2012 |
| WO | WO-2012080964 | A1 | 6/2012 |
| WO | WO 2012/094346 | A2 | 7/2012 |
| WO | WO 2012/100260 | A2 | 7/2012 |
| WO | WO-2012103519 | | 8/2012 |
| WO | WO 2012/129574 | A2 | 9/2012 |
| WO | WO-2013049658 | | 4/2013 |
| WO | WO 2013/071307 | A1 | 5/2013 |
| WO | WO 2013/071309 | A1 | 5/2013 |
| WO | WO-2013069004 | | 5/2013 |
| WO | WO-2013117750 | | 8/2013 |
| WO | WO-2013152124 | A1 | 10/2013 |
| WO | WO 2013/188965 | A1 | 12/2013 |
| WO | WO-2013179230 | | 12/2013 |
| WO | WO-2014005075 | A1 | 1/2014 |
| WO | WO-2014031142 | A1 | 2/2014 |
| WO | WO-2014089299 | A2 | 6/2014 |
| WO | WO 2014/144785 | A1 | 9/2014 |
| WO | WO-2014149895 | A1 | 9/2014 |
| WO | WO-2014205356 | A2 | 12/2014 |
| WO | WO-2014209877 | A1 | 12/2014 |
| WO | WO-2015000800 | A1 | 1/2015 |
| WO | WO 2015/048563 | A2 | 4/2015 |
| WO | WO-2015063127 | A1 | 5/2015 |
| WO | WO-2015106286 | A1 | 7/2015 |
| WO | WO-2015172894 | | 11/2015 |
| WO | WO-2016005367 | | 1/2016 |
| WO | WO 2016/029159 | A2 | 2/2016 |
| WO | WO-2016025913 | | 2/2016 |
| WO | WO 2016/033369 | A1 | 3/2016 |
| WO | WO 2016/033372 | A1 | 3/2016 |
| WO | WO-2016064761 | A1 | 4/2016 |
| WO | WO-2016110804 | A1 | 7/2016 |
| WO | WO-2016112398 | A1 | 7/2016 |
| WO | WO-2016172239 | A1 | 10/2016 |
| WO | WO 2017/011410 | A1 | 1/2017 |
| WO | WO-2017005661 | | 1/2017 |
| WO | WO 2017/024276 | A1 | 2/2017 |
| WO | WO 2017/035512 | A1 | 3/2017 |
| WO | WO 2017/044904 | A1 | 3/2017 |
| WO | WO-2017058913 | A1 | 4/2017 |
| WO | WO-2017062508 | A1 | 4/2017 |
| WO | WO-2017117450 | A1 | 7/2017 |
| WO | WO-2017146659 | A1 | 8/2017 |
| WO | WO-2017188965 | | 11/2017 |
| WO | WO-2018033591 | | 2/2018 |
| WO | WO-2018039296 | A2 | 3/2018 |
| WO | WO-2018039458 | | 3/2018 |
| WO | WO-2018063879 | | 4/2018 |
| WO | WO-2018093765 | | 5/2018 |
| WO | WO 2018/106843 | A1 | 6/2018 |
| WO | WO 2018/140531 | A1 | 8/2018 |
| WO | WO-2018148844 | | 8/2018 |
| WO | WO 2018/217791 | A1 | 11/2018 |
| WO | WO-2019211314 | A1 | 11/2019 |
| WO | WO 2020/041502 | A1 | 2/2020 |
| WO | WO 2020/041633 | A1 | 2/2020 |
| WO | WO-2020028088 | | 2/2020 |
| WO | WO 2020/236946 | A1 | 11/2020 |
| WO | WO-2022221442 | | 10/2022 |

OTHER PUBLICATIONS

US Final Office Action dated Sep. 21, 2015 issued in U.S. Appl. No. 14/355,812 [UCLAP080US].

US Notice of Allowance dated Apr. 13, 2016 issued in U.S. Appl. No. 14/355,812 [UCLAP080US].

US Office Action dated Oct. 18, 2016 issued in U.S. Appl. No. 15/208,529 [UCLAP080C1US].

US Final Office Action dated Jul. 13, 2017 issued in U.S. Appl. No. 15/208,529 [UCLAP080C1US].

US Office Action dated Jul. 27, 2018 issued in U.S. Appl. No. 15/208,529 [UCLAP080C1US].

US Final Office Action dated Apr. 19, 2019 issued in U.S. Appl. No. 15/208,529 [UCLAP080C1US].

US Office Action dated Oct. 28, 2019 issued in U.S. Appl. No. 15/208,529 [UCLAP080C1US].

US Notice of Allowance dated Jun. 17, 2020 issued in U.S. Appl. No. 15/208,529 [UCLAP080C1US].

US Office Action dated Oct. 3, 2017 issued in U.S. Appl. No. 15/025,201 [UCLAP114US].

US Notice of Allowance dated Aug. 1, 2018 issued in U.S. Appl. No. 15/025,201 [UCLAP114US].

US Office Action dated Apr. 10, 2020 issued in U.S. Appl. No. 16/200,467 [UCLAP114C1US].

US Office Action dated Nov. 24, 2020 issued in U.S. Appl. No. 16/200,467 [UCLAP114C1US].

US Notice of Allowance dated May 19, 2021 issued in U.S. Appl. No. 16/200,467 [UCLAP114C1US].

US Office Action dated Jul. 13, 2016 issued in U.S. Appl. No. 14/775,618 [UCLAP115US].

US Final Office Action dated Apr. 25, 2017 issued in U.S. Appl. No. 14/775,618 [UCLAP115US].

US Notice of Allowance dated Jan. 18, 2018 issued in U.S. Appl. No. 14/775,618 [UCLAP115US].

US Office Action dated Jan. 8, 2020 issued in U.S. Appl. No. 15/975,678 [UCLAP115C1US].

US Final Office Action dated Jul. 29, 2020 issued in U.S. Appl. No. 15/975,678 [UCLAP115C1US].

US Office Action dated Feb. 10, 2021 issued in U.S. Appl. No. 15/975,678 [UCLAP115C1US].

US Final Office Action dated Jul. 20, 2021 issued in U.S. Appl. No. 15/975,678 [UCLAP115C1US].

US Office Action dated Oct. 31, 2019 issued in U.S. Appl. No. 15/750,499 [UCLAP131US].

(56) References Cited

OTHER PUBLICATIONS

US Final Office Action dated Aug. 6, 2020 issued in U.S. Appl. No. 15/750,499 [UCLAP131US].
US Office Action dated Aug. 6, 2021 issued in U.S. Appl. No. 15/750,499 [UCLAP131US].
US Office Action dated Jul. 22, 2019 issued in U.S. Appl. No. 15/506,696 [UCLAP132US].
US Notice of Allowance dated May 4, 2020 issued in U.S. Appl. No. 15/506,696 [UCLAP132US].
US Office Action dated Jun. 4, 2019 issued in U.S. Appl. No. 15/505,053 [UCLAP133US].
US Notice of Allowance dated Feb. 13, 2020 issued in U.S. Appl. No. 15/505,053 [UCLAP133US].
US 2nd Notice of Allowance dated Jun. 4, 2020 issued in U.S. Appl. No. 15/505,053 [UCLAP133US].
US Office Action dated Apr. 7, 2020 issued in U.S. Appl. No. 15/740,323 [UCLAP135US].
US Final Office Action dated Nov. 20, 2020 issued in U.S. Appl. No. 15/740,323 [UCLAP135US].
US Office Action dated Mar. 29, 2021 issued in U.S. Appl. No. 15/740,323 [UCLAP135US].
US Office Action dated Apr. 17, 2019 issued in U.S. Appl. No. 15/344,381 [UCLAP139US].
US Final Office Action dated Dec 30, 2019 issued in U.S. Appl. No. 15/344,381 [UCLAP139US].
US Office Action dated Aug. 4, 2020 issued in U.S. Appl. No. 15/344,381 [UCLAP139US].
US Notice of Allowance dated Apr. 27, 2021 issued in U.S. Appl. No. 15/344,381 [UCLAP139US].
US Office Action dated Nov. 13, 2020 issued in U.S. Appl. No. 15/753,963 [UCLAP150US].
US Final Office Action dated Jul. 16, 2021 issued in U.S. Appl. No. 15/753,963 [UCLAP150US].
US Office Action dated May 12, 2021 issued in U.S. Appl. No. 16/615,765 [UCLAP183US].
PCT International Search Report dated Jul. 30, 2012 issued in PCT/US2012/020112.
PCT International Preliminary Report on Patentability and Written Opinion dated Jul. 10, 2013 issued in PCT/US2012/020112.
PCT International Search Report and Written Opinion dated Mar. 19, 2013 issued in PCT/US2012/064878 [UCLAP080WO].
PCT International Preliminary Report on Patentability dated May 22, 2014 issued in PCT/US2012/064878 [UCLAP080WO].
Australian Patent Examination Report No. 1 dated Jul. 11, 2016 issued in AU 2012334926 [UCLAP080AU].
Canadian Office Action dated Aug. 31, 2018 issued in CA 2,864,473 [UCLAP080CA].
Canadian Office Action dated Jul. 30, 2019 issued in CA 2,864,473 [UCLAP080CA].
Canadian Office Action dated Aug. 14, 2020 issued in CA 2,864,473 [UCLAP080CA].
European Communication pursuant to Rule 114(2) EPC regarding observations by a third party dated Mar. 27, 2015 issued in EP 12 847 885.6 [UCLAP080EP].
European Extended Search Report dated May 6, 2015 issued in EP 12 847 885.6 [UCLAP080EP].
European Office Action dated Apr. 15, 2016 issued in EP 12 847 885.6 [UCLAP080EP].
European Reply to Communication of Apr. 15, 2016 dated Oct. 24, 2016 in EP 12 847 885.6 [UCLAP080EP].
European Second Office Action dated Feb. 16, 2017 issued in EP 12 847 885.6 [UCLAP080EP].
PCT Declaration of Non-Establishment of International Search Report and Written Opinion dated Dec 24, 2014 issued in PCT/US2014/057886 [UCLAP114WO].
PCT International Preliminary Report on Patentability and Written Opinion dated Apr. 7, 2016 issued in PCT/US2014/057886 [UCLAP114WO].
Australian Examination report No. 1 dated Jan. 11, 2019 issued in AU 2014324660 [UCLAP114AU].
Australian Examination report No. 2 dated Nov. 7, 2019 issued in AU 2014324660 [UCLAP114AU].
Australian Examination report No. 3 dated Jan. 6, 2020 issued in AU 2014324660 [UCLAP114AU].
Australian Examination report No. 1 dated Dec 21, 2020 issued in AU 2020200152 [UCLAP114AUD1].
Canadian Office Action dated Nov. 27, 2020 issued in CA 2,925,754 [UCLAP114CA].
European Extended Search Report dated May 10, 2017 issued in EP 14849355.4 [UCLAP114EP].
European Office Action dated Jul. 20, 2018 issued in EP 14849355.4 [UCLAP114EP].
European Extended Search Report dated Jan. 22, 2021 issued in EP 20175385.2 [UCLAP114EPD1].
PCT International Search Report and Written Opinion dated Aug. 6, 2014 issued in PCT/US2014/029340 [UCLAP115WO].
PCT International Preliminary Report on Patentability dated Sep. 24, 2015 issued in PCT/US2014/029340 [UCLAP115WO].
Australian Patent Examination Report No. 1 dated May 11, 2018 issued in AU 2014228794 [UCLAP115AU].
Australian Patent Examination Report No. 1 dated Jan. 6, 2020 issued in AU 2019206059 [UCLAP115AUD1].
Canadian Office Action dated May 7, 2020 issued in CA 2,906,779 [UCLAP115CA].
Canadian 2nd Office Action dated Apr. 9, 2021 issued in CA 2,906,779 [UCLAP115CA].
European Extended Search Report dated Nov. 8, 2016 issued in EP 14765477.6 [UCLAP115EP].
European Office Action dated Nov. 14, 2018 issued in EP 14765477.6 [UCLAP115EP].
European Office Action dated Sep. 27, 2019 issued in EP 14765477.6 [UCLAP115EP].
European Extended Search Report dated Aug. 17, 2021 issued in EP 21166801.7 [UCLAP115EPD1].
PCT International Search Report and Written Opinion dated Dec. 5, 2016 issued in PCT/US2016/045898 [UCLAP131WO].
PCT International Preliminary Report on Patentability and Written Opinion dated Feb. 15, 2018 issued in PCT/US2016/045898 [UCLAP131WO].
Chinese First Office Action dated Jan. 6, 2021 issued in CN 201680058067.8 [UCLAP131CN].
European Extended Search Report dated Dec. 13, 2018 issued in EP 16833973.7 [UCLAP131EP].
PCT International Search Report and Written Opinion dated Dec. 8, 2015 issued in PCT/US2015/047268 [UCLAP132WO].
PCT International Preliminary Report on Patentability and Written Opinion datedFeb. 28, 2017 issued in PCT/US2015/047268 [UCLAP132WO].
Australian Patent Examination Report No. 1 dated Jul. 18, 2019 issued in AU 2015308779 [UCLAP132AU].
Australian Patent Examination Report No. 2 dated May 20, 2020 issued in AU 2015308779 [UCLAP132AU].
European Extended Search Report dated Mar. 1, 2018 issued in EP 15836927.2 [UCLAP132EP].
European Extended Search Report dated Apr. 21, 2020 issued in EP 19201998.2 [UCLAP132EPD1].
PCT International Search Report and Written Opinion dated Dec. 3, 2015 issued in PCT/US2015/047272 [UCLAP132AWO].
PCT International Preliminary Report on Patentability and Written Opinion datedFeb. 28, 2017 issued in PCT/US2015/047272 [UCLAP132AWO].
PCT Declaration of Non-Establishment of International Search Report and Written Opinion dated Dec. 1, 2015 issued in PCT/US2015/046378 [UCLAP133WO].
PCT International Preliminary Report on Patentability and Written Opinion dated Feb. 21, 2017 issued in PCT/US2015/046378 [UCLAP133WO].
Australian Patent Examination Report No. 1 dated Jun. 14, 2019 issued in AU 2015305237 [UCLAP133AU].
Australian Patent Examination Report No. 2 dated Apr. 17, 2020 issued in AU 2015305237 [UCLAP133AU].
European Extended Search Report dated Apr. 4, 2018 issued in EP 15834593.4 [UCLAP133EP].

(56) References Cited

OTHER PUBLICATIONS

European Office Action dated Jul. 17, 2019 issued in EP 15834593.4 [UCLAP133EP].
European Office Action dated Jul. 30, 2020 issued in EP 15834593.4 [UCLAP133EP].
PCT International Search Report and Written Opinion dated Sep. 12, 2016 issued in PCT/US2016/041802 [UCLAP135WO].
PCT International Preliminary Report on Patentability and Written Opinion dated Jan. 25, 2018 issued in PCT/US2016/041802 [UCLAP135WO].
European Extended Search Report dated Feb. 19, 2019 issued in EP 16825005.8 [UCLAP135EP].
Japanese Office Action dated Jul. 13, 2020 issued in JP 2018-501208 [UCLAP135JP].
Japanese 2nd Office Action dated Mar. 22, 2021 issued in JP 2018-501208 [UCLAP135JP].
PCT International Search Report and Written Opinion dated Dec. 5, 2016 issued in PCT/US2016/049129 [UCLAP150WO].
PCT International Preliminary Report on Patentability and Written Opinion dated Mar. 8, 2018 issued in PCT/US2016/049129 [UCLAP150WO].
PCT International Search Report and Written Opinion dated Mar. 12, 2018 issued in PCT/US2018/015098 [UCLAP181WO].
PCT International Preliminary Report on Patentability and Written Opinion dated Jul. 30, 2019 issued in PCT/US2018/015098 [UCLAP181WO].
European Extended Search Report dated Sep. 7, 2020 issued in EP 18744685.1 [UCLAP181EP].
PCT International Search Report and Written Opinion dated Aug. 31, 2018 issued in PCT/US2018/033942 [UCLAP183WO].
PCT International Preliminary Report on Patentability and Written Opinion dated Nov. 26, 2019 issued in PCT/US2018/033942 [UCLAP183WO].
PCT International Search Report and Written Opinion dated Nov. 14, 2019 issued in PCT/US2019/047777 [UCLAP197WO].
PCT International Preliminary Report on Patentability and Written Opinion dated Feb. 23, 2021 issued in PCT/US2019/047777 [UCLAP197WO].
PCT International Search Report and Written Opinion dated Nov. 21, 2019 issued in PCT/US2019/047551 [UCLAP206WO].
PCT International Preliminary Report on Patentability and Written Opinion dated Feb. 23, 2021 issued in PCT/US2019/047551 [UCLAP206WO].
PCT International Search Report and Written Opinion dated Oct. 14, 2020 issued in PCT/US2020/033830 [UCLAP211WO].
PCT International Search Report dated Mar. 19, 2013 issued in PCT/US2012/064874 [1958711.2WO].
PCT International Search Report dated Sep. 3, 2012 issued in PCT/US2012/022257 [68243-031WO1].
PCT International Search Report dated Oct. 31, 2012 issued in PCT/US2012/030624 [68243-031WO2].
Andersson, et al., (2003) "CNS Involvement in Overactive Bladder." *Drugs*, 63(23): 2595-2611.
Angeli et al. (2014) "Altering spinal cord excitability enables voluntary movements after chronic complete paralysis in humans" *Brain* 137: 1394-1409.
Courtine, Grégoire et al. (2007) "Modulation of multisegmental monosynaptic responses in a variety of leg muscles during walking and running in humans," *J Physiol.* 582.3:1125-1139.
Danner S.M., Hofstoetter U.S., Ladenbauer J., Rattay F, and Minassian K. (Mar. 2011) "Can the human lumbar posterior columns be stimulated by transcutaneous spinal cord stimulation? A modeling study" *Europe PMC Funders Author Manuscripts, Artif Organs* 35(3):257-262, 12 pp.
DeSantana et al. (Dec. 2008) "Effectiveness of Transcutaneous Electrical Nerve Stimulation for Treatment of Hyperalgesia and Pain," *Curr Rheumatol Rep.* 10(6):492-499, 12 pp.
Drummond, et al. (1996) "Thoracic impedance used for measuring chest wall movement in postoperative patients," *British Journal of Anaesthesia*, 77: 327-332.
Dubinsky, Richard M. and Miyasaki, Janis, "Assessment: Efficacy of transcutaneous electric nerve stimulation in the treatment of pain in neurologic disorders (an evidence-based review)," Report of the Therapeutics and Technology Assessment Subcommittee of the American Academy of Neurology, (2010) *Neurology*, 74:173-176.
Edgerton and Harkema (2011) "Epidural stimulation of the spinal cord in spinal cord injury: current status and future challenges" *Expert Rev Neurother.* 11(10): 1351-1353. doi:10.1586/ern.11.129 [NIH Public Access—Author Manuscript—5 pages].
Fong et al. (2009) "Recovery of control of posture and locomotion after a spinal cord injury: solutions staring US in the face," *Progress in Brain Research*, Elsevier Amsterdam, NL,175:393-418.
Ganley et al., (2005) "Epidural Spinal Cord Stimulation Improves Locomoter Performance in Low ASIA C, Wheelchair-Dependent, Spinal Cord-Injured Individuals: Insights from Metabolic Response," *Top. Spinal Cord Inj. Rehabil*;11(2):50-63.
Gerasimenko Y., Gorodnichev R., Machueva E., Pivovarova E., Semyenov D., Savochin A., Roy R.R., and Edgerton V.R., (Mar. 10, 2010) "Novel and Direct Access to the Human Locomotor Spinal Circuitry," *J Neurosci.* 30(10):3700-3708, PMC2847395.
Gerasimenko Y.P., Ichiyama R.M., Lavrov I.A., Courtine G., Cai L., Zhong H., Roy R.R., and Edgerton V.R. (2007) "Epidural Spinal Cord Stimulation Plus Quipazine Administration Enable Stepping in Complete Spinal Adult Rats," *J Neurophysiol.* 98:2525-2536.
Harkema et al. (2011) "Effect of Epidural stimulation of the lumbosacral spinal cord on voluntary movement, standing, and assisted stepping after motor complete paraplegia: a case study" *Lancet* 377(9781): 1938-1947; NIH Public Access Author Manuscript 17 pages [doi:10.1016/S0140-6736(11)60547-3].
Herman R., He J., D'Luzansky S., Willis W., Dilli S., (2002) "Spinal cord stimulation facilitates functional walking in a chronic, incomplete spinal cord injured," *Spinal Cord.* 40:65-68.
Hofstoetter, U.S et al. (Aug. 2008) "Modification of Reflex Responses to Lumbar Posterior Root Stimulation by Motor Tasks in Healthy Subjects," *Artif Organs*, 32(8):644-648.
Hovey, et al. (2006) "The Guide to Magnetic Stimulation," *The Magstim Company Ltd*, 45 pages.
Ichiyama et al. (2005) "Hindlimb stepping movements in complete spinal rats induced by epidural spinal cord stimulation" *Neuroscience Letters*, 383:339-344.
Kapetanakis, et al. (2017) "Cauda Equina Syndrome Due to Lumbar Disc Herniation: a Review of Literature," *Folia Medica*, 59(4): 377-86.
Kitano K., Koceja D.M. (2009) "Spinal reflex in human lower leg muscles evoked by transcutaneous spinal cord stimulation," *J Neurosci Methods.* 180:111-115.
Kondo, et al. (1997) "Laser monitoring of chest wall displacement," *Eur Respir J.*, 10: 1865-1869.
Minasian et al. (2010) "Transcutaneous stimulation of the human lumbar spinal cord: Facilitating locomotor output in spinal cord injury," *Conf. Proceedings Soc. for Neurosci.*, Abstract No. 286.19, 1 page.
Minassian et al. (Aug. 2011) "Transcutaneous spinal cord stimulation," *International Society for Restorative Neurology*, http://restorativeneurology.org/resource-center/assessments/transcutaneous-lumbar-spinal-cord-stimulation/; http://restorativeneurology.org/wp-content/uploads/2011/08/Transcutaneous-spinal-cord-stimulation_long.pdf, 6 pp.
Minassian et al. (Mar. 2007) "Posterior root-muscle reflexes elicited by transcutaneous stimulation of the human lumbosacral cord," *Muscle & Nerve* 35:327-336.
Nandra et al., (2014) "Microelectrode Implants for Spinal Cord Stimulation in Rats," *Thesis, California Institute of Technology*, Pasadena, California, Defended on Sep. 24, 2014, 104 pages.
Nandra et al., (Jan. 23, 2011) "A Parylene-Based Microelectrode Array Implant for Spinal Cord Stimulation in Rats," *Conf. Proc. IEEE Eng. Med. Biol. Soc.*, pp. 1007-1010.
Niu et al., (2018) "A Proof-of-Concept Study of Transcutaneous Magnetic Spinal Cord Stimulation for Neurogenic Bladder," *Scientific Reports*, 8: 12549 (12 pages).
Rodger et al., (2007) "High Density Flexible Parylene-Based Multielectrode Arrays for Retinal and Spinal Cord Stimulation," Transducers & Eurosensors, Proc. Of the 14th International Con-

(56) References Cited

OTHER PUBLICATIONS ference on Solid-State Sensors, Actuators and Microsystems, Lyon, France, Jun. 10-14, 2007, *IEEE*, pp. 1385-1388.
Szava et al., (Jan. 2011) "Transcutaneous electrical spinal cord stimulation: Biophysics of a new rehabilitation method after spinal cord injury", ISBN: 978-3-639-34154-6 [95 pages].
Seifert et al. (Nov. 1, 2002) "Restoration of Movement Using Functional Electrical Stimulation and Bayes' Theorem," *The Journal of Neuroscience*, 22(1):9465-9474.
Tanabe et al. (2008) "Effects of transcutaneous electrical stimulation combined with locomotion-like movement in the treatment of post-stroke gait disorder: a single-case study," 30(5):411-416 abstract, 1 page.
Wang, et al. (2017) "Incidence of C5 nerve root palsy after cervical surgery," *Medicine*, 96(45), 14 pages.
Ward, Alex R. (Feb. 2009) "Electrical Stimulation Using Kilohertz-Frequency Alternating Current," (2009) *Phys Ther.*89(2):181-190 [published online Dec. 18, 2008].
Abernethy, J. et al., "Competing in the Dark: An Efficient Algorithm for Bandit Linear Optimization", Conference on Learning Theory, (2008), 13 pages.
Ada, L. et al., "Mechanically assisted walking with body weight support results in more independent walking than assisted overground walking in non-ambulatory patients early after stroke: a systematic review," Journal of Physiotherapy, vol. 56, No. 3, (Sep. 2010), 9 pages.
Alto, L. et al., "Chemotropic Guidance Facilitates Axonal Regeneration and Synapse Formation after Spinal Cord Injury," Nature Neuroscience, vol. 12, No. 9, Published Online Aug. 2, 2009, (Sep. 2009), 21 pages.
Anderson, K., "Targeting Recovery: Priorities of the Spinal Cord-Injured Population," Journal of Neurotrauma, vol. 11, No. 10, Oct. 2004, 13 pages.
Auer, P. et al., "Finite-time Analysis of the Multiarmed Bandit Problem", Machine Learning, vol. 47, No. 2, (2002), pp. 235-256.
Auer, P. "Using Confidence Bounds for Exploitation-Exploration Trade-offs", Journal of Machine Learning Research, vol. 3, (2002), pp. 397-422.
Augustine GJ, Purves D, Fitzpatrick D, eds., "Autonomic Regulation of the Bladder." Neuroscience, 2nd edition, Sunderland (MA): Sinauer Associates; 2001, Available from: https://www.ncbi.nlm.nih.gov/books/NBK10886/ ; downloaded Dec. 4, 2022, 2 pp.
Azimi, J. et al., "Batch Active Learning via Coordinated Matching", In Proceedings of the 29th International Conference on Machine Learning, (2012), 8 pages.
Azimi, J. et al., "Batch Bayesian Optimization via Simulation Matching", In Advances in Neural Information Processing Systems (NIPS), (2010), 9 pages.
Azimi, J. et al., "Hybrid Batch Bayesian Optimization", In Proceedings of the 29th International Conference on Machine Learning, (2012), 12 pages.
Barbeau, H. et al., "Recovery of locomotion after chronic spinalization in the adult cat", Brain Research, vol. 412, No. 1, (May 26, 1987), 12 pages.
Bareyre, F. et al., "The injured spinal cord spontaneously forms a new intraspinal circuit in adult rats," Nature Neuroscience, vol. 7, No. 3, Published Online Feb. 15, 2004, (Mar. 2004), 9 pages.
Basso, D. et al., "MASCIS Evaluation of Open Field Locomotor Scores: Effects of Experience and Teamwork on Reliability," Journal of Neurotrauma, vol. 13, No. 7, (Jul. 1996), 17 pages.
Brochu, et al., "A Tutorial on Bayesian Optimization of Expensive Cost Functions, with Application to Active User Modeling and Hierarchical Reinforcement Learning", In TR-2009-23, UBC, (2009), 49 pages.
Brosamle, C. et al., "Cells of Origin, Course, and Termination Patterns of the Ventral, Uncrossed Component of the Mature Rat Corticospinal Tract," The Journal of Comparative Neurology, vol. 386, No. 2, (Sep. 22, 1997), 11 pages.
Bubeck, S. et al., "Online Optimization in X-Armed Bandits", Advances in Neural Information Processing Systems (NIPS), (2008), 8 pages.
Bubeck, S. et al., "Pure Exploration in Finitely-Armed and Continuous-Armed Bandits problems" In ALT, (2009), 35 pages.
Burke, R., "Group la Synaptic Input to Fast and Slow Twitch Motor Units of Cat Triceps Surae", The Journal of Physiology, vol. 196, vol. 3, (Jun. 1, 1968), 26 pages.
CA Office Action dated Jul. 14, 2022 in Application No. CA2958924 [UCLAP133CA].
CA Office Action dated Jun. 19, 2023, in Application No. CA3030615 [UCLAP135CA].
CA Office Action dated Oct. 21, 2021 in CA Application No. CA2958924 [UCLAP133CA].
CA Office Action dated Sep. 6, 2022, in Application No. CA3030615 [UCLAP135CA].
CA Office Action dated Sep. 28, 2021, in application No. CA2925754 [UCLAP114CA].
Cai, L. et al., "Implications of Assist-As-Needed Robotic Step Training after a Complete Spinal Cord Injury on Intrinsic Strategies of Motor Learning", The Journal of Neuroscience, vol. 26, No. 41, (Oct. 11, 2006), 5 pages.
Capogrosso, M., et al., "A Computational Model for Epidural Electrical Stimulation of Spinal Sensorimotor Circuits", Journal of Neuroscience, Dec. 4, 2013, vol. 33, No. 49, pp. 19326-19340.
Carhart, M. et al., "Epidural Spinal-Cord Stimulation Facilitates Recovery of Functional Walking Following Incomplete Spinal-Cord Injury," IEEE Transactions on Neural Systems and Rehabilitation Engineering, vol. 12, No. 1, (Mar. 15, 2004), 11 pages.
Colgate, E. et al., "An Analysis of Contact Instability in Terms of Passive Physical Equivalents," Proceedings of the 1989 IEEE International Conference on Robotics and Automation, Scottsdale, Arizona, (May 14, 1989), 6 pages.
Courtine, G. et al., "Can experiments in nonhuman primates expedite the translation of treatments for spinal cord injury in humans?", Nature Medicine, vol. 13, No. 5, (May 2007), 13 pages.
Courtine, G. et al., "Recovery of supraspinal control of stepping via indirect propriospinal relay connections after spinal cord injury," Nature Medicine, vol. 14, No. 1, (Jan. 6, 2008), 6 pages.
Cowley, K. et al., "Propriospinal neurons are sufficient for bulbospinal transmission of the locomotor command signal in the neonatal rat spinal cord," The Journal of Physiology, vol. 586, No. 6, Published Online Jan. 31, 2008, (Mar. 15, 2008), 13 pages.
Danner, S. et al., "Human spinal locomotor control is based on flexibly organized burst generators," Brain, vol. 138, No. 3, Available Online Jan. 12, 2015, Mar. 2015, 12 pages.
Danner, S. M. et al., "Body Position Influences Which neural structures are recruited by lumbar transcutaneous spinal cord stimulation", PLoS ONE, vol. 11, No. 1, (2016), 13 pages.
Dimitrijevic et al. (1998) "Evidence for a spinal central pattern generator in humans." Ann N Y Acad Sci. 860:360-76.
Dimitrijevic, M. M. et al., "Clinical Elements for the Neuromuscular Stimulation and Functional Electrical Stimulation protocols in the Practice of Neurorehabilitation", Artificial Organs, vol. 26, No. 3, (2002), pp. 256-259.
Dimitrijevic, M. R. et al., "Electrophysiological characteristics of H-reflexes elicited by percutaneous stimulation of the cauda equina", Abstract No. 4927, 34th Annual Meeting of the Society for Neuroscience, San Diego, CA (2004), 1 page.
Drew, T. et al., "Cortical mechanisms involved in visuomotor coordination during precision walking," Brain Research Reviews, vol. 57, No. 1, Published Online Aug. 22, 2007, (Jan. 2007), 13 pages.
Duschau-Wicke, A. et al., "Patient-cooperative control increases active participation of individuals with SCI during robot-aided gait training," Journal of NeuroEngineering and Rehabilitation, vol. 7, No. 43, (Sep. 10, 2010), 13 pages.
Edgerton, V. et al., "Robotic Training and Spinal Cord Plasticity," Brain Research Bulletin, vol. 78, No. 1, Published Online Nov. 14, 2008, (Jan. 15, 2009), 19 pages.
Edgerton, V. et al., "Training Locomotor Networks," Brain Research Reviews, vol. 57, Published Online Sep. 16, 2007, (Jan. 2008), 25 pages.

(56) References Cited

OTHER PUBLICATIONS

European Office Action [Decision to Refuse] dated Oct. 28, 2021 issued in EP 15834593.4 [UCLAP133EP].
European Search Report dated Apr. 19, 2022, in Application No. EP 19851613.0 [UCLAP206EP].
European Search Report dated Apr. 19, 2022, in Application No. EP 19852797.0 [UCLAP197EP].
Fleshman, J. et al., "Electronic Architecture of Type-Identified a-Motoneurons in the Cat Spinal Cord," Journal of Neurophysiology, vol. 60, No. 1, (Jul. 1, 1988), 26 pages.
Frey, M. et al., "A Novel Mechatronic Body Weight Support System," IEEE Transactions on Neural Systems and Rehabilitation Engineering, vol. 14, No. 3, (Sep. 18, 2006), 11 pages.
Fuentes, R. et al., "Spinal Cord Stimulation Restores Locomotion in Animal Models of Parkinson's Disease," Science, vol. 323, No. 5921, (Mar. 20, 2009), 14 pages.
Gerasimenko et al. (2015) "Initiation and modulation of locomotor circuitry output with multisite transcutaneous electrical stimulation of the spinal cord in noninjured humans." J Neurophysiol. 113:834-42.
Gerasimenko et al. (2015) "Transcutaneous electrical spinal-cord stimulation in humans." Ann Phys Rehabil Med. 58(4):225-231. doi:10.1016/j.rehab.2015.05.003.
Gerasimenko, Yu. P. et al., "Control of Locomotor Activity in Humans and Animals in the Absence of Supraspinal Influences", Neuroscience and Behavioral Physiology, vol. 32, No. 4, (2002), pp. 417-423.
Gerasimenko, Yu. P. et al., "Noninvasive Reactivation of Motor Descending Control after Paralysis", Journal of Neurotrauma, vol. 32, (2015), 13 pages.
Gilja, V. et al., "A high-performance neural prosthesis enabled by control algorithm design," Nature Neuroscience, vol. 15, No. 12, Published Online Nov. 18, 2012, (Dec. 2012), 56 pages.
Gittins, J. C., "Bandit Processes and Dynamic Allocation Indices", Journal of the Royal Statistical Society B, vol. 41, No. 2, (1979), pp. 148-164.
Giuliano, F. et al., "Neural control of erection", Physiology & Behavior, vol. 83, No. 2, Nov. 15, 2004, pp. 189-201.
Guyatt, G. H. et al., "The 6-minute walk: a new measure of exercise capacity in patients with chronic heart failure," Canadian Medical Association Journal, vol. 132, No. 8, (Apr. 15, 1985), 5 pages.
Hagglund, M. et al., "Activation of groups of excitatory neurons in the mammalian spinal cord or hindbrain evokes locomotion," Nature Neuroscience, vol. 13, No. 2, Published Online Jan. 17, 2010, (Feb. 2010), 8 pages.
Harkema, S. et al., "Human Lumbosacral Spinal Cord Interprets Loading During Stepping," Journal of Neurophysiology, vol. 77, No. 2, (Feb. 1, 1997), 15 pages.
Harrison, P. et al., "Individual Excitatory Post-Synaptic Potentials Due to Muscle Spindle Ia Afferents in Cat Triceps Surae Motoneurones," The Journal of Physiology, vol. 312, No. 1, (Mar. 1981), pp. 455-470.
Hashtrudi-Zaad, K. et al., "On the Use of Local Force Feedback for Transparent Teleoperation," Proceedings of the 1999 IEEE International Conference on Robotics and Automation, (May 10, 1999), 7 pages.
Hennig, P. et al., "Entropy search for information-efficient global optimization" Journal of Machine Learning Research (JMLR), vol. 13, (Jun. 2012), pp. 1809-1837.
Hidler, J. et al., "ZeroG: Overground gait and balance training system," Journal of Rehabilitation Research & Development, vol. 48, No. 4, Available as Early as Jan. 1, 2011, (2011), 12 pages.
Hines, M. L. et al., "The NEURON Simulation Environment," Neural Computation, vol. 9, No. 6, (Aug. 15, 1997), 26 pages.
Hofstoetter, U. S. et al., "Effects of transcutaneous spinal cord stimulation on voluntary locomotor activity in an incomplete spinal cord injured individual", Biomed Tech, vol. 58 (Suppl. 1), (2013), 3 pages.
Hofstoetter, U. S. et al., "Model of spinal cord reflex circuits in humans: Stimulation frequency-dependence of segmental activities and their interactions", Second Congress International Society of Intraoperative Neurophysiology (ISIN), Dubrovnik, Croatia, (2009), 149 pages.
Hofstoetter, U. S. et al., "Modification of spasticity by transcutaneous spinal cord stimulation in individuals with incomplete spinal cord injury", The Journal of Spinal Cord Medicine, vol. 37, No. 2, (2014), pp. 202-211.
Ivanenko, Y. P. et al., "Temporal Components of the Motor Patterns Expressed by the Human Spinal Cord Reflect Foot Kinematics," Journal of Neurophysiology, vol. 90, No. 5, Nov. 2003, Published Online Jul. 9, 2003, (2003), 11 pages.
Jarosiewicz, B. et al., "Supplementary Materials for Virtual typing by people with tetraplegia using a self-calibrating intracortical brain-computer interface," Science Translational Medicine, vol. 7, No. 313, (Nov. 11, 2015), 26 pages.
Jarosiewicz, B. et al., "Virtual typing by people with tetraplegia using a self-calibrating intracortical brain-computer interface," Science Translational Medicine, vol. 7, No. 313, (Nov. 11, 2015), 11 pages.
Jilge, B. et al., "Initiating extension of the lower limbs in subjects with complete spinal cord injury by epidural lumbar cord stimulation", Exp Brain Res., vol. 154, (2004), pp. 308-326.
Johnson, W. L. et al., "Application of a Rat Hindlimb Model: A Prediction of Force Spaces Reachable Through Stimulation of Nerve Fascicles," IEEE Transactions on Bio-Medical Engineering, vol. 58, No. 12, Available Online Jan. 17, 2011, (Dec. 2011), 11 pages.
Jones, D. R. et al., "Efficient Global Optimization of Expensive Black-Box Functions", Journal of Global Optimization, vol. 13, (1998), pp. 455-492.
Jones, K. E. et al., "Computer Simulation of the Responses of Human Motoneurons to Composite 1A EPSPS: Effects of Background Firing Rate," The Journal of Physiology, vol. 77, No. 1, (1997), 16 pages.
JP Office Action dated Nov. 21, 2022, in Application No. 2021-188658 with English translation [UCLAP135JPD1].
JP Office Action dated Feb. 17, 2023 in Application No. JP2019-539960 with English translation [UCLAP181JP].
JP Office Action dated Nov. 29, 2021, in Application No. JP2019-539960 with English translation [UCLAP181JP].
JP Office Action dated Sep. 26, 2022, in Application No. JP2019-539960 with English translation [UCLAP181JP].
JP Office Action dated Jul. 18, 2023, in Application No. JP2021-509772 with English translation [UCLAP206JP].
Kakulas, B., "A Review of the Neuropathology of Human Spinal Cord Injury with Emphasis on Special Features," Proceedings of the Donald Munro Memorial Lecture at the American Paraplegia Society 44th Annual Conference, Las Vegas, Nevada, (Sep. 9, 1998), 6 pages.
Kirkwood, P., "Neuronal Control of Locomotion: From Mollusc to Man—G.N. Orlovsky, T.G. Deliagina and S. Grillner. Oxford University Press, Oxford, 1999. ISBN 0198524056 (Hbk), 322 pp.," Clinical Neurophysiology, vol. 111, No. 8, Published Online Jul. 17, 2000, (Aug. 1, 2000), 2 pages.
Kleinberg, R. et al., "Multi-armed bandits in metric spaces", In STOC, Computer and Automation Research Institute of the Hungarian Academy of Sciences, Budapest, Hungary, (2008), pp. 681-690.
Kocsis, L. et al. "Bandit Based Monte-Carlo Planning", European Conference on Machine Learning, Springer, Berlin, Heidelberg, (Sep. 2006), pp. 282-293.
Krassioukov, A. et al., "A Systematic Review of the Management of Autonomic Dysreflexia Following Spinal Cord Injury," Archives of Physical Medicine and Rehabilitation, vol. 90, No. 4, Apr. 2009, 27 pages.
Krassioukov, A. et al., "A Systematic Review of the Management of Orthostatic Hypotension Following Spinal Cord Injury," Archives of Physical Medicine and Rehabilitation, vol. 90, No. 5, May 2009, 22 pages.
Krause, A. et al. "Contextual Gaussian Process Bandit Optimization", In Advances in Neural Information Processing Systems (NIPS), (2011), 9 pages.

(56) References Cited

OTHER PUBLICATIONS

Krause, A. et al., "Near-optimal Nonmyopic Value of Information in Graphical Models", In UAI, (2005), 8 pages.
Krause, A. et al. "Near-Optimal Sensor Placements in Gaussian Processes: Theory, Efficient Algorithms and Empirical Studies", Journal of Machine Learning Research (JMLR), vol. 9, (Feb. 2008), pp. 235-284.
Krenn et al. (2013) "Selectivity of transcutaneous stimulation of lumbar posterior roots at different spinal levels in humans." Biomed Tech (Berl) 58 (Suppl. 1) DOI 10.1515/bmt-2013-4010, 2 pages.
Kwakkel, G. et al., "Effects of Robot-assisted therapy on upper limb recovery after stroke: A Systematic Review," Neurorehabilitation and Neural Repair, vol. 22, No. 2, Published Online Sep. 17, 2007, (Mar. 2008), 11 pages.
Ladenbauer et al. (2010) "Stimulation of the human lumbar spinal cord with implanted and surface electrodes: a computer simulation study." IEEE Trans Neural Syst Rehabil Eng. 18:637-45.
Lavrov, I. et al., "Epidural Stimulation Induced Modulation of Spinal Locomotor Networks in Adult Spinal Rats," Journal of Neuroscience, vol. 28, No. 23, (Jun. 4, 2008), 8 pages.
Liu, J. et al., "Stimulation of the Parapyramidal Region of the Neonatal Rat Brain Stem Produces Locomotor-Like Activity Involving Spinal 5-HT7 and 5-HT2A Receptors", Journal of Neurophysiology, vol. 94, No. 2, Published Online May 4, 2005, (Aug. 1, 2005), 13 pages.
Lizotte, D. et al., "Automatic gait optimization with Gaussian process regression", In IJCAI, (2007), pp. 944-949.
Lovely, R. et al., "Effects of Training on the Recovery of Full-Weight-Bearing Stepping in the Adult Spinal Cat," Experimental Neurology, vol. 92, No. 2, (May 1986), 15 pages.
Lozano, A. et al., "Probing and Regulating Dysfunctional Circuits Using Deep Brain Stimulation," Neuron, vol. 77, No. 3, (Feb. 6, 2013), 19 pages.
Mcintyre, C. C. et al., "Modeling the Excitability of Mammalian Nerve Fibers: Influence of Afterpotentials on the Recovery Cycle," Journal of Neurophysiology, vol. 87, No. 2, (Feb. 2002), 12 pages.
Minassian et al., "Mechanisms of rhythm generation of the human lumbar spinal cord in repose to tonic stimulation without and with step-related sensory feedback", Biomed Tech, vol. 58, (Suppl. 1), (2013), 3 pages.
Minassian, K. et al., "Human lumbar cord circuitries can be activated by extrinsic tonic input to generate locomotor-like activity", Human Movement Science, vol. 26, No. 2, (2007), pp. 275-295.
Minassian, K. et al., "Neuromodulation of lower limb motor control in restorative neurology", Clinical Neurology and Neurosurgery, vol. 114, (2012), pp. 489-497.
Minassian, K. et al., "Peripheral and Central Afferent Input to the Lumbar Cord", Biocybernetics and Biomedical Engineering, vol. 25, No. 3, (2005), pp. 11-29.
Minassian, K. et al., "Stepping-like movements in humans with complete spinal cord injury induced by epidural stimulation of the lumbar cord: electromyographic study of compound muscle action potentials", Spinal Cord, vol. 42, (2004), pp. 401-416.
Minev, I. R. et al., "Electronic dura mater for long-term multimodal neural interfaces," Science Magazine, vol. 347, No. 6218, (Jan. 9, 2015), 64 pages.
Minoux, M., Accelerated greedy algorithms for maximizing submodular set functions. Optimization Techniques, LNCS, (1978), pp. 234-243.
Moraud, E. et al., "Mechanisms Underlying the Neuromodulation of Spinal Circuits for Correcting Gait and Balance Deficits after Spinal Cord Injury," Neuron, vol. 89, No. 4, Feb. 17, 2016, Published Online Feb. 4, 2016, 15 pages.
Murg, M et al., "Epidural electric stimulation of posterior structures of the human lumbar spinal cord: 1. Muscle twitches—a functional method to define the site of stimulation", Spinal Cord, vol. 38, (2000), pp. 394-402.
Musienko, P. et al., "Combinatory Electrical and Pharmacological Neuroprosthetic Interfaces to Regain Motor Function After Spinal Cord Injury," IEEE Transactions on Biomedical Engineering, vol. 56, No. 11, Published Online Jul. 24, 2009, (Nov. 2009), 5 pages.
Musienko, P. et al., "Controlling specific locomotor behaviors through multidimensional monoaminergic modulation of spinal circuitries," The Journal of Neuroscience, vol. 31, No. 25, (Jun. 22, 2011), 15 pages.
Musienko, P. et al. "Multi-system neurorehabilitative strategies to restore motor functions following severe spinal cord injury," Experimental Neurology, vol. 235, No. 1, Published Online Sep. 7, 2011, (May 2012), 10 pages.
Musselman, K. et al., "Spinal Cord Injury Functional Ambulation Profile: A New Measure of Walking Ability," Neurorehabilitation and Neural Repair, vol. 25, No. 3, Published Online Feb. 25, 2011, (Mar. 2011), 9 pages.
Nandra, M. S. et al., "A wireless microelectrode implant for spinal cord stimulation and recording in rats", Presentation Abstract, 2013, 104 pages.
National Health Service., "Lumbar Decompression Surgery: When it's used", NHS, Apr. 28, 2022, https://www.nhs.uk/conditions/lumbar-decompression-surgery/why-its-done/#:-:text=Cauda%20equina%20syndrome%20is%20a,is%20severe%20or%20getting%20worse.
Nessler, J. et al., "A Robotic Device for Studying Rodent Locomotion After Spinal Cord Injury," IEEE Transactions on Neural Systems and Rehabilitation Engineering, vol. 13, No. 4, (Dec 12, 2005), 10 pages.
PCT International Preliminary Report on Patentability and Written Opinion dated Dec 2, 2021 issued in PCT/US2020/033830 [UCLAP211WO].
Pearson, K. G., "Generating the walking gait: role of sensory feedback," Progress in Brain Research, vol. 143, Chapter 12, Published Online Nov. 28, 2003, (2004), 7 pages.
Phillips, A. et al., "Contemporary Cardiovascular Concerns after Spinal Cord Injury: Mechanisms, Maladaptations, and Management," Journal of Neurotrama, vol. 32, No. 24, Dec. 15, 2015, 17 pages.
Phillips, A. et al., "Perturbed and spontaneous regional cerebral blood flow responses to changes in blood pressure after high-level spinal cord injury: the effect of midodrine," Journal of Applied Physiology, vol. 116, No. 6, Mar. 15, 2014, Available Online Jan. 16, 2014, 9 pages.
Phillips, A. et al., "Regional neurovascular coupling and cognitive performance in those with low blood pressure secondary to high-level spinal cord injury: improved by alpha-1 agonist midodrine hydrochloride," Journal of Cerebral Blood Flow & Metabolism, vol. 34, No. 5, May 2014, 8 pages.
Pratt, G. et al., "Stiffness Isn't Everything," Proceedings of the Fourth International Symposium on Experimental Robotics, (Jun. 30, 1995), 6 pages.
Pratt, J. et al., "Series elastic actuators for high fidelity force control," Industrial Robot: An International Journal, vol. 29, No. 3, Available as Early as Jan. 1, 2002, (2002), 13 pages.
Prochazka, A. et al., "Ensemble firing of muscle afferents recorded during normal locomotion in cats," The Journal of Physiology, vol. 507, No. 1, (Feb. 15, 1998), 12 pages.
Prochazka, A. et al., "Models of ensemble filing of muscle spindle afferents recorded during normal locomotion in cats," The Journal of Physiology, vol. 507, No. 1, (Feb. 15, 1998), 15 pages.
Pudo, D. et al., "Estimating Intensity Fluctuations in High Repetition Rate Pulse Trains Generated Using the Temporal Talbot Effect", IEEE Photonics Technology Letters, vol. 18, No. 5, (Mar. 1, 2006), 3 pages.
Rasmussen, C. E. et al., "Gaussian Processes for Machine Learning (GPML) Toolbox", The Journal of Machine Learning Research, vol. 11, (2010), pp. 3011-3015.
Rasmussen, C. E. et al., "Gaussian Processes for Machine Learning", The MIT Press, Cambridge, Massachusetts, (2006), 266 pages.
Rasmussen, C. E. "Gaussian Processes in Machine Learning", L.N.A.I., vol. 3176, (2003) pp. 63-71.
Rattay, F. et al., "Epidural electrical stimulation of posterior structures of the human lumbosacral cord: 2. Quantitative analysis by computer modeling", Spinal Cord, vol. 38, (2000), pp. 473-489.

(56) References Cited

OTHER PUBLICATIONS

Reinkensmeyer, D. et al., "Tools for understanding and optimizing robotic gait training," Journal of Rehabilitation Research & Development, vol. 43, No. 5, (Aug. 2006), 14 pages.
Rejc, E. et al., "Effects of Lumbosacral Spinal Cord Epidural Stimulation for Standing after Chronic Complete Paralysis in Humans," PLoS One, vol. 10, No. 7, (Jul. 24, 2015), 20 pages.
Robbins, H., "Some Aspects of the Sequential Design of Experiments", Bull. Amer. Math. Soc, vol. 58, (1952), pp. 527-535.
Rosenzweig, E. et al., "Extensive Spontaneous Plasticity of Corticospinal Projections After Primate Spinal Cord Injury", Nature Neuroscience, vol. 13, No. 12, Published Online Nov. 14, 2010, (Dec. 2010), 19 pages.
Roy et al. (2012) "Effect of percutaneous stimulation at different spinal levels on the activation of sensory and motor roots." Exp Brain Res. 223:281-9.
Ryzhov, I. O. et al., "The knowledge gradient algorithm for a general class of online learning problems", Operations Research, vol. 60, No. 1, (2012), pp. 180-195.
Sayenko, D. et al., "Neuromodulation of evoked muscle potentials induced by epidural spinal-cord stimulation in paralyzed individuals," Journal of Neurophysiology, vol. 111, No. 5, Published Online Dec. 11, 2013, (2014), 12 pages.
Sayenko et al. (2014) "Neuromodulation of evoked muscle potentials induced by epidural spinal-cord stimulation in paralyzed individuals." J Neurophysiol. 111:1088-99.
Sayenko et al. (2015) "Spinal segment-specific transcutaneous stimulation differentially shapes activation pattern among motor pools in humans." J Appl Physiol. 118:1364-74.
Shafik, A (1996) "Extrapelvic cavernous nerve stimulation in erectile dysfunction. Human study" Andrologia 28(3):151-6. doi: 10.1111/j.1439-0272.1996.tb02774.x [ABSTRACT—2 pages].
Shafik, et al. (2000) "Magnetic stimulation of the cavernous nerve for the treatment of erectile dysfunction in humans" International Journal of Impotence Research 12: 137-141.
Shamir, R. R. et al., "Machine Learning Approach to Optimizing Combined Stimulation and Medication Therapies for Parkinson's Disease," Brain Stimulation, vol. 8, No. 6, Published Online Jun. 15, 2015, (Nov. 2015), 22 pages.
Srinivas, N. et al., "Gaussian process optimization in the bandit setting: No regret and experimental design", In Proceedings of the 27th International Conference on Machine Learning, (2010), 17 pages.
Steward, O. et al., "False Resurrections: Distinguishing Regenerated from Spared Axons in the Injured Central Nervous System", The Journal of Comparative Neurology, vol. 459, No. 1, (Apr. 21, 2003), 8 pages.
Stienen, A. H. A. et al., "Analysis of reflex modulation with a biologically realistic neural network," Journal of Computer Neuroscience, vol. 23, No. 3, Available Online May 15, 2007, (Dec. 2007), 16 pages.
Sun, F. et al., "Sustained axon regeneration induced by co-deletion of PTEN and SOCS3", Nature, vol. 480, No. 7377, Published Online Nov. 6, 2011, (Dec. 15, 2011), 12 pages.
Takeoka, A. et al., "Muscle Spindle Feedback Directs Locomotor Recovery and Circuit Reorganization after Spinal Cord Injury", Cell, vol. 159, No. 7, (Dec. 18, 2014), 27 pages.
Temel, et al. (2004) "Deep brain stimulation of the thalamus can influence penile erection" International Journal of Impotence Research 16: 91-94.
Tenne, Y. et al., "Computational Intelligence in Expensive Optimization Problems", vol. 2 of Adaptation, Learning, and Optimization, Springer, Berlin Heidelberg, (2010), pp. 131-162.
Timozyk, W. et al., "Hindlimb loading determines stepping quantity and quality following spinal cord transection," Brain Research, vol. 1050, No. 1-2, Published Online Jun. 24, 2005, (Jul. 19, 2005), 10 pages.
Troni et al. (2011) "A methodological reappraisal of non invasive high voltage electrical stimulation of lumbosacral nerve roots." Clin Neurophysiol. 122:2071-80.
U.S. Final Office Action dated Apr. 6, 2023 in U.S. Appl. No. 16/615,765 [UCLAP183US].
US Final Office Action dated Dec. 6, 2021 issued in U.S. Appl. No. 16/615,765 [UCLAP183US].
U.S. Final Office Action dated Jun. 1, 2023 in U.S. Appl. No. 16/479,201 [UCLAP181US].
US Final Office Action dated Nov. 26, 2021 issued in U.S. Appl. No. 15/740,323 [UCLAP135US].
U.S. Final Office Action dated Oct. 13, 2022, in U.S. Appl. No. 17/269,970 [UCLAP206US].
U.S. Non Final Office Action dated Aug. 25, 2022 in U.S. Appl. No. 16/479,201 [UCLAP181US].
U.S. Non-Final Office Action dated Apr. 28, 2023, in U.S. Appl. No. 17/270,402 [UCLAP197US].
U.S. Non-Final Office Action dated Feb. 15, 2023 in U.S. Appl. No. 15/740,323 [UCLAP135US].
U.S. Non-Final office Action dated Jun. 20, 2022 in U.S. Appl. No. 16/615,765 [UCLAP183US].
U.S. Non-Final office Action dated May 11, 2022, in U.S. Appl. No. 15/740,323 [UCLAP135US].
US Notice of Allowance dated Dec. 13, 2021 issued in U.S. Appl. No. 15/753,963 [UCLAP150US].
US Notice of Allowance dated Mar. 4, 2022 issued in U.S. Appl. No. 15/975,678 [UCLAP115C1US].
US Office Action dated Jan. 5, 2022 issued in U.S. Appl. No. 17/269,970 [UCLAP206US].
U.S. Restriction Requirement dated Apr. 19, 2022 in U.S. Appl. No. 16/479,201 [UCLAP181US].
U.S. Restriction Requirement dated Dec. 1, 2022 in U.S. Appl. No. 17/270,402 [UCLAP197US].
Vallery, H. et al., "Compliant Actuation of Rehabilitation Robots," IEEE Robotics & Automation Magazine, vol. 15, No. 3, (Sep. 12, 2008), 10 pages.
Van Den Brand, R. et al., "Restoring Voluntary Control of Locomotion after Paralyzing Spinal Cord Injury," Science Magazine, vol. 336, No. 6085, (Jun. 1, 2012), 5 pages.
Vital Signs—Cleveland Clinic [retrieved on Nov. 22, 2021] Retrieved from the Internet: URL: https://my.clevelandclinicorg/health/articles/10881-vital-signs [7 pages].
Wan, D. et al., "Life-threatening outcomes associated with autonomic dysreflexia: A clinical review," Journal of Spinal Cord Medicine, vol. 37, No. 1, (Jan. 2014), 9 pages.
Wenger, N. et al. "Closed-loop neuromodulation of spinal sensorimotor circuits controls refined locomotion after complete spinal cord injury" Sci Transl Med. Sep. 24, 2014, vol. 6, Issue 255, (10 pages).
Wenger, N. et al., "Spatiotemporal neuromodulation therapies engaging muscle synergies improve motor control after spinal cord injury," Natural Medicine, vol. 22, No. 2, Available Online Jan. 18, 2016, (Feb. 2016), 33 pages.
Wenger, N. et al., "Supplementary Materials for Closed-loop neuromodulation of spinal sensorimotor circuits controls refined locomotion after complete spinal cord injury," Science Translational Medicine, vol. 6, No. 255, Sep. 24, 2014, 14 pages.
Wernig, A. et al., "Laufband locomotion with body weight support improved walking in persons with severe spinal cord injuries", Paraplegia, vol. 30, No. 4, (Apr. 1992), 10 pages.
Wernig, A., "Ineffectiveness of Automated Locomotor Training," Archives of Physical Medicine and Rehabilitation, vol. 86, No. 12, (Dec. 2005), 2 pages.
Wessels, M. et al., "Body Weight-Supported Gait Training for Restoration of Walking in People With an Incomplete Spinal Cord Injury: A Systematic Review," Journal of Rehabilitation Medicine, vol. 42, No. 6, (Jun. 2010), 7 pages.
Widmer, C. et al., Inferring latent task structure for multitask learning by multiple kernel learning, BMC Bioinformatics, vol. 11, (Suppl 8:S5), (2010), 8 pages.
Winter, D. A. et al., "An integrated EMG/biomechanical model of upper body balance and posture during human gait," Progress in Brain Research, vol. 97, Ch. 32, Available as Early as Jan. 1, 1993, (1993), 9 pages.

(56) References Cited

OTHER PUBLICATIONS

Wirz, M. et al., “Effectiveness of automated locomotor training in patients with acute incomplete spinal cord injury: A randomized controlled multicenter trial,” BMC Neurology, vol. 11, No. 60, (May 27, 2011), 9 pages.
Yakovenko, S. et al., “Spatiotemporal Activation of Lumbosacral Motoneurons in the Locomotor Step Cycle,” Journal of Neurophysiology, vol. 87, No. 3, (Mar. 2002), 12 pages.
Zhang, T. C. et al., “Mechanisms and models of spinal cord stimulation for the treatment of neuropathic pain,” Brain Research, vol. 1569, Published Online May 4, 2014, (Jun. 20, 2014), 13 pages.
Zorner, B. et al., “Profiling locomotor recovery: comprehensive quantification of impairments after CNS damage in rodents,” Nature Methods, vol. 7, No. 9, Published Online Aug. 15, 2010, (Sep. 2010), 11 pages.
Anonymous, “Re: Round corners (fillet) in Illustrator CS6”, in: Stack Exchange [online], Graphic Design, Jan. 22, 2018; 17:52 [retrieved on Feb. 6, 2024]. Retrieved from the Internet: <URL:https://graphicdesign.stackexchange.com/questions/104349/round-corners-fillet-in-illustrator-cs6>, 10 pages.
Ateh, D. D. et al., “Polypyrrole-based conducting polymers and interactions with biological tissues”, Journal of the Royal Society Interface, (2006), vol. 3, No. 11, pp. 741-752.
Australian Examination Report No. 1 in counterpart Australian Patent Application No. 2017202237 mailed Apr. 6, 2018, 3 pages.
Australian Examination Report No. 1 in counterpart Australian Patent Application No. 2017203132 mailed Oct. 13, 2017, 4 pages.
Australian Examination Report No. 1 in counterpart Australian Patent Application No. 2017221868 mailed Jan. 23, 2018, 3 pages.
Axisa, F. et al., “Elastic and Conformable Electronic Circuits and Assemblies using MID in polymer”, 6th International Conference on Polymers and Adhesives in Microelectronics and Photonics, IEEE Polytronic 2007 Conference, (2007), pp. 280-286.
Bizzi, E. et al., “Modular organization of motor behavior”, Zeitschrift f r Naturforschung, (1998), vol. 53, No. 7-8, pp. 510-517.
Bruckenstein, S. et al., “An experimental study of nonuniform current distribution at rotating disk electrodes”, Journal of the Electrochemical Society, (1970), vol. 117, No. 8, pp. 1044-1048.
Canadian Office Action in counterpart Canadian Patent Application No. 2823592 mailed Oct. 5, 2017, 4 pages.
Canadian Office Action in counterpart Canadian Patent Application No. 2824782 mailed Nov. 29, 2017, 4 pages.
Canadian Office Action in counterpart Canadian Patent Application No. 2825550 mailed Jan. 24, 2018, 4 pages.
Canadian Office Action in counterpart Canadian Patent Application No. 2856202 mailed Jun. 19, 2018, 4 pages.
Capogrosso, M. et al., “A Brain-Spinal Interface Alleviating Gait Deficits after Spinal Cord Injury in Primates”, Nature, (2016), vol. 539, No. 7628, pp. 284-288.
Chatagny, P. et al., “Distinction between hand dominance and hand preference in primates: a behavioral investigation of manual dexterity in nonhuman primates (macaques) and human subjects”, Brain and Behavior, (2013), vol. 3, No. 5, pp. 575-595.
Communication Pursuant to Article 94(3) EPC in counterpart European Application No. 19209911.7 mailed Jul. 20, 2023, 5 pages.
Communication Pursuant to Article 94(3) EPC in counterpart European Application No. 19209911.7 mailed Mar. 1, 2023, 2 pages.
Communication Pursuant to Article 94(3) EPC in counterpart European Patent Application No. 12760696.0 mailed Nov. 9, 2017, 5 pages.
Communication Pursuant to Article 94(3) EPC in counterpart European Patent Application No. 12848368.2 mailed May 9, 2018, 5 pages.
Communication Pursuant to Article 94(3) EPC in counterpart European Patent Application No. 17826212.7 mailed Dec. 21, 2020, 7 pages.
Communication Pursuant to Article 94(3) EPC in counterpart European Patent Application No. 18807366.2 mailed Mar. 22, 2023, 4 pages.
Communication Pursuant to Article 94(3) EPC in counterpart European Patent Application No. 20160841.1 mailed Mar. 6, 2024, 5 pages.
Communication Pursuant to Article 94(3) EPC in counterpart European Patent Application No. 20726108.2 mailed Mar. 20, 2024, 4 pages.
Communication Pursuant to Article 94(3) EPC in counterpart European Patent Application No. 211660801.7 mailed Mar. 7, 2024, 6 pages.
Communication Pursuant to Article 94(3) EPC in counterpart European Patent Application No. 21166801.7 mailed Mar. 7, 2024, 6 pages.
Communication Pursuant to Article 94(3) EPC in counterpart European Patent Application No. 24153829.7 mailed Apr. 4, 2025, 5 pages.
Communication Regarding Extended European Search Report in counterpart European Patent Application No. 24153829.7 mailed May 22, 2024, 8 pages.
Cotton, D. P. J. et al., “A Multifunctional Capacitive Sensor for Stretchable Electronic Skins”, IEEE Sensors Journal, IEEE Service Center, New York, NY, US, (2009), vol. 9, No. 12, pp. 2008-2009.
Coursera, “What is Machine Learning? Definition, Types, and Examples,” Coursera, May 20, 2025. Retrieved from the Internet: <URL:https://www.coursera.org/articles/what-is-machine-learning>, 12 pages.
Courtine, G. et al., “Transformation of nonfunctional spinal circuits into functional states after the loss of brain input”, Nature Neuroscience, (2009), vol. 12, No. 10, pp. 1333-1342.
Cyganowski, A et al., “Stretchable electrodes for neuroprosthetic interfaces”, Sensors, 2012 IEEE, Taipei, (2012), pp. 1-4.
Dani, V. et al., “Stochastic Linear Optimization Under Bandit Feedback”, In Proceedings of the 21st Annual Conference on Learning Theory (COLT), (2008), No. 101, pp. 1-15.
Definition of “Insert”, Dictionary [online], Oxford English Dictionary, 2020 [retrieved on Dec. 15, 2022], 2 pages.
Dominici, N. et al. “Versatile robotic interface to evaluate, enable and train locomotion and balance after neuromotor disorders”, Nature Medicine, (2012), vol. 18, No. 7, pp. 1-8.
Dunne, L. et al., “Initial development and testing of a novel foam-based pressure sensor for wearable sensing”, Journal of NeuroEngineering and Rehabilitation, (2005), vol. 2, No. 4, pp. 1-7.
EPO Communication and Supplementary European Search Report in counterpart European Patent Application No. 17745012.9 mailed Aug. 13, 2019, 8 pages.
European Opposition filed in counterpart European Patent Application No. 17826212.7 mailed Dec. 2, 2022, 56 pages.
Extended European Search Report in counterpart European Patent Application No. 18173218.1 mailed Jan. 7, 2019, 6 pages.
Extended European Search Report in counterpart European Patent Application No. 19211738.0 mailed May 27, 2020, 8 pages.
Extended European Search Report in counterpart European Patent Application No. 20020190.3 mailed Oct. 5, 2020, 7 pages.
Extended European Search Report in counterpart European Patent Application No. 20163794.9 mailed Sep. 18, 2020, 7 pages.
Extended European Search Report in counterpart European Patent Application No. 20164082.8 mailed Jul. 21, 2020, 7 pages.
Extended European Search Report in counterpart European Patent Application No. 23189900.6 mailed Jan. 15, 2024, 7 pages.
Extended European Search Report in counterpart European Patent Application No. 19211698.6 mailed May 28, 2020, 6 pages.
Feng, G. H. et al., “Universal concept for fabricating micron to millimeter sized 3-D parylene structures on rigid and flexible substrates”, in Proc. IEEE 15th Internal Conference on Micro Electro Mechanical System, Kyoto, Japan, (2003), pp. 594-597.
Gerasimenko, Y. et al., “Spinal cord reflexes induced by epidural spinal cord stimulation in normal awake rats”, Journal of Neuroscience Methods, (2006), vol. 157, No. 2, pp. 253-263.
Ginsbourger, D. et al., “Kriging is well-suited to parallelize optimization”, Computational Intelligence in Expensive Optimization Problems, Berlin, Heidelberg: Springer Berlin Heidelberg, (2010), Ch. 6, pp. 131-162.

(56) References Cited

OTHER PUBLICATIONS

Graf, N. et al., "Electrochemically Stimulated Release from Liposomes Embedded in a Polyelectrolyte Multilayer", Advanced Functional Materials, (2011), vol. 21, No. 9, pp. 1666-1672.
Graz, I. et al., "Flexible ferroelectret field-effect transistor for large-area sensor skins and microphones", Applied Physics Letters, American Institute of Physics, (2006), vol. 89, No. 7, pp. 73501-1-73501-3.
Graz, I. et al., "Silicone substrate with in situ strain relief for stretchable thin-film transistors", Applied Physics Letters, AIP, American Institute of Physics, (2011), vol. 98, No. 12, pp. 124101-1-124101-3.
Harkema, S. et al., "Normalization of Blood Pressure with Spinal Cord Epidural Stimulation After Severe Spinal Cord Injury", Frontiers in Human Neuroscience, (2018), vol. 12, pp. 1-11.
Health Journalism Glossary: Bidirectional, Definition [online], Association of Health Care Journalists, 2024. Retrieved from the Internet: <URL:https://healthjournalism.org/glossary-terms/bidirectional/>, 3 pages.
Hohenschurz-Schmidt, D. J. et al., "Linking Pain Sensation to the Autonomic Nervous System: The Role of the Anterior Cingulate and Periaqueductal Gray Resting-State Networks", Front Neuroscience, (2020), vol. 14, No. 147, pp. 1-15.
Hung, C. C. et al., "Transparent microprobe array fabricated by MEMS hot embossing technology for photodynamic therapy application", IEICE Electronics Express, (2010), vol. 7, No. 9, pp. 569-576.
International Search Report and Written Opinion issued in counterpart PCT Application No. EP2020/063564, mailed Sep. 11, 2020, 12 pages.
International Search Report and Written Opinion issued in counterpart PCT Application No. PCT/EP2017/083478, mailed May 3, 2018, 10 pages.
International Search Report and Written Opinion issued in counterpart PCT Application No. PCT/EP2018/082939, mailed Feb. 14, 2019, 11 pages.
International Search Report and Written Opinion issued in counterpart PCT Application No. PCT/EP2018/082942, mailed Feb. 14, 2019, 11 pages.
International Search Report and Written Opinion issued in counterpart PCT Application No. PCT/EP2020/053381, mailed May 12, 2020, 8 pages.
International Search Report and Written Opinion issued in counterpart PCT Application No. PCT/EP2020/063563, mailed Jul. 30, 2020, 14 pages.
International Search Report and Written Opinion issued in counterpart PCT Application No. PCT/US2015/011263 mailed May 19, 2015, 12 pages.
International Search Report and Written Opinion issued in counterpart PCT Application No. PCT/US2017/015435, mailed May 8, 2017, 9 pages.
International Search Report and Written Opinion issued in counterpart PCT Application No. PCT/US2022/024673 mailed Jun. 28, 2022, 8 pages.
Iyer, P. C. et al., "Characterization of stimulus response curves obtained with transcranial magnetic stimulation from bilateral tibialis anterior muscles post stroke", Neuroscience Letters, (2019), vol. 713, pp. 1-15.
Jaman, R., "A retrospective cross-sectional survey of lumbo-sacral recorded at the D.U.T. Chiropractic Day Clinic (1995-2005)", (2014). Durban University of Technology, Master's Degree in Technology dissertation. Retrieved from the Internet: <URL: https://doi.org/10.51415/10321/221>, 94 pages.
Japanese Patent Office Action in counterpart Japanese Patent Application No. 2017198155 mailed Aug. 20, 2019, 4 pages.
Japanese Patent Office Action in counterpart Japanese Patent Application No. 2017198155 mailed Sep. 11, 2018, 8 pages.
Japanese Patent Office Action in counterpart Japanese Patent Application No. 2021188658 mailed Sep. 4, 2023, 7 pages.
Japanese Patent Office Action in counterpart Japanese Patent Application No. 2021510130 mailed Aug. 21, 2023, 20 pages.
Jenny, A. B. et al., "Principles of Motor Organization of the Monkey Cervical Spinal Cord", The Journal of Neuroscience, (1983), vol. 3, No. 3, pp. 567-575.
Jonic, S. et al., "Three machine learning techniques for automatic determination of rules to control locomotion", IEEE Transactions on Biomedical Engineering, (1999), vol. 46, No. 3, pp. 300-310.
Kim, W. S. et al., "Ultra-sensitive Flexible Pressure Sensor with Stamped Polyurethane Rubber", 2011 11th IEEE Conference on Nanotechnology, (2011), pp. 1607-1610.
Kim, Y. et al., "Electrical behavior of defibrillation and pacing electrodes", Proceedings of the IEEE, (2002), vol. 84, No. 3, pp. 446-456.
Kirazh, O. et al., "Anatomy of the spinal dorsal root entry zone: its clinical significance", Acta Neurochirurgica, (2014), vol. 156, pp. 2351-2358.
Lacour, S. et al., "Flexible and stretchable micro-electrodes for in vitro and in vivo neural interfaces", Medical & Biological Engineering & Computing, (2010), vol. 48, pp. 945-954.
Lacour, S. et al., "Stretchable gold conductors on elastomeric substrates", Applied Physics Letters, (2003), vol. 82, No. 15, pp. 2404-2406.
Levine, A. et al., "Identification of cellular node for motor control pathways", Nature Neuroscience, (2014), vol. 17, No. 4, pp. 586-593.
Lu, D. et al., "Engaging cervical spinal cord networks to re-enable volitional control of hand function in tetraplegic patients", Neurorehabilitation and Neural Repair, (2016), vol. 30, No. 10, pp. 951-962.
Meacham, K. W. et al., "A lithographically-patterned, elastic multi-electrode array for surface stimulation of the spinal cord", Biomed Microdevices, (2008), vol. 10, pp. 259-269.
Metzger, C. et al., "Flexible-foam-based capacitive sensor arrays for object detection at law cost", Applied Physics Letters, American Institute of Physics, (2008), vol. 92, No. 1, pp. 13506-1-13506-3.
Minassian, K. et al., "Human Lumbar Cord Model of the Locomotor Central Pattern Generator", Second Congress International Society of Intraoperative Neurophysiology (ISIN), (2009), pp. 11-13.
Minassian, K. et al., "Neurophysiology of the human lumbar locomotor pattern generator", Proceedings 10th Vienna International Workshop on Functional Electrical Stimulation, Center for Medical Physics and Biomedical Engineering, (2010), pp. 259-261.
Minassian, K. et al., "Posterior root-muscle reflex", Second Congress International Society of Intraoperative Neurophysiology (ISIN), Dubrovnik, Croatia, (2009), pp. 77-80.
Minev, I. R. et al., "Evaluation of an Elastomer Based Gold Microelectrode Array for Neural Recording Applications", Proceedings of the 5th International IEEE/EMBS Conference on Neural Engineering, Cancun, Mexico, (2011), pp. 482-485.
Minev, I. R. et al., "High sensitivity recording of afferent nerve activity using ultra-compliant microchannel electrodes: an acute in vivo validation", Journal of Neural Engineering, (2012), vol. 9, No. 2, pp. 1-7.
Needle, A. R. et al., "Brain Regulation of muscle tone in healthy and functionally unstable ankles", Journal of Sport Rehabilitation, (2013), vol. 22, No. 3, pp. 202-211.
Office Action in U.S. Appl. No. 14/925,791, mailed Jul. 20, 2017, 12 pages.
Office Action in U.S. Appl. No. 15/096,014, mailed Sep. 14, 2017, 13 pages.
Office Action in U.S. Appl. No. 15/713,456, mailed Oct. 24, 2018, 13 pages.
Office Action in U.S. Appl. No. 15/821,076, mailed Oct. 10, 2018, 13 pages.
Office Action in U.S. Appl. No. 17/269,970, mailed Aug. 16, 2023, 7 pages.
Office Action in U.S. Appl. No. 17/407,043, mailed Sep. 13, 2023, 7 pages.
Park, K. J. et al., "Continuous "Over and Over" Suture for Tricuspid Ring Annuloplasty", Korean Journal of Thoracic and Cardiovascular Surgery, (2012), vol. 45, No. 1, pp. 19-23.

(56) References Cited

OTHER PUBLICATIONS

Peachpit, "Working with Basic Shapes in Adobe Illustrator CC (2014 release)," PeachPit, Nov. 3, 2014 [retrieved on Feb. 6, 2024]. Retrieved from the Internet: <URL: https://www.peachpit.com/articles/article.aspx?p=2253413&seqNum=3>.
Pellinen, D.S. et al., "Multifunctional Flexible Parylene-Based Intracortical Microelectrodes", Proceedings of the 2005 IEEE: Engineering in Medicine and Biology 27th Annual Conference, (2005), pp. 5272-5275.
Pflug, H. et al., "Parallel Resonant Inductive Wireless Power Transfer", IEEE, Proceedings of Wireless Power Week 2019, London, United Kingdom (2019), pp. 182-187.
Robinson, A. et al., "Hybrid stretchable circuits on silicone substrate", Journal of Applied Physics, (2014), vol. 115, No. 14, pp. 143511-1-143511-5.
Rubinstein et al., "Current Density Profiles of Surface Mounted and Recessed Electrodes for Neural Prostheses", Biomedical Engineering, IEEE Transactions on BME, (1987), vol. 34, No. 11, pp. 864-875.
Schmidlin, E. et al., "Behavioral Assessment of Manual Dexterity in Non-Human Primates", Journal of Visualized Experiments, (2011), vol. 57, No. e3258, pp. 1-11.
Sharpe, A. et al., "Upper-limb muscles responses to epidural, subdural and intraspinal stimulation of the cervical spinal cord", Journal of Neural Engineering, (2014), vol. 11, No. 1, pp. 1-16.
Sherman, J. et al., "Measurements of the normal cervical spinal cord on MR Imaging", American Journal of Neuroradiology, (1990), vol. 11, No. 2, pp. 369-372.
Suzuki, T. et al., "A 3D flexible parylene probe array for multichannel neural recording", IEEE Neural Engineering, (2003), pp. 154-156.
Takeuchi, S. et al., "3D flexible multichannel neural probe array", Journal of Micromechanics and Microengineering, (2004), vol. 14, No. 1, pp. 104-107.
The State Intellectual Property Office of People's Republic of China Office Action in counterpart Chinese Patent Application No. 201610987062.5 mailed Sep. 30, 2018, 20 pages.
The State Intellectual Property Office of People's Republic of China Office Action in counterpart Chinese Patent Application No. 201780080305.X mailed Aug. 31, 2023, 9 pages.
Tungjitkusolmun, S. et al., "Finite element analyses of uniform current density electrodes for radio-frequency cardiac ablation", IEEE Transactions on Biomedical Engineering, (2000), vol. 47, No. 1, pp. 32-40.
U.S. Appl. No. 15/821,076, filed Nov. 22, 2017, 52 pages.
U.S. Appl. No. 16/153,472, filed Oct. 5, 2018, 51 pages.
U.S. Appl. No. 16/189,655, filed Nov. 13, 2018, 37 pages.
U.S. Appl. No. 61/802,034, filed Mar. 15, 2013, 29 pages.
U.S. Appl. No. 62/171,427, filed Jun. 5, 2015, 55 pages.
U.S. Appl. No. 62/171,436, filed Jun. 5, 2015, 44 pages.
U.S. Appl. No. 62/201,973, filed Aug. 6, 2015, 54 pages.
Valchinov, E. S. et al., "An active electrode for biopotential recording from small localized bio-sources", BioMedical Engineering OnLine, (2004), vol. 3, No. 25, pp. 1-14.
Wang, J. M. et al., "Gaussian process dynamical models for human motion", IEEE Transactions on Pattern Analysis and Machine Intelligence, (2007), vol. 30, No. 2, pp. 283-298.
Ward, A. R. et al., "Sensory, motor, and pain thresholds for stimulation with medium frequency alternating current", Archives of Physical Medicine and Rehabilitation, (1998), vol. 79, No. 3, pp. 273-278.
Wei, P. et al., "Stretchable microelectrode array using room-temperature liquid alloy interconnects", Journal of Micromechanics and Microengineering, (2011), vol. 21, No. 054015, pp. 1-8.
Wiley, J. D. et al., "Analysis and Control of the Current Distribution under Circular Dispersive Electrodes", Biomedical Engineering, IEEE Transactions on BME, (1982), vol. 29, No. 5, pp. 381-385.
YouTube video entitled: "How to Round Corners in Illustrator," uploaded Sep. 6, 2017 by user "Mohamed Achraf" [retrieved on Jul. 7, 2022]. Retrieved from the Internet: <URL:https://www.youtube.com/watch?v=q8Cyd0sqY6A>, 3 pages.
Office Action in U.S. Appl. No. 17/399,780, mailed Jun. 12, 2025, 12 pages.
Non-Final Office Action in U.S. Appl. No. 17/595,384, mailed Jun. 5, 2025, 10 pages.
Aching knee or sore back? New app helps doctors treat pain, medicalxpress.com. May 8, 2017, Retrieved from the Internet: <URL: https://medicalxpress.com/news/2017-05-aching-knee-sore-app-doctors. html>, 1 page.
Back pain and body posture infographic, Alamy.com. Apr. 11, 2017, Retrieved from the Internet: <URL: https://www.alamy.com/stock-photo-back-pain-and-body-posture-infographic-with-anatomical-illustrations-141494074.html?imageid=27CC5905-F123-4DSC-847A4C76D50631C1&p=313080&pn=1&searchld=526c9d4db7f91a3e259d7b785fa370c3&searchtype=0>, 2 pages.
Extended European Search Report in EP25165562.7, mailed Sep. 2, 2025, 9 pages.
Ichiyama et al. "Step training reinforces specific spinal locomotor circuitry in adult spinal rats." Journal of Neuroscience 28.29 (2008): 7370-7375.
Male and female muscle and skeletal systems, Shutterstock.com. Jan. 15, 2021, Retrieved from the Internet: <URL: https://www.shutterstock.com/image-illustration/male-female-muscle-skeletal-systems-xray-1895443960>, 2 pages.
Office Action in U.S. Appl. No. 16/953,322, mailed Aug. 29, 2025, 12 pages.
Office Action in U.S. Appl. No. 18/339,085, mailed Sep. 4, 2025, 15 pages.
Office Action in U.S. Appl. No. 29/874,320, mailed Aug. 18, 2025, 9 pages.
Screenshots of the electric patient-reported outcome app final prototype, Researchgate.net. Oct. 2020, Retrieved from the Internet: <URL: https://www.researchgate.net/figure/Screenshots-of-the-electronic-patient-reported-outcome-appfinal-prototype_fig>, 1 page.
Office Action in U.S. Appl. No. 17/206,007, mailed Dec. 15, 2025, 18 pages.
Office Action in U.S. Appl. No. 17/511,496, mailed Oct. 3, 2025, 17 pages.
Office Action in U.S. Appl. No. 18/297,222, mailed Feb. 12, 2026, 7 pages.
Office Action in U.S. Appl. No. 19/334,188, mailed Jan. 15, 2026, 21 pages.
Office Action in U.S. Appl. No. 19/335,824, mailed Feb. 19, 2026, 10 pages.
Office Action in U.S. Appl. No. 16/953,322, mailed Feb. 2, 2026, 8 pages.

* cited by examiner

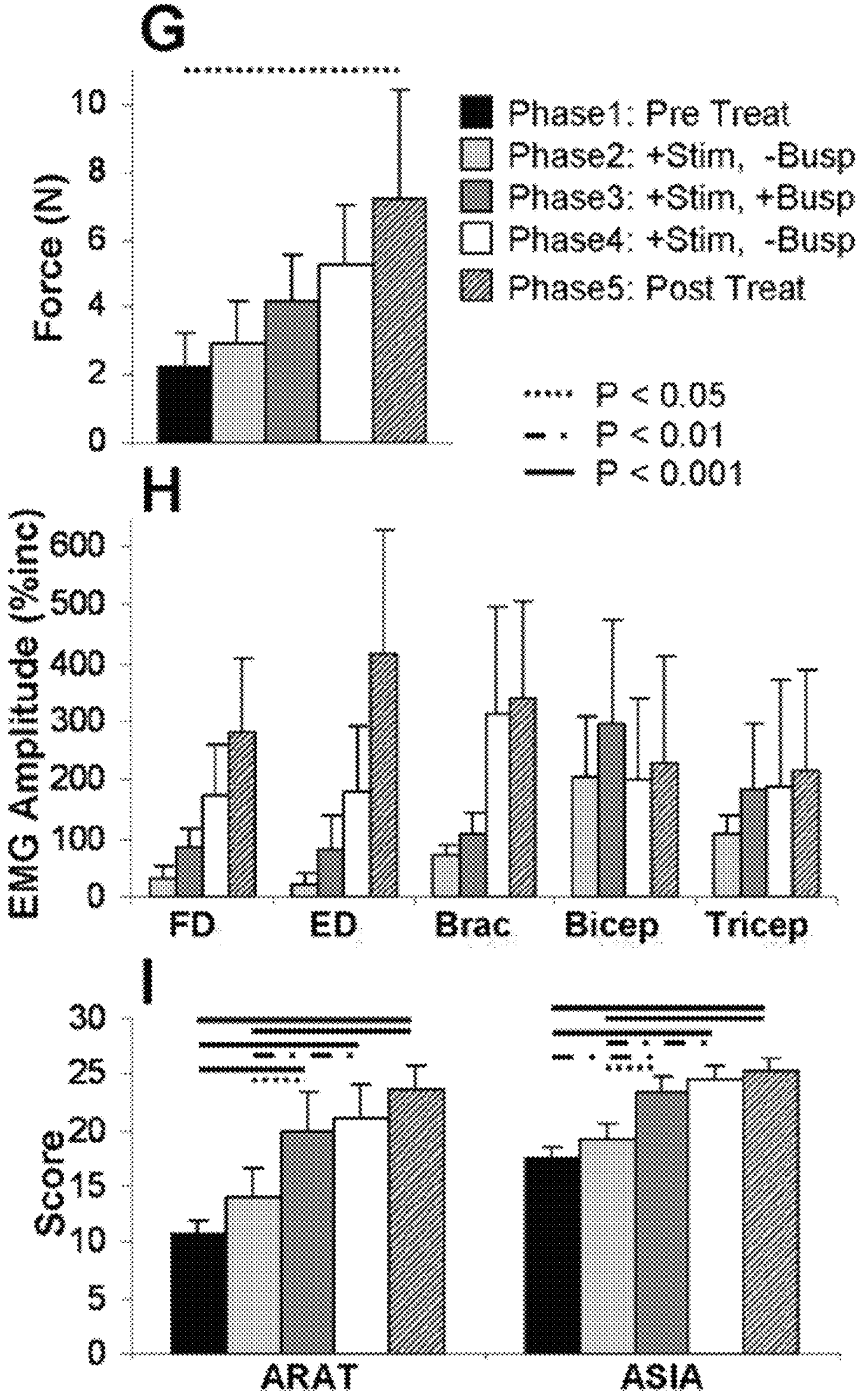
*Fig. 1, cont'd.*

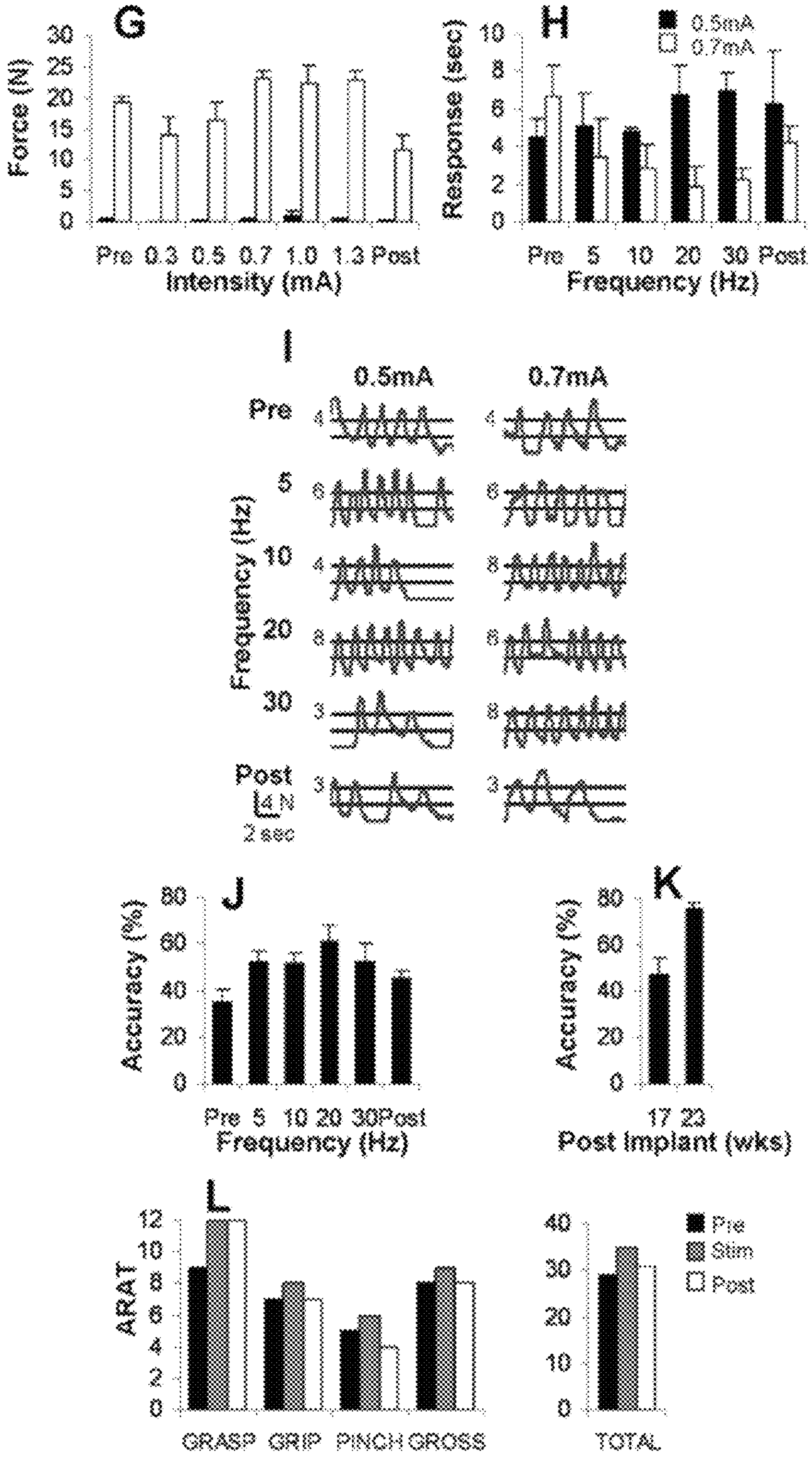
*Fig. 2, cont'd.*

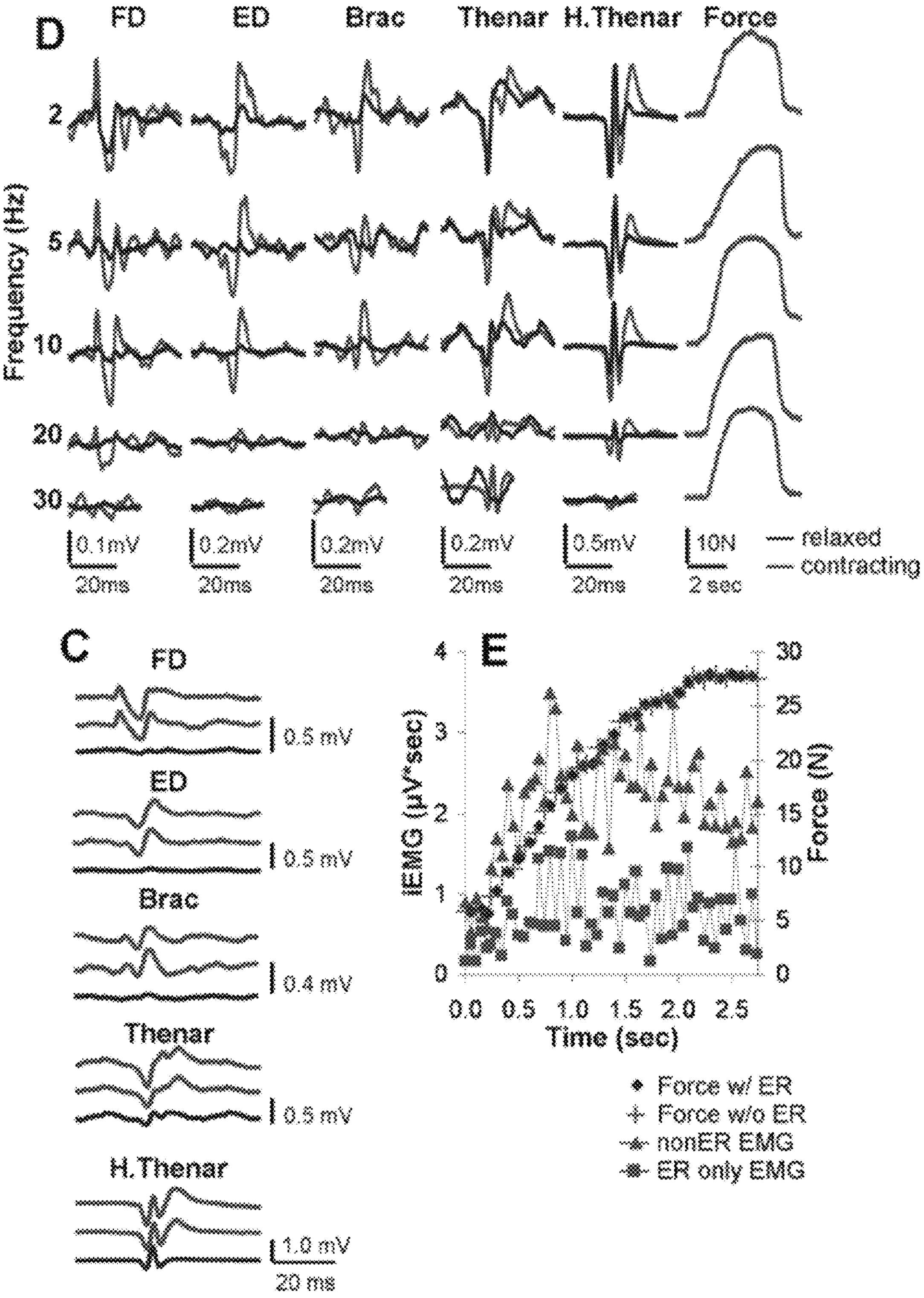
*Fig. 3, cont'd.*

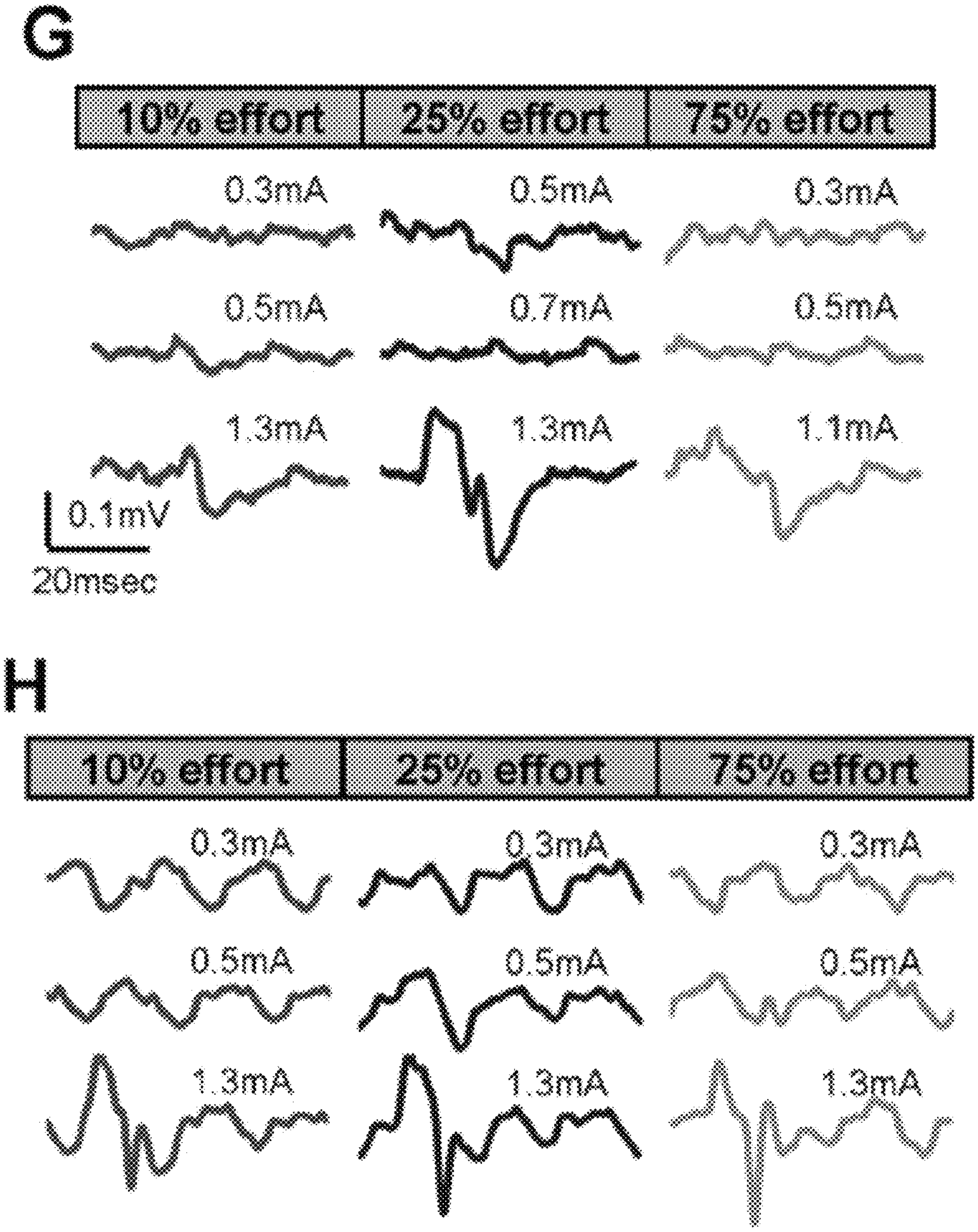
*Fig. 4, cont'd.*

ASIA Upper Limb

| | Beginning of Study | | Conclusion of Study | |
|---|---|---|---|---|
| | L | R | L | R |
| C5 | 3 | 4 | 5 | 5 |
| C6 | 1 | 1 | 4 | 4 |
| C7 | 0 | 0 | 3 | 3 |
| C8 | 0 | 0 | 2 | 2 |
| T1 | 0 | 0 | 2 | 2 |
| Total | 9 | | 32 | |

*Fig. 8*

ENGAGING THE CERVICAL SPINAL CORD CIRCUITRY TO RE- ENABLE VOLITIONAL CONTROL OF HAND FUNCTION IN TETRAPLEGIC SUBJECTS

CROSS-REFERENCE TO RELATED APPLICATIONS

This application is a continuation of U.S. Ser. No. 18/782,349, filed on Jul. 24, 2024, which is a continuation of U.S. Ser. No. 17/407,043, filed on Aug. 19, 2021, now U.S. Pat. No. 12,076,301, which is a continuation of U.S. Ser. No. 16/200,467, filed on Nov. 26, 2018, now U.S. Pat. No. 11,123,312, which is a continuation of U.S. Ser. No. 15/025,201, filed on Mar. 25, 2016, now U.S. Pat. No. 10,137,299, which is a 371 US National Phase of PCT/US2014/057886, filed on Sep. 26, 2014, which claims benefit of and priority to U.S. Ser. No. 61/883,694, filed on Sep. 27, 2013, all of which are incorporated herein by reference in their entirety for all purposes.

STATEMENT OF GOVERNMENTAL SUPPORT

This invention was made with Government support under TR000124, awarded by the National Institutes of Health. The Government has certain rights in the invention.

BACKGROUND

Serious spinal cord injuries (SCI) affect approximately 1.3 million people in the United States, and roughly 12-15.000 new injuries occur each year. Of these injuries, approximately 50% are complete spinal cord injuries in which there is essentially total loss of sensory motor function below the level of the spinal lesion.

Paralysis of the upper limbs results in an enormous loss of independence of one's daily life. Meaningful improvement in hand function is generally rare after one year of tetraparesis.

SUMMARY

In various embodiments, methods are provided for applying spinal cord stimulation with and without selective pharmaceuticals to restore voluntary control of hand function in tetraplegic subjects. The spinal cord stimulation can be transcutaneous and/or epidural. In various embodiments the electrical stimulation alone or in combination with pharmaceuticals can be applied to facilitate restoration of motor control and/or force generation in subjects suffering with spinal cord injury and/or as other neurological injury and illness that effects motor control of the hand or paw. Successful application can provide a device for widespread use in rehabilitation of neurologic injury and disease.

In particular illustrative embodiments, the devices, optional pharmacological agents, and methods described herein stimulate the spinal cord with, e.g., electrodes that modulate the proprioceptive and supraspinal information that controls the hands during reaching and/or grasping and/or manipulating conditions. Without being bound by a particular theory, it is believed the proprioceptive and cutaneous sensory information guides the activation of the muscles in a coordinated manner and in a manner that accommodates the external conditions.

Unlike approaches that involve specific stimulation of motor neurons to directly induce a movement, the methods described herein can enable the spinal circuitry to control the movements. More specifically, the devices, optional pharmacological agents, and methods described herein can exploit the spinal circuitry and its ability to interpret proprioceptive information and to respond to that proprioceptive information in a functional way. In various embodiments, this is in contrast to other approaches where the actual movement is induced/controlled by direct stimulation (e.g., of particular motor neurons).

Accordingly, in various aspects, the invention(s) contemplated herein may include, but need not be limited to, any one or more of the following embodiments:

Embodiment 1: A method of improving motor control and/or strength in a hand of a subject with a neuromotor disorder affecting motor control of the hand, said method including: neuromodulating the cervical spinal cord of the subject by administering stimulation to the cervical spinal cord or a region thereof; and by administering to the subject at least one monoaminergic agonist. In some instances of Embodiment 1, the spinal cord stimulation can be transcutaneous and/or epidural.

Embodiment 2: The method of embodiment 1, wherein said method includes administering transcutaneous stimulation to the cervical spinal cord or a region thereof.

Embodiment 3: The method of embodiment 1, wherein said method includes administering epidural stimulation to the cervical spinal cord or a region thereof.

Embodiment 4: The method of embodiment 1, wherein said method includes administering a monoaminergic agonist to said subject.

Embodiment 5: The method of embodiment 1, wherein said method includes administering transcutaneous stimulation to the cervical spinal cord or a region thereof in conjunction with administration of a monoaminergic agonist.

Embodiment 6: The method of embodiment 1, wherein said method includes administering epidural stimulation to the cervical spinal cord or a region thereof in conjunction with administration of a monoaminergic agonist.

Embodiment 7: The method of embodiment 1, wherein said method includes administering transcutaneous stimulation to the cervical spinal cord or a region thereof in conjunction with epidural stimulation of the cervical spinal cord or a region thereof.

Embodiment 8: The method of embodiment 1, wherein said method includes administering transcutaneous stimulation to the cervical spinal cord or a region thereof in conjunction with epidural stimulation of the cervical spinal cord or a region thereof in conjunction with administration of a monoaminergic agonist to said subject.

Embodiment 9: The method according to any one of embodiments 1, 2, 5, 7, and 8, wherein said transcutaneous stimulation is at a frequency ranging from about 3 Hz, or from about 5 Hz, or from about 10 Hz to about 100 Hz, or to about 80 Hz, or to about 40 Hz, or from about 3 Hz or from about 5 Hz to about 80 Hz, or from about 5 Hz to about 30 Hz, or to about 40 Hz, or to about 50 Hz.

Embodiment 10: The method according to any one of embodiments 1, 2, 5, and 7-9, wherein said transcutaneous stimulation is applied at an intensity ranging from about 10 mA to about 150 mA, or from about 20 mA to about 50 mA or to about 100 mA, or from about 20 mA or from about 30 mA, or from about 40 mA to about 50 mA, or to about 60 mA, or to about 70 mA or to about 80 mA.

Embodiment 11: The method according to any one of embodiments 1, 2, 5, and 7-10, wherein said transcutaneous stimulation is at a frequency and amplitude sufficient to improve hand strength and/or fine hand control.

Embodiment 12: The method according to any one of embodiments 1, 2, 5, and 7-11, wherein said transcutaneous stimulation is applied to the dorsal aspect of the neck in the area of C5.

Embodiment 13: The method according to any one of embodiments 1, 3, and 6-12, wherein said epidural stimulation is at a frequency ranging from about 3 Hz, or from about 5 Hz, or from about 10 Hz to about 100 Hz, or to about 80 Hz, or to about 40 Hz, or from about 3 Hz or from about 5 Hz to about 80 Hz, or from about 5 Hz to about 30 Hz, or to about 40 Hz, or to about 50 Hz.

Embodiment 14: The method according to any one of embodiments 1, 3, and 6-13, wherein said epidural stimulation is at an amplitude ranging from 0.05 mA to about 30 mA, or from about 0.1 mA to about 20 mA, or from about 0.1 mA to about 15 mA or to about 10 mA.

Embodiment 15: The method according to any one of embodiments 1, 3, and 6-14, wherein said pulse width ranges from about 150 μs to about 600 μs, or from about 200 μs to about 500 μs, or from about 200 μs to about 450 μs.

Embodiment 16: The method according to any one of embodiments 1, 3, and 6-15, wherein said epidural stimulation is at a frequency and amplitude sufficient to improve hand strength and/or fine hand control.

Embodiment 17: The method according to any one of embodiments 1, 3, and 6-16, wherein said epidural stimulation is applied paraspinally over vertebrae spanning C2 to T1.

Embodiment 18: The method according to any one of embodiments 1, 3, and 6-16, wherein said epidural stimulation is applied paraspinally over vertebrae spanning C5 to T1.

Embodiment 19: The method according to any one of embodiments 1, 3, and 6-18, wherein said epidural stimulation is applied via a permanently implanted electrode array.

Embodiment 20: The method of embodiment 19, wherein said electrode array is a parylene based microelectrode implant.

Embodiment 21: The method according to any one of embodiments 1, 4, 5, 6, and 8-20, wherein the at least one monoaminergic agonist includes a drug selected from the group consisting of a serotonergic drug, a dopaminergic drug, a noradrenergic drug, a GABAergic drug, and a glycinergic drug.

Embodiment 22: The method of embodiment 21, where the agent is selected from the group consisting of 8-hydroxy-2-(di-n-propylamino)tetralin (8-OH-DPAT), 4-(benzodioxan-5-yl)1-(indan-2-yl)piperazine (S15535), N-{2-[4-(2-methoxyphenyl)-1-piperazinyl] ethyl}-N-(2-pyridinyl)cyclo-hexanecarboxamide (WAY 100.635). Quipazine, Ketanserin, 4-amino-(6-chloro-2-pyridyl)-1 piperidine hydrochloride (SR 57227A), Ondanesetron, Buspirone, Methoxamine, Prazosin, Clonidine, Yohimbine, 6-chloro-1-phenyl-2, 3,4,5-tetrahydro-1H-3-benzazepine-7,8-diol (SKF-81297), 7-chloro-3-methyl-1-phenyl-1,2,4,5-tetrahydro-3-benzazepin-8-ol (SCH-23390), Quinpirole, and Eticlopride.

Embodiment 23: The method of embodiment 21, wherein said monoaminergic agonist is buspirone.

Embodiment 24: The method of embodiment 22, wherein said drug is 8-hydroxy-2-(di-n-propylamino)tetralin (8-OH-DPAT).

Embodiment 25: The method of embodiment 22, wherein said drug is 4-(benzodioxan-5-yl)1-(indan-2-yl)piperazine (S15535).

Embodiment 26: The method of embodiment 22, wherein said drug is N-{2-[4-(2-methoxyphenyl-1-piperazinyl] ethyl}-N-(2-pyridinyl)cyclo-hexanecarboxamide (WAY 100.635).

Embodiment 27: The method of embodiment 22, wherein said drug is Quipazine.

Embodiment 28: The method of embodiment 22, wherein said drug is Ketanserin.

Embodiment 29: The method of embodiment 22, wherein said drug is 4-amino-(6-chloro-2-pyridyl)-1 piperidine hydrochloride (SR 57227A).

Embodiment 30: The method of embodiment 22, wherein said drug is Ondanesetron.

Embodiment 31: The method of embodiment 22, wherein said drug is Methoxamine.

Embodiment 32: The method of embodiment 22, wherein said drug is Prazosin.

Embodiment 33: The method of embodiment 22, wherein said drug is Clonidine.

Embodiment 34: The method of embodiment 22, wherein said drug is Yohimbine.

Embodiment 35: The method of embodiment 22, wherein said drug is 6-chloro-1-phenyl-2.

Embodiment 36: The method of embodiment 22, wherein said drug is 3,4,5-tetrahydro-1H-3-benzazepine-7.

Embodiment 37: The method of embodiment 22, wherein said drug is 8-diol (SKF-81297).

Embodiment 38: The method of embodiment 22, wherein said drug is 7-chloro-3-methyl-1-phenyl-1,2,4,5-tetrahydro-3-benzazepin-8-ol (SCH-23390).

Embodiment 39: The method of embodiment 21, wherein said drug is Quinpirole.

Embodiment 40: The method of embodiment 21, wherein said drug is and Eticlopride.

Embodiment 41: The method according to any one of embodiments 1 and 4-40, wherein a combination of transcutaneous and/or epidural stimulation and monoaminergic agonist provides a synergistic improvement in hand strength and/or fine hand control.

Embodiment 42: The method according to any one of embodiments 1-41, wherein said subject is a human. In some embodiments, the subject is a non-human mammal.

Embodiment 43: The method according to any one of embodiments 1-42, wherein said subject has a spinal cord injury.

Embodiment 44: The method of embodiment 43, wherein said spinal cord injury is clinically classified as motor complete.

Embodiment 45: The method of embodiment 43, wherein said spinal cord injury is clinically classified as motor incomplete.

Embodiment 46: The method according to any one of embodiments 1-42, wherein said subject has an ischemic brain injury.

Embodiment 47: The method of embodiment 46, wherein said ischemic brain injury is brain injury from stroke or acute trauma.

Embodiment 48: The method according to any one of embodiments 1-42, wherein said mammal has a neurodegenerative pathology.

Embodiment 49: The method of embodiment 48, wherein said neurodegenerative pathology is associated with a condition selected from the group consisting of Parkinson's disease. Huntington's disease, Alzheimer's disease, amyotrophic lateral sclerosis (ALS), primary lateral sclerosis (PLS), dystonia, and cerebral palsy.

Embodiment 50: The method according to any one of embodiments 1-49, wherein the stimulation is under control of the subject.

Embodiment 51: The method according to any one of embodiments 1-50, wherein said method further includes physical training of said subject.

Embodiment 52: The method of embodiment 51, wherein said physical training includes hand contraction against a resistance.

Embodiment 53: The method according to any one of embodiments 51-52, wherein said physical training includes tracing a displayed pattern by hand manipulation of a hand controller.

Embodiment 54: An electrical stimulator configured to induce epidural and/or transcutaneous electrical stimulation in the cervical region of a mammal according to any one of embodiments 1-20.

DEFINITIONS

As used herein "electrical stimulation" or "stimulation" means application of an electrical signal that may be either excitatory or inhibitory to a muscle or neuron and/or to groups of neurons and/or interneurons. It will be understood that an electrical signal may be applied to one or more electrodes with one or more return electrodes.

As used herein "epidural" means situated upon the dura or in very close proximity to the dura. The term "epidural stimulation" refers to electrical epidural stimulation. In certain embodiments epidural stimulation is referred to as "electrical enabling motor control" (eEmc).

The term "transcutaneous stimulation" or "transcutaneous electrical stimulation" or "cutaneous electrical stimulation" refers to electrical stimulation applied to the skin, and, as typically used herein refers to electrical stimulation applied to the skin in order to effect stimulation of the spinal cord or a region thereof. The term "transcutaneous electrical spinal cord stimulation" may also be referred to as "tSCS". The term "pcEmc" refers to painless cutaneous electrical stimulation.

The term "motor complete" when used with respect to a spinal cord injury indicates that there is no motor function below the lesion, (e.g., no movement can be voluntarily induced in muscles innervated by spinal segments below the spinal lesion.

The term "monopolar stimulation" refers to stimulation between a local electrode and a common distant return electrode.

The term "co-administering", "concurrent administration", "administering in conjunction with" or "administering in combination" when used, for example with respect to transcutaneous electrical stimulation, epidural electrical stimulation, and pharmaceutical administration, refers to administration of the transcutaneous electrical stimulation and/or epidural electrical stimulation and/or pharmaceutical such that various modalities can simultaneously achieve a physiological effect on the subject. The administered modalities need not be administered together, either temporally or at the same site. In some embodiments, the various "treatment" modalities are administered at different times. In some embodiments, administration of one can precede administration of the other (e.g., drug before electrical stimulation or vice versa). Simultaneous physiological effect need not necessarily require presence of drug and the electrical stimulation at the same time or the presence of both stimulation modalities at the same time. In some embodiments, all the modalities are administered essentially simultaneously.

Figure 1:
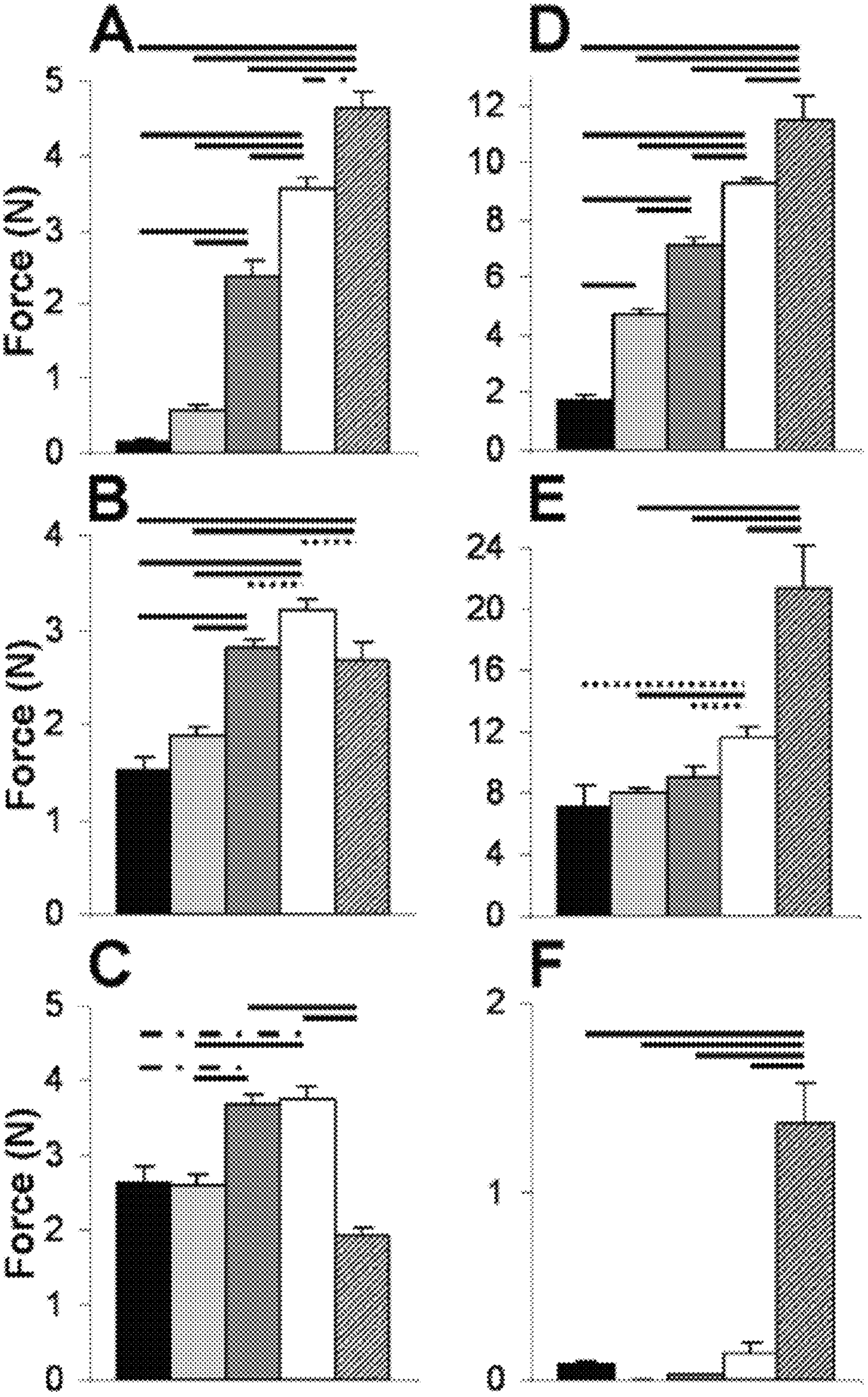
FIG. 1, panels A-I, illustrates improvement in hand function with interventions. Assessments of grip strength were made in 6 paralyzed subjects on 6 days of testing over 6 weeks Pre-Treatment (Phase 1. Pre Treat), followed by 4 days of testing over 2 weeks with pcEMC (Phase 2, +Stim, +Busp), followed by 4 days of testing over 2 weeks with pcEMC plus oral buspirone (Phase 3, +Stim, +Busp), followed by 4 days of testing over 2 weeks with pcEmc plus placebo (Phase 4, +Stim, −Busp), and followed by 4 days of testing over 2 weeks Post-Treatment after a 3-6 month delay (Phase 5, Post Treat) (Panels A-F). Mean (t SEM) grip strength for all 6 subjects (G), EMG amplitudes as percent increase over baseline (Pre Treat) levels (panel H), American Spinal Injury Assessment (ASIA), and Action Research Arm Test (ARAT) (Carroll (1965) J. Chronic Dis., 18: 479-491) functional scores (panel I) are shown. Horizontal lines indicate significant differences at P<0.05, P<0.01, or PC 0.001. FD, flexor digitorum; ED, extensor digitorum; Brac, brachioradialis; Bicep, biceps brachii; tricep, triceps brachii.

The ASIA upper limb assessment, a standard assessment used to evaluate motor and sensory function in individuals with SCI, focuses on myotomes (muscle groups) corresponding to nerve roots. Five key myotomes (C5-T1) are evaluated per upper limb.

C5—Elbow flexors (biceps brachii and brachialis)
C6—Wrist extensors (extensor carpi radialis longus and brevis)
C7—Elbow extensors (triceps brachii)
C8—Finger flexors (flexor digitorum profundus)
T1—Finger abductors (abductor digiti minimi)

Each myotome is tested bilaterally for strength using a 6-point scale (0-5).

0—Total paralysis.
1—Palpable or visible contraction, no movement.
2—Active movement, full range of motion (ROM) with gravity eliminated.

3—Active movement, full ROM against gravity.

4—Active movement, full ROM against gravity and moderate resistance.

5—Normal movement, full ROM against gravity and full resistance.

FIG. 8 shows upper extremity motor ASIA Impairment Score of Subject E. Motor function was assessed at the beginning and conclusion of the study, demonstrating a clinically significant 23-point increase during the study period with improvements in each myotome. Myotome C5 (biceps) progressed from active movement against gravity (left) or light resistance (right) to full resistance bilaterally. Myotome C6 (wrist extensors) progressed from palpable contraction with no movement to active movement with full ROM with moderate resistance. Significantly, Subject E showed total paralysis (score 0) for each of myotomes C7, C8 and T1 at the beginning of the study and ended with active movement and full ROM against gravity for C7 (triceps) and active movement and full ROM with gravity eliminated for finger myotomes (C8 and T1).

DETAILED DESCRIPTION

Embodiments described herein provide methods for applying spinal cord stimulation with and without selective pharmaceuticals to restore voluntary control of upper extremity function in tetraplegic subjects. In some embodiments, the upper extremity or extremities can be the hands. The spinal cord stimulation can be transcutaneous, epidural, or a combination thereof. The spinal cord stimulation alone or in combination with pharmaceuticals can be applied to facilitate restoration of motor control and/or force generation in individuals with spinal cord injuries.

As demonstrated herein in the Examples, an injured cervical spinal cord (e.g., a human cervical spinal cord) can be modulated using painless cutaneous electrical stimulation (pcEmc) monoaminergic agonist (fEmc) treatment, and/or eEmc to regain voluntary hand function. In some embodiments, mean hand strength can be increased by greater than 300% after pcEmc plus fEmc (buspirone) treatment. This was demonstrated in 6 subjects with a chronic motor complete cervical injury. One subject that was implanted with a cervical epidural electrode array realized significantly improved hand strength and fine hand control in the presence of cervical eEmc. Thus, the cervical circuitry can be neuromodulated to improve volitional control of hand function in tetraplegic subjects with one or more interventions: transcutaneous electrical stimulation (e.g., pcEMC), and/or monoaminergic agonist administration (fEmc), and/or epidural electrical stimulation (eEmc). In some embodiments, the impact of the herein described methods on individuals with upper limb paralysis can be dramatic functionally, psychologically, and economically.

Accordingly, in various embodiments, methods are provided for improving motor control and/or strength in a hand (or paw) of a subject with a neuromotor disorder affecting motor control of the hand (or paw). In various embodiments, the methods involve neuromodulating the cervical spinal cord of the subject by administering transcutaneous stimulation to the cervical spinal cord or a region thereof; and/or neuromodulating the cervical spinal cord of said subject by administering epidural stimulation to the cervical spinal cord or a region thereof; and/or by administering to the subject a monoaminergic agonist (or other neuromodulatory pharmaceutical).

In some embodiments, neuromodulatory strategies can be used to improve fine motor control of the upper limbs, i.e., performance of motor tasks considered to be less "automatic" than posture and locomotion. These strategies can neuromodulate the lumbosacral spinal circuitry via epidural stimulation (electrical enabling motor control, eEmc)

In various embodiments, these methods can, optionally, be used in combination with physical training regimen. And in some embodiments, the pharmaceutical can be buspirone.

The methods described herein are for use with a mammal (e.g., a human, a mammal (e.g., a non-human primate, equine, feline, canus, etc.) who has a spinal cord with at least one dysfunctional spinal circuit that inhibits motor control and/or strength in a hand or paw and/or who exhibits another neuropathology that inhibits motor control and/or strength in a hand or paw. In one embodiment, the mammal is a human. As described herein, ranscutaneous electrical stimulation of the cervical spinal cord or a region thereof, and/or epidural stimulation of the cervical spinal cord, or a region thereof, and/or use of a neuromodulatory agent (e.g., a monoaminergic agent) can improve and/or restore motor control and/or strength to a hand or paw.

In some embodiments, hand function can be improved by neuromodulating the cervical spinal cord. Six subjects with chronic (18-36 months) spinal cord injury (SCI, traumatic cervical injury. ASIA B with no motor strength below the injury) were tested. All subjects initially had minimal hand strength, a condition characteristic of the majority of cervical SCI patients. The experimental approach began with six weeks of baseline testing (Phase 1), followed by three 2-week treatment periods (phases 2-4), and then by a period of approximately three months without any treatment at the end of which there was a final two week testing period (Phase 5). pcEmc at the C5 spinal segment (Phase 2) increased hand strength in 4/6 subjects compared to baseline Phase 1. During buspirone treatment (Phase 3), 4/6 subjects increased hand strength compared to Phase 1 and 2. The next 2 weeks buspirone was withdrawn but pcEmc continued (Phase 4), and again 4/6 subjects showed further improvement in grip strength compared to Phase 3. For all subjects combined, the mean grip strength tended to increase after each successive treatment phase. EMG amplitudes were generally consistent with increases in grip force, i.e., digit flexor and extensor EMG amplitudes tended to increase progressively across phases. After approximately three months without treatment, 4/6 subjects improved their performance relative to Phase 4.

These results show that the cervical spinal cord can be neuromodulated using two paradigms, i.e., electrically and pharmacologically. Moreover, these data indicate that non-functional networks can become engaged and progressively improve motor performance. In addition, the further improvement in hand function after withdrawing pcEMC and fEMC suggests that once functional connections are established they remain active.

Accordingly, the methods described herein are useful to improve and/or restore motor function to the hand or paw of a subject having paralysis affecting that hand or paw. In various embodiments, the methods provide that the spinal circuitry is neuromodulated to a physiological state that facilitates or enables the recovery or improved control of movement or improved strength of a hand or paw following some neuromotor dysfunction.

In some embodiments the paralysis effecting the hand or paw may be a motor complete paralysis or a motor incomplete paralysis. In certain embodiments the paralysis may have been caused by a spinal cord injury classified as motor complete or motor incomplete. The paralysis may have been caused by an ischemic or traumatic brain (or spinal) injury.

In certain embodiments the paralysis may have been caused by an ischemic brain injury resulting from a stroke or acute trauma. By way of another example, the paralysis may have been caused by a neurodegenerative condition affecting the brain and/or spinal cord. In certain embodiments the neurodegenerative injury may be associated with a disease such as Parkinson's disease, Huntington's disease, Alzheimer's disease, frontotemporal dementia, dystonia, amyotrophic lateral sclerosis (ALS), primary lateral sclerosis (PLS), and other conditions such as cerebral palsy and multiple sclerosis (MS).

By way of non-limiting example, in certain embodiments, the methods described herein comprises application of electrical stimulation to the cervical spinal cord or a portion thereof of the subject. The electrical stimulation may be applied by a surface electrode(s) that is applied to the skin surface of the subject to provide a transcutaneous stimulation. Additionally, or alternatively, the electrical stimulation can be provided epidurally (e.g., via an implanted electrode or electrode array).

In various embodiments, the electrodes may; be implanted along, and/or the stimulation may be applied to the entire cervical spine (e.g., C1-T1) or to a region therein (e.g., C2-C7, C3-C7, C3-C6, C3-C5, C4-C7, C4-C6, C4-C5, C5, etc.). The electrical stimulation is delivered, e.g., as described herein (e.g., at 5-40 Hz at 20-100 mA). While not a requirement, the electrical stimulation may not directly activate muscle cells in the portion of the patient's body having the paralysis. In certain embodiments the electrodes (surface and/or implanted) may include an array of one or more electrodes stimulated in a monopolar biphasic configuration.

In various embodiments, the stimulation may include tonic stimulation and/or intermittent stimulation. The stimulation may include simultaneous or sequential stimulation, or combinations thereof, of different cord regions (e.g., different regions within the cervical spinal cord, or a region within the cervical spinal cord and other regions outside the cervical spinal cord). Optionally, in certain embodiments, the stimulation pattern may be under control of the subject.

In certain embodiments, the method(s) may include administering one or more neuropharmaceutical agents to the subject. The neuropharmaceutical agents may include, for example, a monoaminergic agent (e.g., buspirone).

In certain embodiments, the electrical stimulation is defined by a set of parameter values (e.g., frequency, amplitude, pulse width, etc.), and activation of the selected spinal circuit may (but need not) generate a quantifiable result. Optionally, the method may be repeated using electrical stimulation having different sets of parameter values to obtain quantifiable results generated by each repetition of the method. In certain embodiments a machine learning method may be executed by at least one computing device. The machine learning method builds a model of a relationship between the electrical stimulation applied to the spinal cord and the quantifiable results generated by activation of the at least one spinal circuit. A new set of parameters may be selected based on the model. By way of a non-limiting example, the machine learning method may implement a Gaussian Process Optimization, e.g., as described in PCT Publication No: WO/2012/094346 (PCT/US2012/020112).

In various embodiments, the methods described herein may further incorporate physical training. In certain embodiments, the physical training may include inducing a resistance-providing positional change in the region of the subject where locomotor activity is to be facilitated (e.g., the hand and/or finger(s)). The positional change in the subject may include, but need not be limited to grasping and/or tracking. In certain embodiments, the physical training may include robotically guided training.

Another exemplary embodiment is a method that includes placing an electrode on the subject's cervical spinal cord, positioning the patient in a training device configured to assist with physical training that is configured to induce neurological signals in the hand or paw, and applying electrical stimulation to a portion of the cervical spinal cord of the subject.

Transcutaneous Stimulation of a Region of the Cervical Spine.

The location of the electrode and its stimulation parameters are important in defining motor response. Use of surface electrode(s), as described herein, facilitates selection or alteration of particular stimulation sites as well as the application of a wide variety of stimulation parameters. Additionally surface stimulation can be used to optimize location for an implantable electrode or electrode array for epidural stimulation.

In various embodiments, the methods described herein involve transcutaneous electrical stimulation of the cervical spine or a region of the cervical spine of the subject. Illustrative regions include, but are not limited to one or more regions straddling or spanning a region selected from the group consisting of C1-C1, C1-C2, C1-C3, C1-C4, C1-C7, C1-C6, C1-C7, C1-T1, C2-C2, C2-C3, C2-C4, C2-C5, C2-C6, C2-C7, C2-T1, C3-C3, C3-C4, C3-C5, C3-C6, C3-C7, C3-T1, C4-C4, C4-C5, C4-C6, C4-C7, C4-T1, C5-C5, C5-C6, C5-C7, C5-T1, C6-C6, C6-C7, C6-T1, C7-C7, and C7-T1.

In certain embodiments, the stimulation is stimulation at a frequency ranging from about 3 Hz, or from about 5 Hz, or from about 10 Hz to about 100 Hz, or to about 80 Hz, or to about 40 Hz, or from about 3 Hz or from about 5 Hz to about 80 Hz, or from about 5 Hz to about 30 Hz, or to about 40 Hz, or to about 50 Hz.

In certain embodiments, the transcutaneous stimulation is applied at an intensity ranging from about 10 mA to about 150 mA, or from about 20 mA to about 50 mA or to about 100 mA, or from about 20 mA or from about 30 mA, or from about 40 mA to about 50 mA, or to about 60 mA, or to about 70 mA or to about 80 mA.

In certain embodiments, the transcutaneous stimulation is at a frequency and amplitude sufficient to improve hand strength and/or fine hand control when applied in conjunction with a neuromodulatory agent (e.g., a monoaminergic agent). In certain embodiments the transcutaneous stimulation is at a frequency and amplitude sufficient to improve hand strength and/or fine hand control when applied in conjunction with an epidural stimulation of the cervical spinal cord or a region thereof. In certain embodiments the transcutaneous stimulation is at a frequency and amplitude sufficient to improve hand strength and/or fine hand control when applied in conjunction with a neuromodulatory agent (e.g., a monoaminergic agent) and epidural stimulation of the cervical spinal cord or a region thereof. In certain embodiments the transcutaneous stimulation is at a frequency and amplitude sufficient to improve hand strength and/or fine hand control when utilized without epidural stimulation and/or without a neuromodulatory agent.

Epidural Stimulation of a Region of the Cervical Spine

In various embodiments, the methods described herein involve epidural electrical stimulation of the cervical spine or a region of the cervical spine of the subject. Illustrative regions include, but are not limited to, one or more regions straddling or spanning a region selected from the group consisting of C1-C1, C1-C2, C1-C3, C1-C4, C1-C7, C1-C6, C1-C7, C1-T1, C2-C2, C2-C3, C2-C4, C2-C5, C2-C6, C2-C7, C2-T1, C3-C3, C3-C4, C3-C5, C3-C6, C3-C7, C3-T1, C4-C4, C4-C5, C4-C6, C4-C7, C4-T1, C5-C5, C5-C6, C5-C7, C5-T1, C6-C6, C6-C7, C6-T1, C7-C7, and C7-T1.

In certain embodiments, the epidural stimulation is at a frequency ranging from about 3 Hz, or from about 5 Hz, or from about 10 Hz to about 100 Hz, or to about 80 Hz, or to about 40 Hz, or from about 3 Hz or from about 5 Hz to about 80 Hz, or from about 5 Hz to about 30 Hz, or to about 40 Hz, or to about 50 Hz.

In certain embodiments, the epidural stimulation is at an amplitude ranging from 0.05 mA to about 30 mA, or from about 0.1 mA to about 20 mA, or from about 0.1 mA to about 15 mA or to about 10 mA.

In certain embodiments, the pulse width ranges from about 150 μs to about 600 μs, or from about 200 μs to about 500 μs, or from about 200 μs to about 450 μs.

In certain embodiments, the epidural stimulation is at a frequency and amplitude sufficient to improve hand strength and/or fine hand control. In certain embodiments the epidural stimulation is applied paraspinally over a cervical region identified above (e.g., over vertebrae spanning C2 to T1, over vertebrae spanning C5 to T1, etc.).

In certain embodiments, the epidural stimulation is applied via a permanently implanted electrode array (e.g., a typical density electrode array, a high density electrode array, etc.).

In certain embodiments, the epidural electrical stimulation is administered via a high density epidural stimulating array (e.g., as described in PCT Publication No: WO/2012/094346 (PCT/US2012/020112). In certain embodiments, the high density electrode arrays are prepared using microfabrication technology to place numerous electrodes in an array configuration on a flexible substrate. In some embodiments, epidural array fabrication methods for retinal stimulating arrays can be used in the methods described herein (see, e.g., Maynard (2001) *Annu. Rev. Biomed. Eng.,* 3: 145-168; Weiland and Humayun (2005) *IEEE Eng. Med. Biol. Mag.,* 24(5): 14-21, and U.S. Patent Publications 2006/0003090 and 2007/0142878). In various embodiments, the stimulating arrays comprise one or more biocompatible metals (e.g., gold, platinum, chromium, titanium, iridium, tungsten, and/or oxides and/or alloys thereof) disposed on a flexible material. Flexible materials can be selected from parylene A, parylene C, parylene AM, parylene F, parylene N, parylene D, other flexible substrate materials, or combinations thereof. Parylene has the lowest water permeability of available microfabrication polymers, is deposited in a uniquely conformal and uniform manner, has previously been classified by the FDA as a United States Pharmacopeia (USP) Class VI biocompatible material (enabling its use in chronic implants) (Wolgemuth, Medical Device and Diagnostic Industry, 22(8): 42-49 (2000)), and has flexibility characteristics (Young's modulus ~4 GPa (Rodger and Tai (2005) *IEEE Eng. Med. Biology,* 24(5): 52-57)), lying in between those of PDMS (often considered too flexible) and most polyimides (often considered too stiff). Finally, the tear resistance and elongation at break of parylene are both large, minimizing damage to electrode arrays under surgical manipulation. The preparation and parylene microelectrode arrays suitable for use in the epidural stimulation methods described herein is described in PCT Publication No: WO/2012/100260 (PCT/US2012/022257).

The electrode array may be implanted using any of a number of methods (e.g., a laminectomy procedure) well known to those of skill in the art.

In various embodiments, the arrays are operably linked to control circuitry that permits selection of electrode(s) to activate/stimulate and/or that controls frequency, and/or pulse width, and/or amplitude of stimulation. In various embodiments, the electrode selection, frequency, amplitude, and pulse width are independently selectable, e.g., at different times, different electrodes can be selected. At any time, different electrodes can provide different stimulation frequencies and/or amplitudes. In various embodiments, different electrodes or all electrodes can be operated in a monopolar mode and/or a bipolar mode, using constant current or constant voltage delivery of the stimulation.

In certain embodiments, the electrodes can also be provided with implantable control circuitry and/or an implantable power source. In various embodiments, the implantable control circuitry can be programmed/reprogrammed by use of an external device (e.g., using a handheld device that communicates with the control circuitry through the skin). The programming can be repeated as often as necessary.

Any present or future developed stimulation system capable of providing an electrical signal to one or more regions of the cervical spinal cord may be used in accordance with the teachings provided herein. In various embodiments, the system may comprise an external pulse generator. In other embodiments the system may comprise an implantable pulse generator to produce a number of stimulation pulses that are sent to the a region in proximity to the cervical spinal cord by insulated leads coupled to the spinal cord by one or more electrodes and/or an electrode array. In certain embodiments the one or more electrodes or one or more electrodes comprising the electrode array may be attached to separate conductors included within a single lead. Any known or future developed lead useful for applying an electrical stimulation signal in proximity to a subject's spinal cord may be used. For example, the leads may be conventional percutaneous leads, such as PISCES® model 3487A sold by Medtronic. Inc. In some embodiments, it may be desirable to employ a paddle-type lead.

Any known or future developed external or implantable pulse generator may be used in accordance with the teachings provided herein. For example, one internal pulse generator may be an ITREL® II or Synergy pulse generator available from Medtronic, Inc, Advanced Neuromodulation Systems, Inc.'s GENESIS™ pulse generator, or Advanced Bionics Corporation's PRECISION™ pulse generator. One of skill in the art will recognize that the above-mentioned pulse generators may be advantageously modified to deliver therapy in accordance with the teachings provided herein.

In certain embodiments systems can employ a programmer coupled via a conductor to a radio frequency antenna. This system permits attending medical personnel to select the various pulse output options after implant using radio frequency communications. While, in certain embodiments, the system employs fully implanted elements, systems employing partially implanted elements may also be used in accordance with the teachings provided herein.

In one illustrative, but non-limiting system, a control module is operably coupled to a signal generation module and instructs the signal generation module regarding the signal to be generated. For example, at any given time or period of time, the control module may instruct the signal generation module to generate an electrical signal having a specified pulse width, frequency, intensity (current or voltage), etc. The control module may be preprogrammed prior to implantation or receive instructions from a programmer (or another source) through any known or future developed mechanism, such as telemetry. The control module may include or be operably coupled to memory to store instructions for controlling the signal generation module and may contain a processor for controlling which instructions to send to signal generation module and the timing of the instructions to be sent to signal generation module. In various embodiments, leads are operably coupled to signal generation module such that a stimulation pulse generated by signal generation module may be delivered via electrodes.

While in certain embodiments, two leads are utilized, it will be understood that any number of one or more leads may be employed. In addition, it will be understood that any number of one or more electrodes per lead may be employed. Stimulation pulses are applied to electrodes (which typically are cathodes) with respect to a return electrode (which typically is an anode) to induce a desired area of excitation of electrically excitable tissue in a region of the cervical spine. A return electrode such as a ground or other reference electrode can be located on same lead as a stimulation electrode. However, it will be understood that a return electrode may be located at nearly any location, whether in proximity to the stimulation electrode or at a more remote part of the body, such as at a metallic case of a pulse generator. It will be further understood that any number of one or more return electrodes may be employed. For example, there can be a respective return electrode for each cathode such that a distinct cathode/anode pair is formed for each cathode.

The epidural electrode stimulation systems described herein are intended to be illustrative and non-limiting. Using the teachings provided herein, alternative epidural stimulation systems and methods will be available to one of skill in the art.

Use of Neuromodulatory Agents.

In certain embodiments, the transcutaneous and/or epidural stimulation methods described herein are used in conjunction with various pharmacological agents, particularly pharmacological agents that have neuromodulatory activity (e.g., are monoamergic). In certain embodiments, the use of various serotonergic, and/or dopaminergic, and/or noradrenergic, and/or GABAergic, and/or glycinergic drugs is contemplated. These agents can be used in conjunction with epidural stimulation and/or transcutaneous stimulation and/or physical therapy as described above. This combined approach can help to put the spinal cord (e.g., the cervical spinal cord) in an optimal physiological state for controlling a range of hand movements.

In certain embodiments, the drugs are administered systemically, while in other embodiments, the drugs are administered locally, e.g., to particular regions of the spinal cord. Drugs that modulate the excitability of the spinal neuromotor networks include, but are not limited to combinations of noradrenergic, serotonergic, GABAergic, and glycinergic receptor agonists and antagonists.

Dosages of at least one drug or agent can be between about 0.001 mg/kg and about 10 mg/kg, between about 0.01 mg/kg and about 10 mg/kg, between about 0.01 mg/kg and about 1 mg/kg, between about 0.1 mg/kg and about 10 mg/kg, between about 5 mg/kg and about 10 mg/kg, between about 0.01 mg/kg and about 5 mg/kg, between about 0.001 mg/kg and about 5 mg/kg, or between about 0.05 mg/kg and about 10 mg/kg.

Drugs or agents can be delivery by injection (e.g., subcutaneously, intravenously, intramuscularly), orally, rectally, or inhaled.

Illustrative pharmacological agents include, but are not limited to, agonists and antagonists to one or more combinations of serotonergic: 5-HT1A, 5-HT2A, 5-HT3, and 5HT7 receptors; to noradrenergic alpha 1 and 2 receptors; and to dopaminergic D1 and D2 receptors (see, e.g., Table 1).

TABLE 1

Illustrative pharmacological agents.

| Name | Target | Action | Route | Typical Dose (mg/Kg) | Typical Range (mg/kg) |
|---|---|---|---|---|---|
| Serotonergic receptor systems | | | | | |
| 8-OHDPAT | 5-HT1A7 | Agonist | S.C. | 0.05 | 0.045-0.3 |
| Way 100.635 | 5-HT1A | Antagonist | I.P. | 0.5 | 0.4-1.5 |
| Quipazine | 5-HT2A/C | Agonist | I.P. | 0.2 | 0.18-0.6 |
| Ketanserin | 5-HT2A/C | Antagonist | I.P. | 3 | 1.5-6.0 |
| SR 57227A | 5-HT3 | Agonist | I.P. | 1.5 | 1.3-1.7 |
| Ondanesetron | 5-HT3 | Antagonist | I.P. | 3 | 1.4-7.0 |
| SB269970 | 5-HT7 | Antagonist | I.P. | 7 | 2.0-10.0 |
| Noradrenergic receptor systems | | | | | |
| Methoxamine | Alpha1 | Agonist | I.P. | 2.5 | 1.5-4.5 |
| Prazosin | Alpha1 | Antagonist | I.P. | 3 | 1.8-3.0 |
| Clonidine | Alpha2 | Agonist | I.P. | 0.5 | 0.2-1.5 |
| Yohimbine | Alpha2 | Antagonist | I.P. | 0.4 | 0.3-0.6 |
| Dopaminergic receptor systems | | | | | |
| SKF-81297 | D1-like | Agonist | I.P. | 0.2 | 0.15-0.6 |
| SCH-23390 | D1-like | Antagonist | I.P. | 0.15 | 0.1-0.75 |
| Quinipirole | D2-like | Agonist | I.P. | 0.3 | 0.15-0.3 |
| Eticlopride | D2-like | Antagonist | I.P. | 1.8 | 0.9-1.8 |

The foregoing methods are intended to be illustrative and non-limiting. Using the teachings provided herein, other methods involving transcutaneous electrical stimulation and/or epidural electrical stimulation and/or the use of neuromodulatory agents to improve motor control and/or strength of a hand or paw will be available to one of skill in the ar.

EXAMPLES

The following examples are offered to illustrate, but not to limit the claimed invention.

Example 1

Enamine the Cervical Spinal Cord Circuitry to Re-Enable Volitional Control of Hand Function in Tetraplegic Patients The present Example demonstrates whether herein described neuromodulatory strategies can be used to improve fine motor control of the upper limbs, i.e., performance of motor tasks considered to be less "automatic" than posture and locomotion. Here we show that the injured human cervical spinal cord can be modulated using painless cutaneous electrical stimulation (pcEmc), monoaminergic agonist (fEmc) treatment, and/or eEmc to regain voluntary hand function. Mean hand strength increased greater than 300% after pcEmc plus fEmc (buspirone) treatment in 6 subjects with a chronic motor complete cervical injury. One subject that was implanted with a cervical epidural electrode array realized significantly improved hand strength and fine hand control in the presence of cervical eEmc. Thus, we now demonstrate that the cervical circuitry can be neuromodulated to improve volitional control of hand function in tetraplegic subjects with three novel interventions. The impact of these observations on individuals with upper limb paralysis could be dramatic functionally, psychologically, and economically.

Six subjects with chronic (18-36 months) spinal cord injury (SCI, traumatic cervical injury, ASIA B with no motor strength below the injury) were tested to determine if hand function can be improved by neuromodulating the cervical spinal cord. All subjects initially had minimal hand strength, a condition reflecting the majority of cervical SCI patients. Our experimental approach began with 6 weeks of baseline testing (Phase 1), followed by three 2-week treatment periods (Phases 2-4), and then by a period of approximately three months without any treatment at the end of which there was a final 2-week testing period (Phase 5). pcEmc at the C5 spinal segment (Phase 2) increased hand strength in 4/6 subjects compared to baseline Phase 1 (FIG. 1, panels A-G). During buspirone treatment (Phase 3), 4/6 subjects increased hand strength compared to Phase 1 and 2. The next 2 weeks buspirone was withdrawn but pcEmc continued (Phase 4), and again 4/6 subjects showed further improvement in grip strength compared to Phase 3. For all subjects combined, the mean grip strength tended to increase after each successive treatment phase (FIG. 1, panel G). EMG amplitudes were generally consistent with increases in grip force, i.e., digit flexor and extensor EMG amplitudes tended to increase progressively across phases (FIG. 1, panel H). After approximately three months without treatment, 4/6 subjects improved their performance relative to Phase 4.

These results show that the cervical spinal cord can be neuromodulated using two paradigms, i.e., electrically and pharmacologically. In some embodiments, the present methods are highly interactive and perhaps synergistic. Synergy and interactivity were observed in animal experiments. These data suggest that non-functional networks can become engaged and progressively improve motor performance. In some embodiments, further improvement in hand function after withdrawing pcEMC and fEMC can be a result of functional connections remaining active once they are established.

Figure 6:
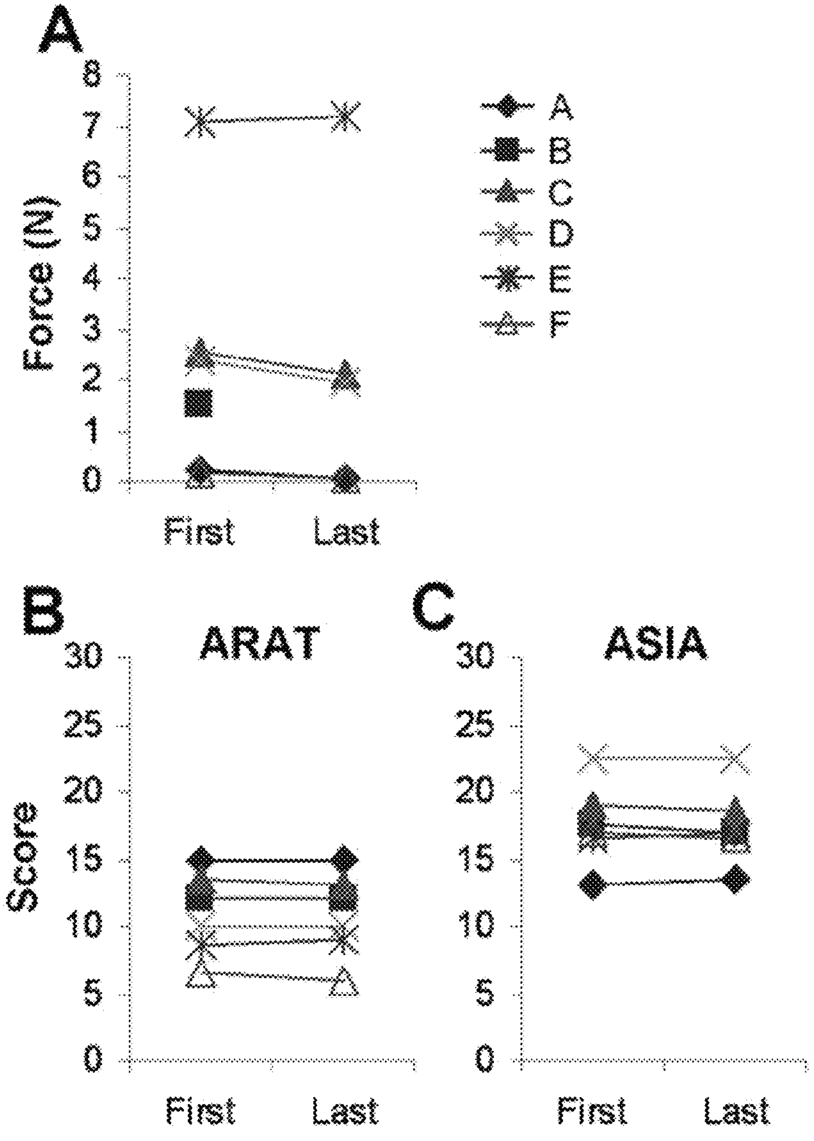
FIG. 6, panels A-C, shows that baseline testing (Phase 1) demonstrates stable hand function by handgrip device (panel A) and ARAT and ASIA scores (panel B) prior to initiation of any intervention. Maximal handgrip force on the last day of testing is not different from the first day of testing in the 6 subjects (panel A). Testing during this phase spanned a period of 6 weeks with bi-weekly testing sessions. Each data point represents an average of 3 maximal handgrip contractions. Clinical testing by ARAT and ASIA scores demonstrated no evidence of improvement during this initial baseline testing period (panel B).

The improvements are unlikely to be due to natural recovery or from repeated practice as large cohort studies of SCI patients have demonstrated that the majority of functional improvements occur within 6 months of the injury and that minimal recovery of function is observed past the 12 month time-point. All of our subjects were 18 months beyond the initial injury when recruited. Furthermore, baseline motor function testing for 6 weeks prior to any therapeutic intervention revealed stable function (FIG. 6). Concomitant to significantly improved hand strength, gains in upper extremity functional metrics by ARAT (13 point improvement) and ASIA (7 point improvement) tests, reflecting the impact of these interventions on the patient's overall upper extremity motor function (FIG. 1, panel I).

Figure 2:
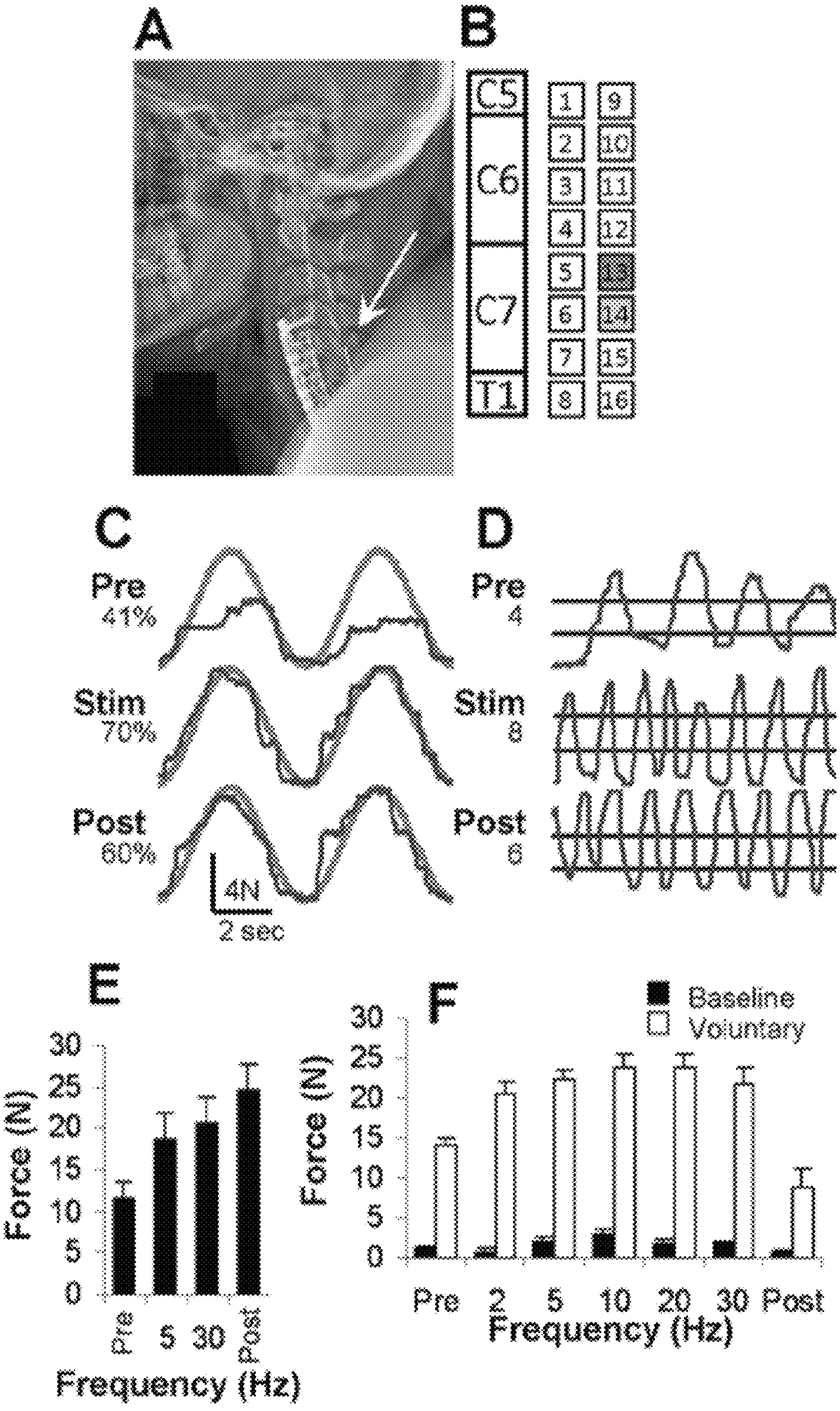
FIG. 2, panels A-L, shows motor performance relative to eEmc parameters. Subject E (C5 injury, ASIA panel B) was implanted with a 16-channel cervical epidural stimulation paddle array spanning spinal cord levels C5-T1, arrow pointing to electrode array (panels A and B). Prior to permanent implant, two parallel, temporary percutaneous linear electrodes were implanted. To assess hand control, the ability to accurately follow a targeted sign wave (panel C) and to perform rapid oscillations (panel D), and the maximal voluntary contraction (panel E) were determined during the initial day of eEmc before (Pre), during (Stim), and after (Post) stimulation (cathodes at C3 and anodes at T2, 30 Hz, 3.0 mA). After permanent paddle electrode implantation, stimulation at electrodes #13 and #14 (refer to schematic in panel B) was performed with the subject passive (Baseline) and when the subject attempted a voluntary contraction (Voluntary). Mean (t SEM, 3 trials for each condition) grip force during Baseline and Voluntary testing at varying stimulation frequencies (panel F) and intensities (panel G) are shown. Optimal stimulation parameters to affect hand function were assessed (panels H-J). Time to actuate the handgrip device (response time) was assessed at different stimulation frequencies and intensities (t SEM, 3 trials for each condition) (panel H). The parameter of 20 Hz, 0.7 mA elicited the shortest response time. Likewise, eEmc facilitated handgrip oscillation with doubling of oscillation ability compared to Pre and Post conditions of no stimulation (representative tracings shown) (panel I). Accuracy score during sinusoidal wave testing in response to varying frequencies of stimulation was assessed with the best scores observed at 20 Hz (±SEM, 3 trials for each condition) (panel J). Assessment of accuracy score over different sessions revealed chronic improvement with sinusoidal wave test (±SEM, 24 trials for each condition at electrode combinations of +13-14 and +13-6, 5-30 Hz, 0.7 mA) (panel K). These improvements in hand function in response to eEmc were evident in the acute improvements in clinical ARAT score with multi-site electrode combination (Stim) (70% at −12+3, 30% at −12+4, 5 Hz, 0.9 mA) (panel L). The improvement of 6 points in ARAT score reflects a clinically significant event. This 20% increase reflects improvements in all categories measured by ARAT and is above the minimal clinically important difference of 5.7 points established for this instrument (van der Lee et al. (2001) *J. Rehabil. Med.* 33: 110-113), demonstrating the relevance of this intervention in improving upper extremity function.
Figure 3:
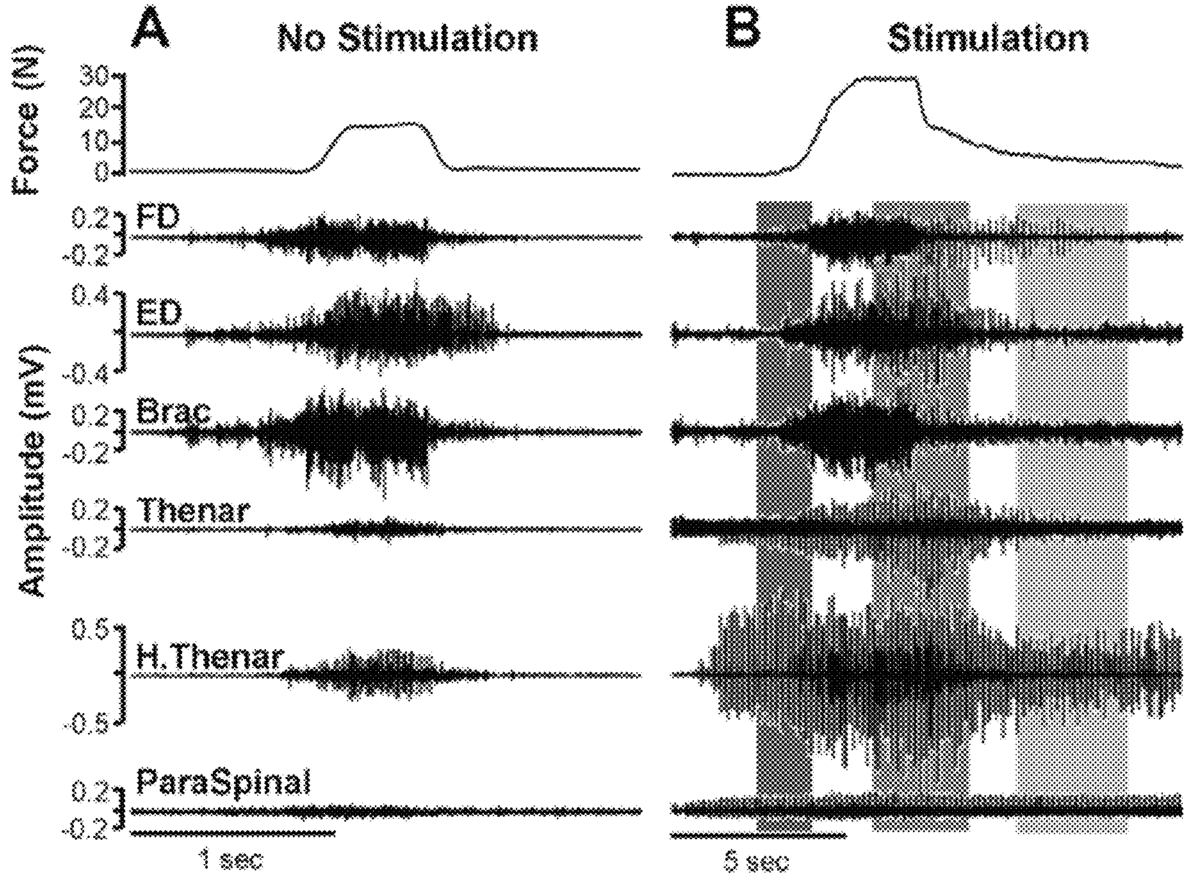
FIG. 3, panels A-E, shows hand grip force and evoked potentials in Subject E. Handgrip force and EMG during a maximum handgrip performed without (panel A) and with eEmc (panel B) of the cervical spinal cord (electrodes +13-14, 10 Hz, 1 mA). In (panel B), the initial stimulation phase without any voluntary effort (blue shaded area), the voluntary contraction phase (red shaded area), and the relaxation phase of the voluntary effort (green shaded area) are shown. At least twenty evoked potentials in each muscle were averaged during each phase. Note that an evoked potential was clearly evident in all muscles during the contraction and relaxation phases, but only in the H. thenar during the initial stimulation phase without any voluntary effort. The effect of frequency of stimulation on the average evoked potentials for 3 sec during the initial stimulation phase without any voluntary effort and during the voluntary contraction phase in each muscle are shown in panel C. The data demonstrate a substantially reduced evoked response in all muscles at the higher frequencies (20 and 30 Hz) during the voluntary contraction phase, but no substantial loss of force. The increase in force and two components of the EMG signal of the FD muscle during the initial phase of contraction is shown in panel E. The iEMG is divided into the energy (pV.sec) derived from evoked potentials synchronized with the stimulation pulses (20 Hz) and the total iEMG energy, i.e., the combination of the synchronized signals and that occurring randomly with respect to the stimulation pulses. The samples used for plotting the force are separated into those time bins when the EMG signals are largely alternating in amplitude. The + sign represents bins with the lowest amplitude and the triangles represent those with the highest amplitudes. The presence or absence of the lower synchronized signal had no impact on the force generated during a given time bin. H. Thenar, hypothenar; ER evoked response.
Figure 7:
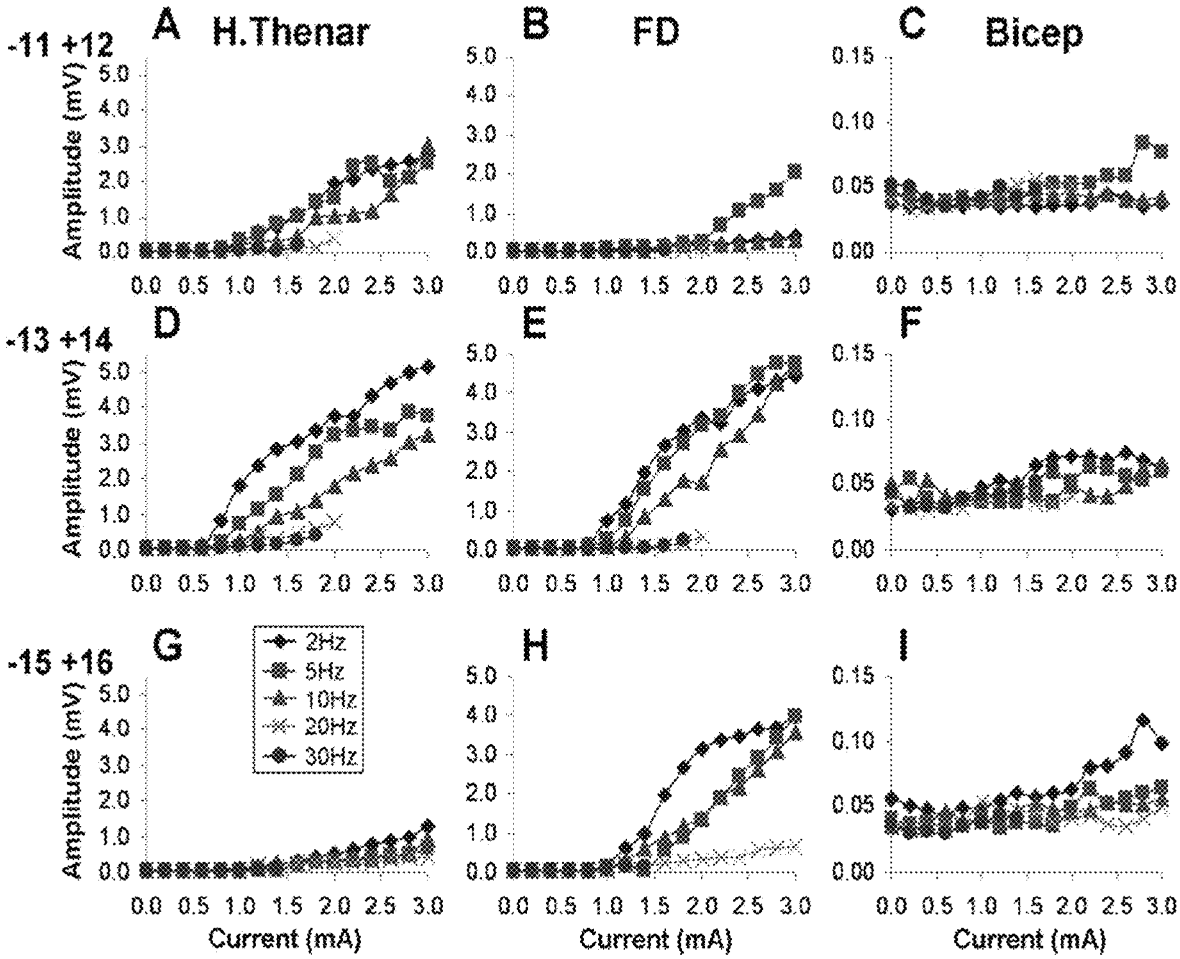
FIG. 7, panels A-I, show amplitudes of spinal cord evoked potentials induced by cathode-anode epidural electrode pairs with a range of currents and frequencies starting from the rostral to caudal spinal cord (refer to FIG. 2B for electrode configuration). The amplitude of the potentials demonstrates the relative responsiveness of each motor pool to the stimulation at a specific spinal location at a given level of current and frequency. The cathode-anode pair of −13+14 produced the most activation of muscles associated with hand function, i.e., H. Thenar and FD, and was used for most of the study.

Given the results above, we then asked whether the cervical spinal circuitry could be neuromodulated to improve hand function by stimulating via an epidural array implant (implanted in subject shown in FIG. 1, panel E). The implanted stimulating electrodes spanned the caudal portion of C5 to the rostral portion of T1 (FIG. 2, panel A, arrow; FIG. 2, panel B, electrode diagram). After mapping of the cervical motor pools by spinal cord evoked potentials (FIG. 7) we mainly used electrodes 13 and 14 to modulate hand function (FIG. 2, panel B, shaded boxes).

In the initial acute phase after implantation of a temporary trial array, the subject's ability to accurately follow a targeted force presented with a cursor moving in a sine wave pattern on a video screen was improved with eEmc (FIG. 2, panel C). The subject also could generate a more rapid oscillating force above and below a pre-selected target force in the presence of stimulation (FIG. 2, panel D). Additionally, handgrip force was increased with stimulation at 5 and 30 Hz (FIG. 2, panel E). Importantly, some of these improvements were observed after stimulation.

After implantation of the permanent electrode array, we next performed a series of motor tests over the next 9 months comparing the effects of different stimulation parameters in facilitating maximum force and fine control. Maximal forces were generated at 10-20 Hz (FIG. 2, panel F) and 0.7-1.3 mA (FIG. 2, panel G). These forces were lower than the force generated in normal subjects (approximately 400 N), but substantially more than baseline. Evidence of the importance of selecting the optimal frequency and intensity of stimulation was reflected in the time that it took to respond to a signal to begin generating a force (FIG. 2, panel H). However, there were extremely long delays (sec) relative to uninjured subjects (approximately 200 ms) in voluntarily initiating a force regardless of the stimulation parameters. We compared the performance of these motor tasks to a commonly used clinical assessment tool and found a 6-point increase in ARAT with eEmc on vs. off during the same testing session, demonstrating the clinical relevance (FIG. 2, panel L).

Accuracy in controlling force was performed approximately weekly over a period of eight months to identify the optimal stimulation parameters. Rapid oscillatory movements were performed at 20 Hz and 0.5 mA and at 10 and 30 Hz and 0.7 mA (FIG. 2, panel 1). Accuracy in following a targeted force occurred at 20 Hz (FIG. 2, panel J). In addition, the accuracy of controlling force in a sine wave pattern almost doubled over a two-month period (FIG. 2, panel K).

The present methods and systems provide that: 1) optimal stimulation parameters generating the highest forces differed from those generating the greatest accuracy at sub-maximal forces; 2) effects of stimulation intensity and frequency on maximum force production and accuracy are highly interdependent; 3) accuracy of force generation can be improved over time in the presence of eEmc; and 4) time needed to initiate a force following a command was prolonged, but could be improved with specific stimulation parameters. Each of these observations demonstrates the importance of matching the stimulation parameters with the task to be performed. In some embodiments, eEmc can yield improvement (e.g., meaningful) in upper extremity function in subjects with a cervical SCI.

Accuracy in controlling force was performed approximately weekly over a period of eight months to identify the optimal stimulation parameters. Rapid oscillatory movements were performed at 20 Hz and 0.5 mA and at 10 and 30 Hz and 0.7 mA (FIG. 2, panel 1). Accuracy in following a targeted force occurred at 20 Hz (FIG. 2, panel J). In addition, the accuracy of controlling force in a sine wave pattern almost doubled over a two-month period (FIG. 2, panel K).

The present methods and systems provide that: 1) optimal stimulation parameters generating the highest foxes differed from those generating the greatest accuracy at sub-maximal forces; 2) effects of stimulation intensity and frequency on maximum force production and accuracy are highly interdependent: 3) accuracy of force generation can be improved over time in the presence of eEmc; and 4) time needed to initiate a force following a command was prolonged, but could be improved with specific stimulation parameters. Each of these observations demonstrates the importance of matching the stimulation parameters with the task to be performed. In some embodiments, eEmc can yield improvement (e.g., meaningful) in upper extremity function in subjects with a cervical SCI.

Figure 4:
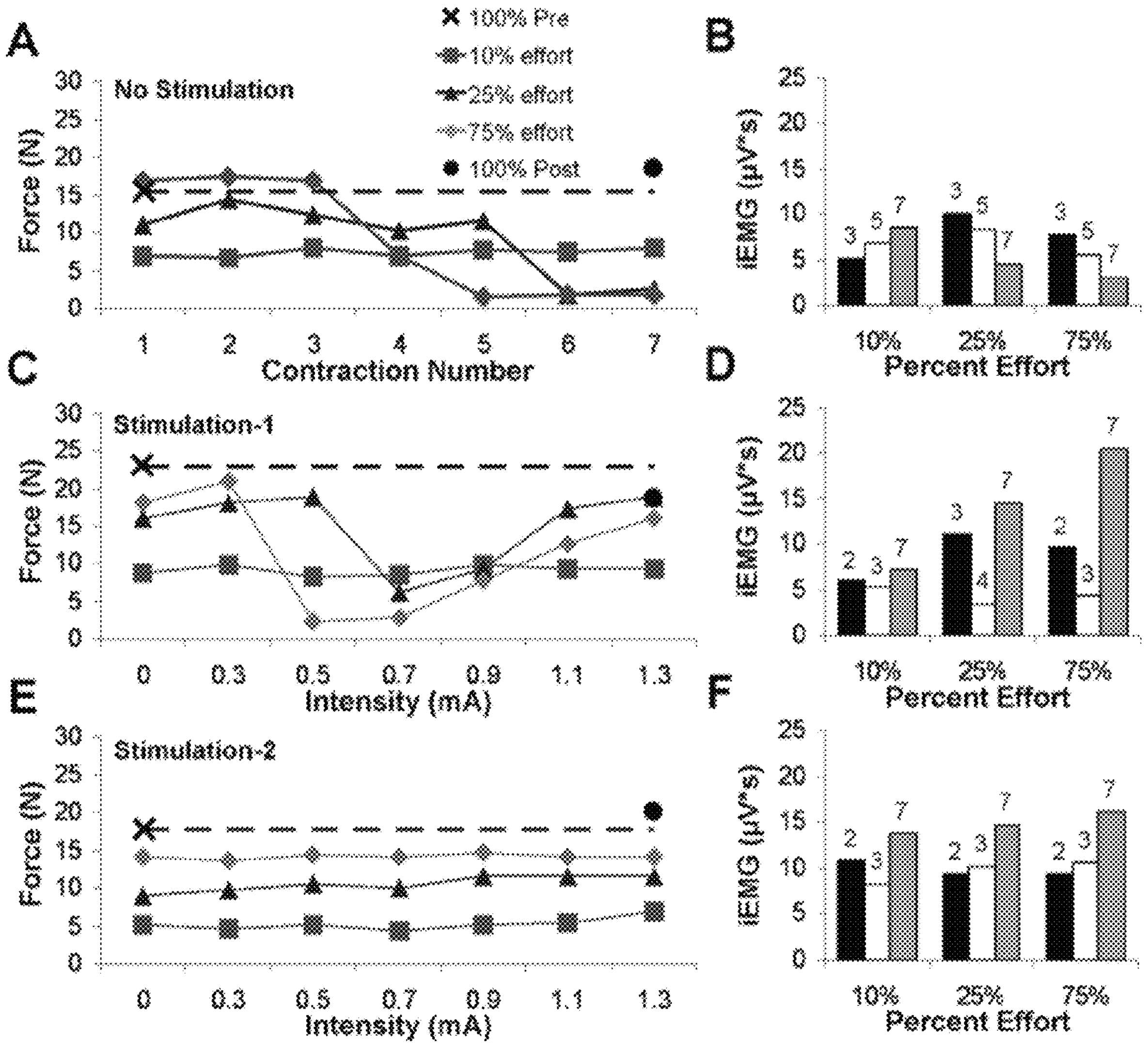
FIG. 4, panels A-H, shows handgrip forces and evoked responses at different % maximum efforts in Subject E. Handgrip force for a maximum contraction at the beginning of testing (100% Pre) followed by 7 consecutive contractions (5 sec between each contraction, and 5 min of rest between different efforts) at 10 (red), 25 (blue), 75 (green) % effort, and after 10 min of rest for a maximum contraction at the end of testing (100% Post) with no stimulation (A). The FD integrated EMG (iEMG) within this series of efforts is shown in (B). Numbers above the bars in (B), (D), and (F) are linked to the contraction numbers as labeled in (A). Fifteen min after the completion of (A), the same series of contractions were repeated in the presence of increasing intensities of stimulation ((C) and (D)). In this case, fatigue was evident at 0.7 and 0.5 mA when the subject was exerting 25 and 75% effort, respectively. Stimulation at the higher intensities enabled the subject to overcome substantial levels of fatigue. Additionally, there was an associated increase in iEMG compared to the initial contractions without fatigue as well as those in which fatigue occurred (D). To determine whether this fatigue effect was associated with repetitive contractions on the same day as in (A) and (C), on a separate day the same series of efforts at the same level of stimulation intensities were examined. In this case, there was no obvious fatigue (E) at any stimulation intensity as indicated by the constant forces and only minor increases in iEMG (F). The patterns of evoked potentials at selected percent efforts and at different strengths of stimulation when there was substantial fatigue and when there was no apparent fatigue is shown in (G) and (H), corresponding to iEMG (D) and (F), respectively. In spite of the absence of evidence of fatigue as indicated by the force with repeated contractions, to maintain that force may require higher intensities of stimulation to sustain the forces generated at the end of each series of contractions at a given percent effort (H). Stimulation parameters were electrode pattern of −13+14, 20 Hz, 0-1.3 mA.

A dysfunctional interaction may exist between supraspinal and sensory networks given the externally imposed neuromodulation of the spinal circuitry and since neither the descending motor control nor the spinal circuitry had functioned in any significant interactive way since the injury. This interaction was explored between supraspinally derived descending volitional drive and sensory-derived input to the spinal networks and motor pools when the spinal circuitry was being neuromodulated with eEmc. Could supraspinal networks volitionally accommodate the 'level of effort' to the level of motor pool excitability imposed by eEmc? To address this question we asked the subject to generate a series of seven contractions at different levels of maximum efforts with and without stimulation (FIG. 4). Without stimulation, the force level was maintained for all seven contractions at the lowest percentage effort, but force declined during the later contractions at the higher percentage efforts (FIG. 4, panel A). Over a wide range of stimulation intensities at the lowest percent effort, there were no marked differences in the subject's ability to estimate a target force (FIG. 4, panel C). At higher percent efforts fatigue was evident at moderate stimulation intensities, but this was overcome at the higher levels of stimulation, suggesting a neural deficit (FIG. 4, panels A and C). We repeated the experiments shown in FIG. 4, panels A and C (which occurred within 15 min period) on another day to avoid possible neuromuscular fatigue (FIG. 4, panel E). At the lower percent effort without stimulation, there was greater recruitment during the later contractions that enabled a constant force, whereas at the higher percent efforts the subject was unable to compensate with greater recruitment (FIG. 4, panel B). With stimulation, however, even at the higher efforts the targeted force could be reached as the result of greater motor pool excitation (FIG. 4, panel D). A similar but less dramatic change in excitation of the motor pools was present even when the targeted forces were reached at the different percent efforts (FIG. 4, panels D, F-H). In spite of the wide range in levels of neuromodulation there was remarkable consistency in volitionally generated forces. These results suggest that the subjects consciously perceived rather accurately the combined physiological state of supraspinal, spinal, and sensory networks to achieve the targeted levels of force simply defined conceptually as a "percent maximum effort" even in the presence of fatigue.

PcEmc, fEmc, and eEmc interventions can enhance the level of excitability of pre-motor spinal circuitries that mediate hand function. The importance of these data is that they identify three novel interventional strategies having significant potential for high clinical impact in a relatively short timeframe on a function considered to be of highest priority among paralyzed patients. The impact of these results is significant from the following perspectives: 1) neuromodulation is not dependent on the physiological phenomenon of central pattern generation but also applies to fine neuromotor control of less "automatic" movements; 2) they raise the possibility that the neuromodulatory concept could apply to other neural networks and therefore could be applied to neuromotor disorders such as stroke and Parkinson disease; and 3) they demonstrate the potential of enhancing maximum neuromuscular force, as well as fine control of movements. The improved force potential was associated with improved performance in upper extremity tasks (ARAT). Importantly, even after more than a year of inactivity of the sensorimotor circuits, significant levels of activity-dependent plasticity persist.

Methods Summary

The University of California, Los Angeles Institutional Review Board approved all procedures. Subjects were enrolled based on the enrollment criteria of traumatic cervical injury, ASIA B, greater than 1 year from injury, and stable motor function as documented by sequential clinical exams. Baseline clinical scores (ARAT, ASIA) prior to study intervention were assessed (FIG. 1, panel I).

Voluntary motor control data were assessed using a handgrip force measurement device. EMG data were collected via surface electrodes placed unilaterally on upper extremity muscles. Stimulation and data collection was obtained using the Konigsberg EMG system (Konigsberg. Pasadena, California). Functional assessments by ASIA and ARAT validated assessment tools were performed weekly during each study phase. Two blinded examiners conducted the functional tests.

Backup

The maximum score for each upper limb is 25 (0.5 muscles×5 points), totaling 50 for both upper limbs. (scire-project.com/outcome/ais/)[ ](https://www.physio-pedia-.com/
American_Spinal_Cord_lnjury_Association_%28ASIA %29_Impairment_Scale)

The transcutaneous stimulation device is non-invasive. Stimulation parameters ranged from 5-30 Hz and 20-100 mA, located at C5. From the midpoint of Phase 1 to the end of Phase 4 all subjects were informed that they would receive either a placebo or the monoaminergic agonist (7.5 mg buspirone twice daily for 2 weeks beginning the day before biweekly testing). All subjects received buspirone during Phase 3 and a placebo during Phases 1, 2, and 4. All subjects and testers were blinded.

A temporary trial with two 16-contact percutaneous epidural leads (Linear Lead, Boston Scientific, Valencia. CA) spanning C2 to T1 was conducted prior to permanent implantation in one subject. Indication for implantation was for treatment of pain. Stimulation intensity ranged between 0.1-10.0 mA, frequencies ranged between 5-60 Hz, and pulse width was at 210 or 450 μs. After 7 days, one Boston Scientific Artisan (Valencia, CA) 16-electrode epidural array and one Boston Scientific Precision Plus Spinal Cord Stimulator (Valencia. CA) were implanted encompassing C5 to T1. The effects of various combinations of stimulation parameters were assessed to obtain the best response for hand function. Stimulation intensity ranged between 0.13.0 mA, frequencies ranged between 5-60 Hz, and pulse width was at 210 or 450 ps.

Outcomes were averaged across all observations in a given phase/period for each subject. Group mean changes across subjects in grip strength, EMG amplitude, ARAT score and ASIA score from baseline over the 5 phases were compared using a non-parametric repeated measure analysis of variance model using re-sampling. A two sided p value of $p<0.05$ was considered significant. Means±standard error of the mean (SEM) are reported.

Method

Subject Profiles

Figure 5:
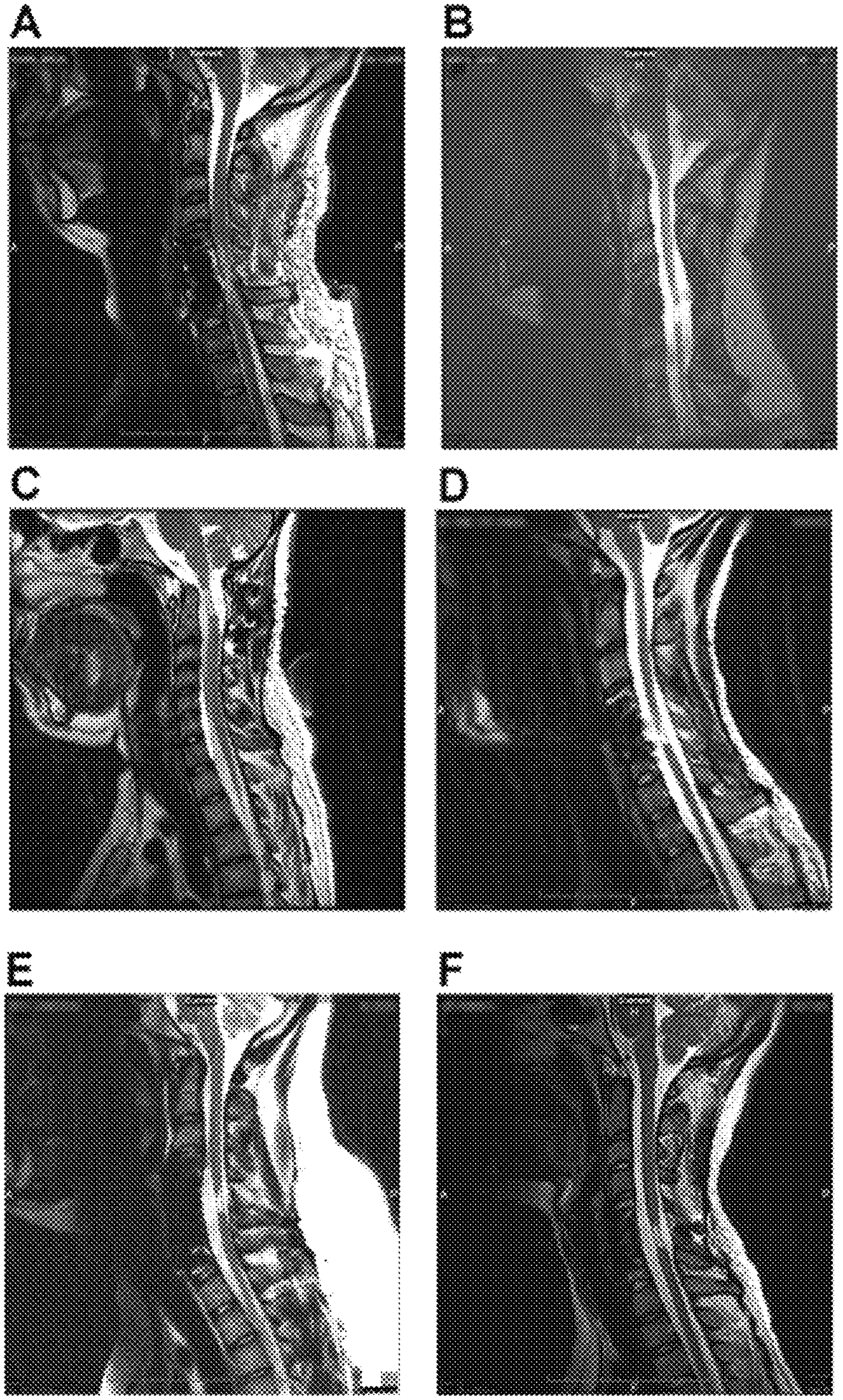
FIG. 5, panels A-F, shows sagittal T2 MRI Imaging demonstrating location of cervical spinal cord injury of subjects A-F, approximating C2 (panel C), C5 (panels B, D. E) or C6 (panels A, F) spinal cord segment. Normal tissue at injury location is replaced by a high intensity signal representing a glial scar. Spinal cord tissue distal and proximal to the injury locus is seen to be intact without evidence of post-traumatic syrinx formation or on-going compressive lesion.

The University of California, Los Angeles Institutional Review Board approved all procedures. Subjects were enrolled based on the enrollment criteria of traumatic cervical injury, ASIA B, greater than 1 year from injury, and stable motor function as documented by sequential clinical exams. The clinical profiles of the subjects upon enrollment into this study are as follows: Subject A was a 20 year old male who suffered a C6 SCI after a motor vehicle accident and was 36 months from initial injury: Subject B was a 18 year old male who suffered a C5 SCI after a diving accident and was 18 months from initial injury; Subject C was a 21 year old female who suffered a C2 SCI after a motor vehicle accident and was 45 months from initial injury; Subject D was a 20 year old male who suffered a C5 SCI sustained during football game and was 30 months from initial injury; Subject E was a 18 year old male who suffered a C5 SCI after a diving accident and was 24 months from initial injury; and Subject F was an 18 year old female with C6 SCI sustained after a fall from height and was 18 months from initial injury. Magnetic resonance imaging was obtained in all subjects to confirm location and description of injury (FIG. 5). Baseline clinical scores (ARAT, ASIA) were assessed prior to and throughout the study (FIG. 1, panel 1).

Hand Testing

Voluntary motor control data were assessed using a handgrip force measurement device. Motor assessment was conducted on the arm that was most functional post-injury regardless of the pre-injury dominant side. Briefly, the device measures displacement against springs with a range in spring constants. Measurement of maximal voluntary contraction was conducted by asking the subject to contract his/her hand against the springs to maximally displace the handgrip. The contraction lasted for approximately 3-5 sec and was repeated twice. For hand oscillation/repeated contractions, the subject was asked to contract and release the hand as fast as possible above and below two lines on a computer screen that was preset at 12.5 and 37.5% of maximum voluntary contraction. The number of completed contraction-release sequences across the lines was determined. For hand control, the subject was asked to trace a sinusoidal wave (0.15 Hz) that appeared on the computer screen by squeezing the handgrip. The percentage of data points that fell inside a circular window at a sampling of 15 Hz was determined. The EMG data were collected via surface electrodes placed unilaterally on the biceps brachii (biceps), triceps brachii (triceps), brachioradialis (Brac), extensor digitorum (ED), flexor digitorum (FD), thenar, and hypothenar (H. Thenar) muscles. Stimulation and data collection was obtained using the Konigsberg EMG system (Konigsberg, Pasadena. California). Functional assessments by validated assessment tools were performed weekly during each phase of study: American Spinal Injury Assessment (ASIA), and Action Research Arm Test (ARAT) (Carroll (1965) *J. Chronic Dis.,* 18: 479-491).

ARAT was selected due its focus on arm motor ability and because it has been validated and applied in the SCI setting. Scoring was conducted by two experienced examiners who were not informed of the treatment phase (blinded). If discrepancy existed between the scores, the exam was repeated and a consensus reached.

Prior to initiation of the study, the stability of hand function and training effect of utilizing the handgrip was assessed over the course of 6 weeks during which the subjects were tested and trained with the handgrip twice/ week. In all subjects assessed, there was no improvement in hand function during this baseline testing (FIG. 6). Testing and training during this assessment period involved asking the subject to maximally contract the hand using the handgrip device. A total of 9-36 maximum hand contractions were performed during each session over a period of one to two hours.

pcEMC and fEMC

The transcutaneous stimulation device is non-invasive. A surface stimulation cathode electrode was attached on the dorsal aspect of the neck (C5 area) and the grounding electrode was placed on the anterior superior iliac spine. Stimulation parameters ranged from 5-30 Hz and 20-100 mA. Varying combinations of these stimulation parameters were systematically assessed to obtain optimum facilitation of voluntary hand contraction by identification of the relative activation levels of the motor pools studied (data not shown). During each of the three treatment periods (Phases 2-4) a series of nine 3.5-sec maximum hand grip strength tests were performed per treatment session. In each session of Phase 2, three contractions were performed without pcEmc, followed by three in the presence of pcEmc (twice weekly at 30 Hz and 20-40 mA), followed by three without pcEmc. The same pcEmc protocol was followed during Phases 2-4. The duration of pcEmc during each testing session was approximately 15-30 min. The total number of maximum hand contractions was 9-36 and each session lasted 1 to 2 hours. During pcEMC, the subjects reported a non-painful, tingling sensation down the arms at the higher stimulation intensities at the site of stimulation with some associated tonic paraspinal muscle contractions at the neck.

From the midpoint of the Phase 1 to the end of Phase 4 all subjects were informed that they would receive either a placebo or the monoaminergic agonist buspirone. All subjects and testers were blinded as to which treatment was administered and were given buspirone (7.5 mg buspirone twice daily for 2 weeks beginning the day before biweekly testing) during Phase 3 and a placebo during Phases 1, 2, and 4.

eEMC

Planning for surgical placement of spinal cord epidural stimulator (eEmc) on subject E was initiated prior to study enrollment. The criteria for selection was based on Federal Drug Administration approved use for the treatment of pain and Dr. Lu and two other physicians confirmed the indication for implantation. A temporary trial with two 16-contact percutaneous epidural leads (Linear Lead, Boston Scientific. Valencia, CA) spanning C2 to T1 was conducted prior to permanent implantation. After implantation, testing was conducted over a 2-hour session to assess the efficacy for improving hand function. Stimulation amplitude ranged between 0.110.0 mA, frequencies ranged between 5-60 Hz, and pulse width was at 210 or 450 ps. Total time of stimulation was 30 min.

After 7 days of confirmed efficacy in the treatment of pain, one Boston Scientific Artisan (Valencia, CA) 16-electrode epidural array and one Boston Scientific Precision Plus Spinal Cord Stimulator (Valencia. CA) were implanted encompassing C5 to T1. The effects of various combinations of stimulation parameters were assessed to obtain the best response for hand function. A combined total of 60 testing sessions were conducted on Subject E over the course of 20 months (epidural implant occurred between testing session 21 and 22). Each testing session lasted up to 180 min. During each testing session, stimulation duration lasted between 30-120 min. Stimulation amplitude ranged between 0.1-3.0 mA, frequencies ranged between 5-60 Hz, and pulse width was at 210 or 450 ps. During low intensity eEMC, the subject reported a tingling sensation at the neck that migrated toward the arms and hands. At the optimal stimulation parameters, the subject reported the perception of increased hand strength and control similar to pre-injury ability.

STATISTICAL ANALYSIS

Outcome measures (grip strength force, EMG amplitude, ARAT score, ASIA score) were averaged across all observations in a given Phase for each subject. Using these values, group mean changes across subjects for each outcome measure from baseline over the 5 phases were compared using a non-parametric repeated measure analysis of variance model using re-sampling (bootstrap). The repeated measure mixed model takes into account the correlation across time on the same subjects. A two-sided p value of $p<0.05$ was considered significant. Standard error of the mean (SEM) are reported. Individual mean profiles and the corresponding within person SEM also are reported.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A transcutaneous electrical spinal cord stimulation system, comprising:

a pulse generator having a control circuitry configured to generate electrical signals to modulate proprioceptive and supraspinal information in spinal circuits controlling the upper limbs of a subject having upper limb paralysis;

at least one surface stimulation electrode configured to be placed along a dorsal aspect of the neck of the subject at least partially corresponding to the cervical spine;

wherein the control circuitry provides subthreshold electrical signals having parameters including amplitude, frequency, pulse width, voltage and current, the parameters configured to improve, when the electrical signal is provided to the at least one stimulation electrode, the motor function of at least one of elbow flexors, wrist extensors, elbow extensors, finger flexors or finger abductors.

2. The system of claim 1, wherein the at least one stimulation electrode is configured to be positioned at least at one spinal segment from C5 to T1.

3. The system of claim 1, wherein the pulse generator is configured to neuromodulate one or more regions of the spinal circuitry of the subject straddling or spanning a region selected from the group consisting of C1-C1, C1-C2, C1-C3, C1-C4, C1-C7, C1-C6, C1-C7, C1-T1, C2-C2, C2-C3, C2-C4, C2-C5, C2-C6, C2-C7, C2-T1, C3-C3, C3-C4, C3-C5, C3-C6, C3-C7, C3-T1, C4-C4, C4-C5, C4-C6, C4-C7, C4-T1, C5-C5, C5-C6, C5-C7, C5-T1, C6-C6, C6-C7, C6-T1, C7-C7, and C7-T1.

4. The system of claim 1, wherein the parameters of the electrical signals are configurable by the control circuitry.

5. The system of claim 1, wherein at least one of the at least one stimulation electrode is a part of an electrode array comprising a plurality of electrodes.

6. The system of claim 1, further comprising a return electrode.

7. The system of claim 1, wherein the at least one of the amplitude, frequency, pulse width, voltage, or current of the electrical signal is further configured to increase grip strength of a subject.

8. The system of claim 1, wherein the at least one of the amplitude, frequency, pulse width, voltage, or current of the electrical signal is further configured to increase activation levels of motor pools of the upper limbs of the subject.

9. The system of claim 1, wherein the at least one of the amplitude, frequency, pulse width, voltage, or current of the electrical signal is further configured to increase activation levels of motor pools of the hands of the subject.

10. The system of claim 9, wherein the increase in activation levels of motor pools of the hand of the subject comprises an increase in surface EMG amplitudes of at least one intrinsic or extrinsic muscle of the hand.

11. The system of claim 1, wherein: the amplitude of the electrical signal is between 20 mA and 100 mA, and the frequency of the electrical signal is between 5 Hz and 30 Hz.

12. The system of claim 1, wherein: the amplitude of the electrical signal is between 0.1 mA and 10 mA, and the frequency of the electrical signal is between 5 Hz and 60 Hz.

13. The system of claim 1, wherein the at least one of the amplitude, frequency, pulse width, voltage, or current of the electrical signal is further configured to reduce a time needed to initiate a force following a subject command.

14. The system of claim 1, wherein the at least one electrode straddles or spans the C3-C4 region of the subject.

15. The system of claim 1, wherein the at least one electrode straddles or spans the C5-C6 region of the subject.

16. The system of claim 5, wherein the control circuitry is configured for selectable activation or stimulation of one or more electrodes; wherein the electrode selection, frequency, amplitude, and pulse width are independently selectable such that different electrodes can provide different stimulation frequencies and/or amplitudes at different times.

17. The system of claim 5, wherein different electrodes or all electrodes can be operated in a monopolar mode and/or a bipolar mode, using constant current or constant voltage delivery of the stimulation.

18. The system of claim 1, wherein the at least one surface stimulation electrode further comprises a lead.

19. The system of claim 18, wherein the lead comprises a plurality of electrodes.

20. An electrical stimulation system, comprising:

a pulse generator configured to neuromodulate the spinal circuitry of a subject by providing an electrical signal to at least one stimulation electrode placed along a dorsal aspect of the neck of the subject; and wherein at least one of an amplitude, frequency, pulse width, voltage or current of the electrical signal are selected to improve, when the electrical signal is provided to the at least one stimulation electrode, at least one of flexion, extension or abduction for at least one myotome of an arm of the subject.

21. The system of claim 20, wherein the at least one stimulation electrode is configured to be positioned at least at one spinal segment C5 to T1.

22. An electrical stimulation system, comprising:

a pulse generator configured to neuromodulate the spinal circuitry of a subject by providing an electrical signal to at least one stimulation electrode placed along a dorsal aspect of the neck of the subject; and wherein at least one of an amplitude, frequency, pulse width, voltage or current of the electrical signal are selected to improve, when the electrical signal is provided to the at least one stimulation electrode, fine motor control of the wrists and/or fingers of the subject.

23. The system of claim 22, wherein the at least one stimulation electrode is configured to be positioned at least at one spinal segment from C5 to T1.

* * * * *